(12) United States Patent
Ducray et al.

(10) Patent No.: US 7,705,044 B2
(45) Date of Patent: *Apr. 27, 2010

(54) BENZAMIDOACETONITRILES AND THEIR USE AS ANTIPARASITICS

(75) Inventors: Pierre Ducray, Village-Neuf (FR); Jacques Bouvier, Neuchâtel (CH); Matthias Keller, Basel (CH); Corina Bergamin, Allschwil (CH)

(73) Assignee: Novartis AG, Basel (CH)

( * ) Notice: Subject to any disclaimer, the term of this patent is extended or adjusted under 35 U.S.C. 154(b) by 1640 days.

This patent is subject to a terminal disclaimer.

(21) Appl. No.: 10/477,289

(22) PCT Filed: May 14, 2002

(86) PCT No.: PCT/EP02/05294

§ 371 (c)(1),
(2), (4) Date: Jun. 1, 2004

(87) PCT Pub. No.: WO02/092552

PCT Pub. Date: Nov. 21, 2002

(65) Prior Publication Data

US 2004/0220055 A1    Nov. 4, 2004

(30) Foreign Application Priority Data

May 15, 2001    (CH) .................................... 0919/01

(51) Int. Cl.
  *C07C 255/44*    (2006.01)
  *A61K 31/277*    (2006.01)
  *A61P 33/10*    (2006.01)
  *A61P 33/14*    (2006.01)

(52) U.S. Cl. .............. 514/463; 514/468; 514/521; 514/617; 514/622; 549/438; 549/466; 558/392

(58) Field of Classification Search .............. 514/183, 514/621, 463, 468, 521, 617, 622; 424/405; 504/100; 549/438, 466; 558/392
See application file for complete search history.

(56) References Cited

U.S. PATENT DOCUMENTS

| | | | | |
|---|---|---|---|---|
| 4,873,224 A | * | 10/1989 | Linn et al. | 514/30 |
| 7,091,371 B2 | * | 8/2006 | Ducray et al. | 558/392 |
| 7,521,476 B2 | * | 4/2009 | Ducray et al. | 514/463 |
| 2006/0128801 A1 | * | 6/2006 | Ducray et al. | 514/521 |

FOREIGN PATENT DOCUMENTS

| | | | |
|---|---|---|---|
| EP | 375 393 | * | 12/1989 |
| EP | 0 953 565 | | 11/1999 |
| EP | 953 565 | * | 11/1999 |

* cited by examiner

*Primary Examiner*—Alton N Pryor

(57) ABSTRACT

The invention relates to compounds of the general formula

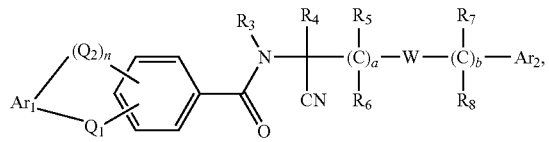

I and optionally the enantiomers thereof. These compounds have advantageous pesticidal properties. They are especially suitable for controlling parasites in warm-blooded animals.

12 Claims, No Drawings

BENZAMIDOACETONITRILES AND THEIR USE AS ANTIPARASITICS

This application is a National Phase Application under 0371 of International Application Number PCT/EP02/005294 filed on May 14, 2002.

The present invention relates to new benzamidoacetonitrile compounds of formula

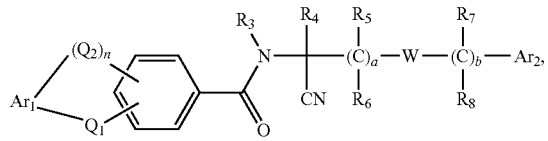

I wherein $Ar_1$ and $Ar_2$, independently of one another, signify unsubstituted phenyl or phenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyl, halo-$C_2$-$C_6$-alkenyl, $C_2$-$C_6$-alkinyl, $C_3$-$C_6$-cycloalkyl, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylsulfonyloxy, halo-$C_1$-$C_6$-alkylsulfonyloxy, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_2$-$C_6$-alkenylthio, halo-$C_2$-$C_6$-alkenylthio, $C_2$-$C_6$-alkenylsulfinyl, halo-$C_2$-$C_6$-alkenylsulfinyl, $C_2$-$C_6$-alkenylsulfonyl, halo-$C_2$-$C_6$-alkenylsulfonyl, $C_1$-$C_6$-alkylamino, di-$C_1$-$C_6$-alkylamino, $C_1$-$C_6$-alkylsulfonylamino, halo-$C_1$-$C_6$-alkylsulfonylamino, $C_1$-$C_6$-alkylcarbonyl, halo-$C_1$-$C_6$-alkylcarbonyl, $C_1$-$C_6$-alkoxycarbonyl, $C_1$-$C_6$-alkylaminocarbonyl, di-$C_1$-$C_6$-alkylaminocarbonyl; unsubstituted phenyl or phenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl; unsubstituted phenoxy or phenoxy which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl; unsubstituted phenylacetylenyl or phenylacetylenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl; and unsubstituted pyridyloxy or pyridyloxy which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl;

unsubstituted heteroaryl or heteroaryl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_2$-$C_6$-alkenylthio, halo-$C_2$-$C_6$-alkenylthio, $C_2$-$C_6$-alkenylsulfinyl, halo-$C_2$-$C_6$-alkenylsulfinyl, $C_1$-$C_6$-alkylsulfonyl and halo-$C_1$-$C_6$-alkylsulfonyl, $C_2$-$C_6$-alkenylsulfonyl, halo-$C_2$-$C_6$-alkenylsulfonyl, $C_1$-$C_6$-alkylamino and di-$C_1$-$C_6$-alkylamino; or unsubstituted naphthyl or quinolyl, or naphthyl or quinolyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_2$-$C_6$-alkenylthio, halo-$C_2$-$C_6$-alkenylthio, $C_2$-$C_6$-alkenylsulfinyl, halo-$C_2$-$C_6$-alkenylsulfinyl, $C_1$-$C_6$-alkylsulfonyl and halo-$C_1$-$C_6$-alkylsulfonyl, $C_2$-$C_6$-alkenylsulfonyl, halo-$C_2$-$C_6$-alkenylsulfonyl, $C_1$-$C_6$-alkylamino and di-$C_1$-$C_6$-alkylamino;

$Q_1$ signifies $CH_2$, $OCH_2$, S, S(O), $S(O_2)$ or C(O);

$Q_2$ signifies a direct bond or C(O);

$R_3$ signifies hydrogen, $C_1$-$C_6$-alkyl, halo-$C_1$-$C_6$-alkyl, cyano-$C_1$-$C_6$-alkyl, $C_1$-$C_6$-alkylthio, halo-$C_1$-$C_6$-alkylthio, $C_2$-$C_6$-alkenyl, $C_2$-$C_6$-alkinyl, benzyl or $C_1$-$C_6$-alkoxymethyl;

$R_4$, $R_5$, $R_6$, $R_7$ and $R_8$ either, independently of one another, signify hydrogen, halogen, $C_1$-$C_6$-alkyl, halo-$C_1$-$C_6$-alkyl, $C_3$-$C_6$-cycloalkyl that is either unsubstituted or substituted once or many times, whereby the substituents may be independent of one another and are selected from the group comprising halogen and $C_1$-$C_6$-alkyl; phenyl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino or di-$C_1$-$C_6$-alkylamino;

or $R_4$ and $R_5$ together signify $C_2$-$C_6$-alkylene;

W signifies O, S, $S(O_2)$ or $N(R_9)$;

$R_9$ signifies hydrogen or $C_1$-$C_6$-alkyl;

a signifies 1, 2, 3 or 4;

b signifies 0, 1, 2, 3 or 4; and n is 0 or 1.

Alkyl—as a group per se and as structural element of other groups and compounds such as halogen-alkyl, alkylamino, alkoxy, alkylthio, alkylsulfinyl and alkylsulfonyl—is, in each case with due consideration of the specific number of carbon atoms in the group or compound in question, either straight-chained, i.e. methyl, ethyl, propyl, butyl, pentyl, hexyl, heptyl or octyl, or branched, e.g. isopropyl, isobutyl, sec.-butyl, tert.-butyl, isopentyl, neopentyl or isohexyl.

Cycloalkyl—as a group per se and as structural element of other groups and compounds such as halocycloalkyl, cycloalkoxy and cycloalkylthio,—is, in each case with due consideration of the specific number of carbon atoms in the group or compound in question, cyclopropyl, cyclobutyl, cyclopentyl, cyclohexyl, cycloheptyl or cyclooctyl.

Alkenyl—as a group per se and as structural element of other groups and compounds—is, in each case with due consideration of the specific number of carbon atoms in the group or compound in question and of the conjugated or isolated double bonds—either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert.-pentenyl, isohexenyl, isoheptenyl or isooctenyl.

Alkinyl—as a group per se and as structural element of other groups and compounds—is, in each case with due consideration of the specific number of carbon atoms in the group or compound in question and of the conjugated or isolated double bonds—either straight-chained, e.g. propargyl, 2-butinyl, 3-pentinyl, 1-hexinyl, 1-heptinyl, 3-hexen-1-inyl or 1,5-heptadien-3-inyl, or branched, e.g. 3-methylbut-1-inyl, 4-ethylpent-1-inyl, 4-methylhex-2-inyl or 2-methylhept-3-inyl.

Heteroaryl is pyridyl, thienyl, furanyl, pyrryl, benzothienyl, benzofuranyl, indolyl or indazolyl, preferably pyridyl or thienyl, especially pyridyl.

As a rule, halogen signifies fluorine, chlorine, bromine or iodine. The same applies to halogen in combination with other significances, such as halogenalkyl or halogenphenyl.

Halogen-substituted carbon-containing groups and compounds may be partially halogenated or perhalogenated, whereby in the case of multiple halogenation, the halogen substituents may be identical or different. Examples of halogen-alkyl—as a group per se and as structural element of other groups and compounds such as halogen-alkoxy or halogen-alkylthio,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers substituted one to eleven times by fluorine, chlorine and/or bromine, such as $CF(CF_3)(CHF)_2CF_3$ or $CH_2(CF_2)_3CF_3$; and hexyl or one of its isomers substituted one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Halogenalkoxy groups preferably have a chain length of 1 to 6 carbon atoms. Halogenalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Preferred embodiments within the scope of the invention are:

(1) A compound of formula I, wherein $Ar_1$ and $Ar_2$, independently of one another, signify unsubstituted phenyl or phenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyl, halo-$C_2$-$C_6$-alkenyl, $C_2$-$C_6$-alkinyl, $C_3$-$C_6$-cycloalkyl, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylsulfonyloxy, halo-$C_1$-$C_6$-alkylsulfonyloxy, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_2$-$C_6$-alkenylthio, halo-$C_2$-$C_6$-alkenylthio, $C_2$-$C_6$-alkenylsulfinyl, halo-$C_2$-$C_6$-alkenylsulfinyl, $C_2$-$C_6$-alkenylsulfonyl, halo-$C_2$-$C_6$-alkenylsulfonyl, $C_1$-$C_6$-alkylamino, di-$C_1$-$C_6$-alkylamino, $C_1$-$C_6$-alkylsulfonylamino, halo-$C_1$-$C_6$-alkylsulfonylamino, $C_1$-$C_6$-alkylcarbonyl, halo-$C_1$-$C_6$-alkylcarbonyl, $C_1$-$C_6$-alkoxycarbonyl, $C_1$-$C_6$-alkylaminocarbonyl, di-$C_1$-$C_6$-alkylaminocarbonyl; unsubstituted phenyl or phenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl; unsubstituted phenoxy or phenoxy which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl; unsubstituted phenylacetylenyl or phenylacetylenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl; and unsubstituted pyridyloxy or pyridyloxy which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl and halo-$C_1$-$C_6$-alkylsulfonyl;

unsubstituted heteroaryl or heteroaryl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_2$-$C_6$-alkenylthio, halo-$C_2$-$C_6$-alkenylthio, $C_2$-$C_6$-alkenylsulfinyl, halo-$C_2$-$C_6$-alkenylsulfinyl, $C_1$-$C_6$-alkylsulfonyl and halo-$C_1$-$C_6$-alkylsulfonyl, $C_2$-$C_6$-alkenylsulfonyl, halo-$C_2$-$C_6$-alkenylsulfonyl, $C_1$-$C_6$-alkylamino and di-$C_1$-$C_6$-alkylamino; or unsubstituted naphthyl or quinolyl, or naphthyl or quinolyl which is substituted once or many times, whereby the substituents may be Independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_2$-$C_6$-alkenylthio, halo-$C_2$-$C_6$-alkenylthio, $C_2$-$C_6$-alkenylsulfinyl, halo-$C_2$-$C_6$-alkenylsulfinyl, $C_1$-$C_6$-alkylsulfonyl and halo-$C_1$-$C_6$-alkylsulfonyl, $C_2$-$C_6$-alkenylsulfonyl, halo-$C_2$-$C_6$-alkenylsulfonyl, $C_1$-$C_6$-alkylamino and di-$C_1$-$C_6$-alkylamino;

$Q_1$ signifies $CH_2$, $OCH_2$, S, S(O), $S(O_2)$ or C(O);

$Q_2$ signifies a direct bond or C(O);

$R_3$ signifies hydrogen, $C_1$-$C_6$-alkyl, halo-$C_1$-$C_6$-alkyl, cyano-$C_1$-$C_6$-alkyl, $C_1$-$C_6$-alkylthio, halo-$C_1$-$C_6$-alkylthio, $C_2$-$C_6$-alkenyl or $C_2$-$C_6$-alkinyl;

$R_4$, $R_5$, $R_6$, $R_7$ and $R_8$ either, independently of one another, signify hydrogen, halogen, $C_1$-$C_6$-alkyl, halo-$C_1$-$C_6$-alkyl, $C_3$-$C_6$-cycloalkyl that is either unsubstituted or substituted once or many times, whereby the substituents may be independent of one another and are selected from the group comprising halogen and $C_1$-$C_6$-alkyl; phenyl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino or di-$C_1$-$C_6$-alkylamino;

or $R_4$ and $R_5$ together signify $C_2$-$C_6$-alkylene;

W signifies O, S, $S(O_2)$ or $N(R_9)$;

$R_9$ signifies hydrogen or $C_1$-$C_6$-alkyl;

a signifies 1, 2, 3 or 4;

b signifies 0, 1, 2, 3 or 4; and n is 0 or 1;

(2) A compound of formula I, wherein $Ar_1$ and $Ar_2$, independently of one another, signify unsubstituted phenyl or phenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyl, halo-$C_2$-$C_6$-alkenyl, $C_2$-$C_6$-alkinyl, $C_3$-$C_6$-cycloalkyl, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylamino, di-$C_1$-$C_6$-alkylamino, $C_1$-$C_6$-alkylcarbonyl, halo-$C_1$-$C_6$-alkylcarbonyl, $C_1$-$C_6$-alkoxycarbonyl, $C_1$-$C_6$-alkylaminocarbonyl and di-$C_1$-$C_6$-alkylaminocarbonyl;

heteroaryl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylamino and di-$C_1$-$C_6$-alkylamino; or naphthyl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylamino and di-$C_1$-$C_6$-alkylamino;

especially phenyl that is, independently of one another, either unsubstituted or substituted once or many times, whereby the substituents may be independent of one another and are selected from the group comprising halogen, $C_1$-$C_6$-alkyl, halo-$C_1$-$C_6$-alkyl, $C_1$-$C_6$-alkoxy, halo-$C_1$-$C_6$-alkoxy, $C_3$-$C_6$-cycloalkyl, $C_1$-$C_6$-alkylthio, halo-$C_1$-$C_6$-alkylthio, $C_1$-$C_6$-alkylcarbonyl, halo-$C_1$-$C_6$-alkylcarbonyl, $C_1$-$C_6$-alkoxycarbonyl, $C_1$-$C_6$-alkylaminocarbonyl and di-$C_1$-$C_6$-alkylaminocarbonyl;

heteroaryl that is either unsubstituted or substituted once or many times, whereby the substituents may be independent of one another and are selected from the group comprising halogen, $C_1$-$C_6$-alkyl, halo-$C_{1-6}$-alkyl, $C_1$-$C_6$-alkoxy, halo-$C_1$-$C_6$-alkoxy, $C_1$-$C_6$-alkylamino and di-$C_1$-$C_6$-alkylamino; or naphthyl that is either unsubstituted or substituted once or many times, whereby the substituents may be independent of one another and are selected from the group comprising halogen, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylamino and di-$C_1$-$C_6$-alkylamino;

most particularly phenyl that is, independently of one another, either unsubstituted or substituted once or many times, whereby the substituents may be independent of one another and are selected from the group comprising halogen, $C_1$-$C_6$-alkyl, halo-$C_1$-$C_6$-alkyl, $C_1$-$C_6$-alkoxy and halo-$C_1$-$C_6$-alkoxy; or heteroaryl that is either unsubstituted or substituted once or many times, whereby the substituents may be independent of one another and are selected from the group comprising halogen, $C_1$-$C_6$-alkyl and halo-$C_1$-$C_6$-alkyl;

(3) A compound of formula I, wherein $Q_1$ is $CH_2$, S, $S(O_2)$ or C(O); especially C(O);

(4) A compound of formula I, wherein $R_3$ signifies hydrogen, $C_1$-$C_6$-alkyl, halo-$C_1$-$C_6$-alkyl, cyano-$C_1$-$C_6$-alkyl, $C_1$-$C_6$-alkylthio, halo-$C_1$-$C_6$-alkylthio, $C_2$-$C_6$-alkenyl or $C_2$-$C_6$-alkinyl;

especially hydrogen or $C_1$-$C_6$-alkyl;

most particularly hydrogen;

(5) A compound of formula I, wherein $R_4$, $R_5$, $R_6$, $R_7$ and $R_8$, independently of one another, are hydrogen, halogen, $C_1$-$C_6$-alkyl, halo-$C_1$-$C_6$-alkyl, $C_3$-$C_6$-Cycloalkyl; phenyl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy and halo-$C_1$-$C_6$-alkoxy;

especially, independently of one another, hydrogen, halogen, $C_1$-$C_6$-alkyl, halo-$C_1$-$C_6$-alkyl or $C_3$-$C_6$-cycloalkyl;

especially, independently of one another, hydrogen, halogen, $C_1$-$C_6$-alkyl or halo-$C_1$-$C_6$-alkyl;

(6) A compound of formula I, wherein W is O, S or $N(R_9)$;

especially O or $N(R_9)$;

particularly O;

(7) A compound of formula I, wherein $R_9$ signifies hydrogen or $C_1$—$R_4$-alkyl;

especially hydrogen or $C_1$-$C_2$-alkyl;

particularly methyl;

(8) A compound of formula I, wherein a is 1, 2 or 4;

especially 1 or 4;

particularly 1;

(9) A compound of formula I, wherein b is 0, 1, 2 or 4;

especially 0, 1 or 4;

particularly 0 or 1;

(10) A compound of formula I, wherein n is 0;

(11) A compound of formula I, wherein $Ar_1$ and $Ar_2$, independently of one another, signify unsubstituted phenyl or phenyl which is substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyl, halo-$C_2$-$C_6$-alkenyl, $C_2$-$C_6$-alkinyl, $C_3$-$C_6$-cycloalkyl, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylamino, di-$C_1$-$C_6$-alkylamino, $C_1$-$C_6$-alkylcarbonyl, halo-$C_1$-$C_6$-alkylcarbonyl, $C_1$-$C_6$-alkoxycarbonyl, $C_1$-$C_6$-alkylaminocarbonyl and di-$C_1$-$C_6$-alkylaminocarbonyl;

heteroaryl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylamino and di-$C_1$-$C_6$-alkylamino; or naphthyl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylamino and di-$C_1$-$C_6$-alkylamino;

$Q_1$ signifies $CH_2$, S, $S(O_2)$ or C(O);

$R_3$ signifies hydrogen or $C_1$-$C_6$-alkyl;

$R_4$, $R_5$, $R_6$, $R_7$ and $R_8$, independently of one another, are hydrogen, halogen, $C_1$-$C_6$-alkyl, halo-$C_1$-$C_6$-alkyl, $C_3$-$C_6$-Cycloalkyl; phenyl that is either unsubstituted or substituted once or many times, whereby the substituents may be independent of one another and are selected from the group comprising halogen, nitro, cyano, $C_1$-$C_6$-alkyl, halo-$C_1$-$C_6$-alkyl, $C_1$-$C_6$-alkoxy and halo-$C_1$-$C_6$-alkoxy;

W signifies O, S or $N(R_9)$;

$R_9$ signifies hydrogen or $C_1$-$C_4$-alkyl;

a signifies 1, 2 or 4;

b signifies 0, 1, 2 or 4; and n signifies 0;

(12) A compound of formula I, wherein $Ar_1$ and $Ar_2$, independently of one another, signify phenyl that is either unsubstituted or substituted once or many times, whereby the substituents may be independent of one another and are selected from the group comprising halogen, $C_1$-$C_6$-alkyl, halo-$C_1$-$C_6$-alkyl, $C_1$-$C_6$-alkoxy, halo-$C_1$-$C_6$-alkoxy, $C_3$-$C_6$-cycloalkyl, $C_1$-$C_6$-alkylthio, halo-$C_1$-$C_6$-alkylthio, $C_1$-$C_6$-alkylcarbonyl, halo-$C_1$-$C_6$-alkylcarbonyl, $C_1$-$C_6$-alkoxycarbonyl, $C_1$-$C_6$-alkylaminocarbonyl and di-$C_1$-$C_6$-alkylaminocarbonyl;

$Q_1$ signifies C(O);

$R_3$ signifies hydrogen or $C_1$-$C_2$-alkyl;

$R_4$, $R_5$, $R_6$, $R_7$ and $R_8$, independently of one another, signify hydrogen, halogen, $C_1$-$C_6$-alkyl, halo-$C_1$-$C_6$-alkyl or $C_3$-$C_6$-cycloalkyl;

W signifies O or $N(R_9)$;

$R_9$ signifies hydrogen or $C_1$-$C_2$-alkyl;

a signifies 1 or 4;

b signifies 0, 1 or 4; and n signifies 0;

(13) A compound of formula I, wherein $Ar_1$ and $Ar_2$, independently of one another, signify phenyl that is either unsubstituted or substituted once or many times, whereby the substituents may be independent of one another and are selected from the group comprising halogen, $C_1$-$C_6$-alkyl, halo-$C_1$-$C_6$-alkyl, $C_1$-$C_6$-alkoxy and halo-$C_1$-$C_6$-alkoxy; or heteroaryl that is either unsubstituted or substituted once or many times, whereby the substituents may be independent of one another and are selected from the group comprising halogen, $C_1$-$C_6$-alkyl and halo-$C_1$-$C_6$-alkyl;

$Q_1$ signifies C(O);

$R_3$ signifies hydrogen;

$R_4$, $R_5$, $R_6$, $R_7$ and $R_8$, independently of one another, signify hydrogen, halogen, $C_1$-$C_6$-alkyl or halo-$C_1$-$C_6$-alkyl;

W signifies O;

$R_9$ signifies methyl;

a signifies 1;

b signifies 0 or 1; and n is O.

Within the context of the invention, particular preference is given to the compounds of formula I listed in Table 1, and most particularly those named in the synthesis examples.

A further object of the invention is the process for the preparation of the compounds of formula I, respectively in free form or in salt form, for example characterised in that a compound of formula

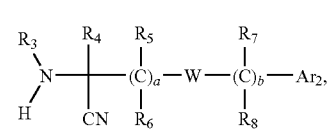

II which is known or may be produced analogously to corresponding known compounds, and wherein $R_3$, $R_4$, $R_5$, $R_6$, $R_7$, $R_8$, W, $Ar_2$, a and b are defined as given for formula I, is reacted with a compound of formula

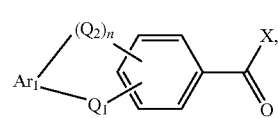

III which is known or may be prepared analogously to corresponding known compounds, and wherein $Ar_1$, $Q_1$, $Q_2$ and n are defined as given for formula I and X is a leaving group, optionally in the presence of a basic catalyst, and if desired, a compound of formula I obtained according to the method or in another way, respectively in free form or in salt form, is converted into another compound of formula I, a mixture of isomers which is obtainable by this process is separated and the desired isomer isolated and/or a free compound of formula I obtained according to the method is converted into a salt or a salt of a compound of formula I obtained according to the method is converted into the free compound of formula I or into another salt.

What has been stated above for salts of compounds I also applies analogously to salts of the starting materials listed hereinabove and hereinbelow.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitriles such as acetonitrile or propionitrile; and sulfoxides, such as dimethyl sulfoxide.

Preferred leaving groups are OH, halogens, tosylates, mesylates and triflates, most preferably halogens, especially chlorine.

Suitable bases for facilitating the reaction are e.g. alkali metal or alkaline earth metal hydroxides, hydrides, amides, alkanolates, acetates, carbonates, dialkylamides or alkylsilylamides; alkylamines, alkylenediamines, optionally N-alkylated, optionally unsaturated, cycloalkylamines, basic heterocycles, ammonium hydroxides, as well as carbocyclic amines. Those which may be mentioned by way of example are sodium hydroxide, hydride, amide, methanolate, acetate, carbonate, potassium tert.-butanolate, hydroxide, carbonate, hydride, lithium diisopropylamide, potassium bis(trimethylsilyl)-amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU).

The reaction advantageously takes place in a temperature range of ca. 0° C. to ca. 150° C., preferably from ca. 20° C. to ca. 100° C.

Salts of compounds I may be produced in known manner. Acid addition salts, for example, are obtainable from compounds I by treating with a suitable acid or a suitable ion exchange reagent, and salts with bases are obtainable by treating with a suitable base or a suitable ion exchange reagent Salts of compounds I can be converted into the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds I can be converted into other salts of compounds I in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds I with salt-forming characteristics can be obtained in free form or in the form of salts.

Compounds I can also be obtained in the form of their hydrates and/or also can include other solvents, used for example where necessary for the crystallisation of compounds present in solid form.

The compounds I and II may be present in the form of one of the possible isomers or as a mixture thereof, depending for example on the number and the absolute and relative configuration of the asymmetric carbon atoms, as pure isomers, such as antipodes and/or diastereoisomers, or as isomeric mixtures, such as a mixture of enantiomers, for example racemates, diastereoisomeric mixtures or racemate mixtures; the invention relates both to the pure isomers and to all possible isomeric mixtures, and is hereinbefore and hereinafter understood as doing so, even if stereochemical details are not specifically mentioned in every case.

Depending on the choice of starting materials and methods, diastereoisomeric mixtures and racemate mixtures of compounds I and II, which are obtainable by the process or in another way, may be separated in known manner, on the basis of the physical-chemical differences in their components, into the pure diastereoisomers or racemates, for example by fractional crystallisation, distillation and/or chromatography.

Resolution of mixtures of enantiomers that are obtainable accordingly, such as racemates, may be achieved by known methods, for example by recrystallisation from an optically active solvent, by chromatography on chiral adsorbents, e.g. high-pressure liquid chromatography (HPLC) on acetyl cellulose, with the assistance of appropriate microorganisms, by cleavage with specific immobilised enzymes, through the formation of inclusion compounds, e.g. using chiral crown ethers, whereby only one enantiomer is complexed.

According to the invention, apart from isolation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesise the biologically more active isomer, e.g. enantiomer, or isomer mixture, e.g. enantiomer mixture, provided that the individual components have differing biological efficacy.

In the method of the present invention, the starting materials and intermediates used are preferably those that lead to the compounds I described at the beginning as being especially useful.

The invention relates especially to the method of preparation described in the example.

Starting materials and intermediates, which are new and are used according to the invention for the preparation of compounds I, as well as their usage and process for the preparation thereof, similarly form an object of the invention.

The compounds I according to the invention are notable for their broad activity spectrum and are valuable active ingredients for use in pest control, including in particular the control of endo- and ecto-parasites on animals, whilst being well-tolerated by warm-blooded animals, fish and plants, In the context of the present invention, ectoparasites are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia caniculadis, Sarcophaga carnadia, Lucilla cuprina, Hypoderma bovis, Hypoderma lineatum, Chrysomyia chloropyga, Dermatobia hominis, Cochliomyia hominivorax, Gasterophilus intestinalls, Oestrus ovis, Stomoxys calcitrans, Haematobia irritans* and midges (*Nematocera*), such as *Culicidae, Simullidae, Psychodidae*, but also blood-sucking parasites, for example fleas, such as *Ctenocephalides felis* and *Ctenocephalides canis* (cat and dog fleas), *Xenopsylla cheopis, Pulex irritans, Dermatophilus penetrans*, lice, such as *Damalina ovis, Pediculus humanis*, biting flies and horse-flies (*Tabanidae*), *Haematopota* spp. such as *Haematopota pluvialis, Tabanidea* spp. such as *Tabanus nigrovittatus, Chrysopsinae* spp. such as *Chrysops caecutiens*, tsetse flies, such as species of *Glossinia*, biting insects, particularly cockroaches, such as *Blatella germanica, Blatta orientalis, Periplaneta americana*, mites, such as *Dermanyssus gallinae, Sarcoptes scabiel, Psoroptes ovis* and *Psorergates* spp. and last but not least ticks. The latter belong to the order Acarina. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

The compounds I according to the invention are also active against all or individual development stages of animal pests showing normal sensitivity, as well as those showing resistance, such as insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds I can also be used against hygiene pests, especially of the order Diptera of the families Sarcophagidae, Anophilidae and Culicidae; the orders Orthoptera, Dictyoptera (e.g. the family Blattidae) and Hymenoptera (e.g. the family Formicidae).

Compounds I also have sustainable efficacy on parasitic mites and insects of plants. In the case of spider mites of the order Acarina, they are effective against eggs, nymphs and adults of Tetranychidae (*Tetranychus* spp. and *Panonychus* spp.).

They have high activity against sucking insects of the order Homoptera, especially against pests of the families Aphididae, Delphacidae, Cicadellidae, Psyllidae, Loccidae, Diaspididae and Eriophydidae (e.g. rust mite on citrus fruits); the orders Hemiptera, Heteroptera and Thysanoptera, and on the plant-eating insects of the orders Lepidoptera, Coleoptera, Diptera and Orthoptera They are similarly suitable as a soil insecticide against pests in the soil.

The compounds of formula I are therefore effective against all stages of development of sucking insects and eating insects on crops such as cereals, cotton, rice, maize, soya, potatoes, vegetables, fruit, tobacco, hops, citrus, avocados and other crops.

The compounds of formula I are also effective against plant nematodes of the species *Meloidogyne, Heterodera, Pratylenchus, Ditylenchus, Radopholus, Rizoglyphus* etc.

In particular, the compounds are effective against helminths, in which the endoparasitic nematodes and trematodes may be the cause of serious diseases of mammals and poultry, e.g. sheep, pigs, goats, cattle, horses, donkeys, dogs, cats, guinea-pigs and exotic birds. Typical nematodes of this indication are: *Haemonchus, Trichostrongylus, Ostertagia, Nematodirus, Coopedia, Ascaris, Bunostonum, Oesophagostonum, Charbertia, Trichuris, Strongylus, Trichonema, Dictyocaulus, Capilladia, Heterakis, Toxocara, Ascaridia, Oxyuris, Ancylostoma, Uncinaria, Toxascadis* and *Parascaris*. The trematodes include, in particular, the family of Fasclolideae, especially *Fasciola hepatica*. The particular advantage of the compounds of formula I is their efficacy against those parasites that are resistant towards active ingredients based on benzimidazole.

Certain pests of the species *Nematodirus, Coopeda* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families Filariidae and Setariidae may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula I are highly effective against these parasites.

The pests which may be controlled by the compounds of formula I also include those from the class of Cestoda (tapeworms), e.g. the families Mesocestoidae, especially of the genus *Mesocestoides*, in particular *M. lineatus; Dilepidide*, especially *Dipylidium caninum, Joyeuxiella* spp., in particular *Joyeuxiella pasquali*, and *Diplopylidium* spp., and *Taeniidae*, especially *Taenia pisiformis, Taenia cervi, Taenia ovis, Taneia hydatigena, Taenia multiceps, Taenia taeniaeformis, Taenla sedalis*, and *Echinocuccus* spp., most preferably *Taneia hydatigena, Taenia ovis, Taenia multiceps, Taenia serialis; Echinocuccus granulosus* and *Echinococcus granulosus* and *Echinococcus multiloculatis*, as well as *Multiceps multiceps*.

Most particularly, *Taenia hydatigena, T. pisiformis, T. ovis, T. taeniaeformis, Multiceps multiceps, Joyeuxiella pasquali, Dipylidium caninum, Mesocestoides* spp., *Echinococcus granulosus* and *E. multiloculais* are controlled on or in dogs and cats simultaneously with *Dirofilaria immitis, Ancylostoma* ssp., *Toxocara* ssp. and/or *Trichuris vulpis*. Equally preferred, *Ctenocephalides felis* and/or *C. canis* are simultaneously controlled with the above-mentioned nematodes and cestodes.

Furthermore, the compounds of formula I are suitable for the control of human pathogenic parasites. Of these, typical representatives that appear in the digestive tract are those of the species *Ancylostoma, Necator, Ascaris, Strongyloides, Trichinella, Capillaria, Trichuris* and *Enterobius*. The compounds of the present invention are also effective against parasites of the species *Wuchereria, Brugia, Onchocerca* and *Loa* from the family of Filariidae, which appear in the blood, in the tissue and in various organs, and also against *Dracunculus* and parasites of the species *Strongyloides* and *Trichinella*, which infect the gastrointestinal tract in particular.

In addition, the compounds of formula I are also effective against harmful and pathogenic fungi on plants, as well as on humans and animals.

The good pesticidal activity of the compounds of formula I according to the invention corresponds to a mortality rate of at least 50-60% of the pests mentioned. In particular, the compounds of formula I are notable for the exceptionally long duration of efficacy.

The compounds of formula I are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula I, or combinations of these active ingredients with other active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boli, capsules, micro-capsules and pour-on formulations, whereby the physiological compatibility of the formulation excipients must be taken into consideration.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02.% by weight (5-200 ppm).

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stage of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers.

Non-limitative examples of suitable insecticides and acaricides are:

1. Abamectin
2. AC 303 630
3. Acephat
4. Acrinathrin
5. Alanycarb
6. Aldicarb
7. α-Cypermethrin
8. Alphamethrin
9. Amitraz
10. Avermectin $B_1$
11. AZ 60541
12. Azinphos A
13. Azinphos M
14. Azinphos-methyl
15. Azocyclotin
16. *Bacillus* subtil. toxin
17. Bendiocarb
18. Benfuracarb
19. Bensultap
20. β-Cyfluthrin
21. Bifenthrin
22. BPMC
23. Brofenprox
24. Bromophos A
25. Bufencarb
26. Buprofezin
27. Butocarboxin
28. Butylpyridaben
29. Cadusafos
30. Carbaryl
31. Carbofuran
32. Carbophenthion
33. Cartap
34. Chloethocarb
35. Chlorethoxyfos
36. Chlorfenapyr
37. Chlorfluazuron
38. Chlormephos
39. Chlorpyrifos
40. Cis-Resmethrin
41. Clocythrin
42. Clofentezin
43. Cyanophos
44. Cycloprothrin
45. Cyfluthrin -continued 46. Cyhexatin
47. D 2341
48. Deltamethrin
49. Demeton M
50. Demeton S
51. Demeton-S-methyl
52. Dibutylaminothio
53. Dichlofenthion
54. Dicliphos
55. Diethion
56. Diflubenzuron
57. Dimethoat
58. Dimethylvinphos
59. Dioxathion
60. DPX-MP062
61. Edifenphos
62. Emamectin
63. Endosulfan
64. Esfenvalerat
65. Ethiofencarb
66. Ethion
67. Ethofenprox
68. Ethoprophos
69. Etrimphos
70. Fenamiphos
71. Fenazaquin
72. Fenbutatinoxid
73. Fenitrothion
74. Fenobucarb
75. Fenothiocarb
76. Fenoxycarb
77. Fenpropathrin
78. Fenpyrad
79. Fenpyroximate
80. Fenthion
81. Fenvalerate
82. Fipronil
83. Fluazinam
84. Fluazuron
85. Flucycloxuron
86. Flucythrinat
87. Flufenoxuron
88. Flufenprox
89. Fonophos
90. Formothion
91. Fosthiazat
92. Fubfenprox
93. HCH
94. Heptenophos
95. Hexaflumuron
96. Hexythiazox
97. Hydroprene
98. Imidacloprid
99. insect-active fungi
100. insect-active nematodes
101. insect-active viruses
102. Iprobenfos
103. Isofenphos
104. Isoprocarb
105. Isoxathion
106. Ivermectin
107. λ-Cyhalothrin
108. Lufenuron
109. Malathion
110. Mecarbam
111. Mesulfenphos
112. Metaldehyd
113. Methamidophos
114. Methiocarb
115. Methomyl
116. Methoprene
117. Metolcarb
118. Mevinphos
119. Milbemectin
120. Moxidectin
121. Naled
122. NC 184
123. NI-25, Acetamiprid
124. Nitenpyram
125. Omethoat
126. Oxamyl
127. Oxydemethon M
128. Oxydeprofos
129. Parathion
130. Parathion-methyl
131. Permethrin
132. Phenthoat
133. Phorat
134. Phosalone
135. Phosmet
136. Phoxim
137. Pirimicarb
138. Pirimiphos A
139. Pirimiphos M
140. Promecarb
141. Propaphos
142. Propoxur
143. Prothiofos
144. Prothoat
145. Pyrachlophos
146. Pyradaphenthion
147. Pyresmethrin
148. Pyrethrum
149. Pyridaben
150. Pyrimidifen
151. Pyriproxyfen
152. RH 5992
153. RH-2485
154. Salithion
155. Sebufos
156. Silafluofen
157. Spinosad
158. Sulfotep
159. Sulprofos
160. Tebufenozide
161. Tebufenpyrad
162. Tebupirimphos
163. Teflubenzuron
164. Tefluthrin
165. Temephos
166. Terbam
167. Terbufos
168. Tetrachlorvinphos
169. Thiafenox
170. Thiodicarb
171. Thiofanox
172. Thionazin
173. Thuringiensin
174. Tralomethrin
175. Triarthen
176. Triazamate
177. Triazophos
178. Triazuron
179. Trichlorfon
180. Triflumuron
181. Trimethacarb
182. Vamidothion
183. XMC (3,5,-Xylyl-methylcarbamate)
184. Xylylcarb
185. YI 5301/5302
186. ζ-Cypermethrin
187. Zetamethrin Non-limiting examples of suitable anthelminthics are named in the following, a few representatives have insecticidal and acaricidal activity in addition to the anthelminthic activity, and are partly already in the above list.

(A1) Praziquantel=2-cyclohexylcarbonyl-4-oxo-1,2,3,6,7,11b-hexahydro-4H-pyrazino[2,1-α]isoquinoline (A2) Closantel=3,5-diiodo-N-[5-chloro-2-methyl-4-(α-cyano-4-chlorobenzyl)phenyl]-salicylamide (A3) Triclabendazole=5-chloro-6-(2,3-dichlorophenoxy)-2-methylthio-1H-benzimidazole (A4) Levamisol=L-(−)-2,3,5,6-tetrahydro-6-phenylimidazo[2,1b]thiazole
(A5) Mebendazole=(5-benzoyl-1H-benzimidazol-2-yl)carbaminic acid methylester
(A6) Omphalotin=a macrocyclic fermentation product of the fungus *Omphalotus olearius* described In WO 97/20857
(A7) Abamectin=avermectin B1
(A8) Ivermectin=22,23-dihydroavermectin B1
(A9) Moxidectin=5-O-demethyl-28-deoxy-25-(1,3-dimethyl-1-butenyl)-6,28-epoxy-23-(methoxyimino)-milbemycin B
(A10) Doramectin=25-cyclohexyl-5-O-demethyl-25-de(1-methylpropyl)-avermectin A1a
(A11) Milbemectin=mixture of milbemycin A3 and milbemycin A4
(A12) Milbemycinoxim=5-oxime of milbemectin Non-limitative examples of suitable repellents and detachers are:
(R₁) DEET (N,N-diethyl-m-toluamide)
(R₂) KBR 3023 N-butyl-2-oxycarbonyl-(2-hydroxy)-piperidine
(R₃) Cymiazole=N,-2,3-dihydro-3-methyl-1,3-thiazol-2-ylidene-2,4-xylidene The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.

(I) 2-Methyl-2-(methylthio)propionaldehyde-O-methylcarbamoyloxime (Aldicarb), from The Pesticide Manual, 11$^{th}$ Ed. (1997), The British Crop Protection Council, London, page 26;
(II) S-(3,4-dihydro-4-oxobenzo[d]-[1,2,3]-triazin-3-ylmethyl)O,O-dimethyl-phosphorodithioate (Azinphos-methyl), from The Pesticide Manual, 11$^{th}$Ed. (1997), The British Crop Protection Council, London, page 67;
(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, 11$^{th}$Ed. (1997), The British Crop Protection Council, London, page 96;
(IV) 2-Methylbiphenyl-3-ylmethyl-(Z)-(1RS)-cis-3-(2-chloro-3,3,3-trifluoroprop-1-enyl)-2,2-dimethylcyclopropanecarboxylate (Bifenthrin), from The Pesticide Manual, 11$^{th}$Ed. (1997), The British Crop Protection Council, London, page 118;
(V) 2-tert-butylimino-3-isopropyl-5-phenyl-1,3,5-thiadiazian-4-one (Buprofezin), from The Pesticide Manual, 11$^{th}$Ed. (1997), The British Crop Protection Council, London, page 157;
(VI) 2,3-Dihydro-2,2-dimethylbenzofuran-7-yl-methylcarbamate (Carbofuran), from The Pesticide Manual, 11$^{th}$Ed. (1997), The British Crop Protection Council, London, page 186;
(VII) 2,3-Dihydro-2,2-dimethylbenzofuran-7-yl-(dibutylaminothio)methylcarbamate (Carbosulfan), from The Pesticide Manual, 11$^{th}$Ed. (1997), The British Crop Protection Council, London, page 188;
(VIII) S,S'-(2-dimethylaminotrimethylene)-bis(thiocarbamate) (Cartap), from The Pesticide Manual, 11$^{th}$Ed. (1997), The British Crop Protection Council, London, page 193;
(IX) 1-[3,5-Dichloro-4-(3-chloro-5-trifluoromethyl-2-pyridyloxy)phenyl]-3-(2,6-difluorobenzoyl)-urea (Chlorfluazuron), from The Pesticide Manual, 11$^{th}$Ed. (1997), The British Crop Protection Council, London, page 213;
(X) O,O-diethyl-O-3,5,6-trichloro-2-pyridyl-phosphorothioate (Chlorpyrifos), from The Pesticide Manual, 11$^{th}$Ed. (1997), The British Crop Protection Council, London, page 235;
(XI) (RS)-α-cyano-4-fluoro-3-phenoxybenzyl-(1RS,3RS;1RS,3RS)-3-(2,2-dichlorovinyl)-2,2-di-methylcyclopropanecarboxylate (Cyfluthrin), from The Pesticide Manual, 11$^{th}$Ed. (1997), The British Crop Protection Council, London, page 293;
(XII) Mixture of (S)-α-cyano-3-phenoxybenzyl-(Z)-(1R,3R)-3-(2-chloro-3,3,3-trifluoropropenyl)-2,2-dimethylcyclopropanecarboxylate and (R)-α-cyano-3-phenoxybenzyl-(Z)-(1R,3R)-3-(2-chloro-3,3,3-trifluoropropenyl)-2,2-dimethylcyclopropanecarboxylate (Lambda-Cyhalothrin), from The Pesticide Manual, 11$^{th}$Ed. (1997), The British Crop Protection Council, London, page 300;
(XIII) Racemate consisting of (S)-α-cyano-3-phenoxybenzyl-(2)-(1R,3R)-3-(2,2-dichlorovinyl)-2,2-dimethylcyclopropanecarboxylate and (R)-α-cyano-3-phenoxybenzyl-(1S,3S)-3-(2,2-dichlorovinyl)-2,2-dimethylcyclopropanecarboxylate (Alpha-cypermethrin), from The Pesticide Manual, 11$^{th}$Ed. (1997), The British Crop Protection Council, London, page 308;
(XIV) a mixture of the stereoisomers of (S)-α-cyano-3-phenoxybenzyl (1RS,3RS,1 RS,3RS)-3-(2,2-dichlorovinyl)-2,2-dimethylcyclopropanecarboxylate (zeta-Cypermethrin), from The Pesticide Manual, 11$^{th}$Ed. (1997), The British Crop Protection Council, London, page 314;
(XV) (S)-α-cyano-3-phenoxybenzyl-(1R,3R)-3-(2,2-dibromovinyl)-2,2-dimethylcyclopropanecarboxylate (Deltamethrin), from The Pesticide Manual, 11$^{th}$Ed. (1997), The British Crop Protection Council, London, page 344;
(XVI) (4-chlorophenyl)-3-(2,6-difluorobenzoyl)urea (Diflubenzuron), from The Pesticide Manual, 11$^{th}$Ed. (1997), The British Crop Protection Council, London, page 395;
(XVII) (1,4,5,6,7,7-Hexachloro-8,9,10-trinorborn-5-en-2,3-ylenebismethylene)-sulphite (Endosulfan), from The Pesticide Manual, 11$^{th}$Ed. (1997), The British Crop Protection Council, London, page 459;
(XVIII) α-ethylthio-o-tolyl-methylcarbamate (Ethiofencarb), from The Pesticide Manual, 11$^{th}$Ed. (1997), The British Crop Protection Council, London, page 479;
(XIX) O,O-dimethyl-O-4-nitro-m-tolyl-phosphorothioate (Fenitrothion), from The Pesticide Manual, 11$^{th}$Ed. (1997), The British Crop Protection Council, London, page 514;
(XX) 2-sec-butylphenyl-methylcarbamate (Fenobucarb), from The Pesticide Manual, 11$^{th}$Ed. (1997), The British Crop Protection Council, London, page 516;
(XXI) (RS)-α-cyano-3-phenoxybenzyl-(RS)-2-(4-chlorophenyl)-3-methylbutyrate (Fenvalerate), from The Pesticide Manual, 11$^{th}$Ed. (1997), The British Crop Protection Council, London, page 539;
(XXII) S-[formyl(methyl)carbamoylmethyl]-O,O-dimethylphosphorodithioate (Formothion), from The Pesticide Manual, 11$^{th}$Ed. (1997), The British Crop Protection Council, London, page 625;
(XXIII) 4-Methylthio-3,5-xylyl-methylcarbamate (Methiocarb), from The Pesticide Manual, 11$^{th}$Ed. (1997), The British Crop Protection Council, London, page 813;
(XXIV) 7-Chlorobicyclo[3.2.0]hepta-2,6-dien-6-yl-dimethylphosphate (Heptenophos), from The Pesticide Manual, 11$^{th}$Ed. (1997), The British Crop Protection Council, London, page 670;

(XXV) 1-(6-chloro-3-pyridylmethyl)-N-nitroimidazolidin-2-ylidenamine (Imidacloprid), from The Pesticide Manual, 11th Ed. (1997), The British Crop Protection Council, London, page 706;

(XXVI) 2-isopropylphenyl-methylcarbamate (Isoprocarb), from The Pesticide Manual, 11th Ed. (1997), The British Crop Protection Council, London, page 729;

(XXVII) O,S-dimethyl-phosphoramidothioate (Methamidophos), from The Pesticide Manual, 11th Ed. (1997), The British Crop Protection Council, London, page 808;

(XXVIII) S-Methyl-N-(methylcarbamoyloxy)thioacetimidate (Methomyl), from The Pesticide Manual, 11th Ed. (1997), The British Crop Protection Council, London, page 815;

(XXIX) Methyl-3-(dimethoxyphosphinoyloxy)but-2-enoate (Mevinphos), from The Pesticide Manual, 11th Ed. (1997), The British Crop Protection Council, London, page 844;

(XXX) O,O-diethyl-O-4-nitrophenyl-phosphorothioate (Parathion), from The Pesticide Manual, 11th Ed. (1997), The British Crop Protection Council, London, page 926;

(XXXI) O,O-dimethyl-O-4-nitrophenyl-phosphorothioate (Parathion-methyl), from The Pesticide Manual, 11th Ed. (1997), The British Crop Protection Council, London, page 928;

(XXXII) S-6-chloro-2,3-dihydro-2-oxo-1,3-benzoxazol-3-ylmethyl-O,O-diethyl-phosphordithioate (Phosalone), from The Pesticide Manual, 11th Ed. (1997), The British Crop Protection Council, London, page 963;

(XXXIII) 2-Dimethylamino-5,6-dimethylpyrimidin-4-yl-dimethylcarbamate (Pirimicarb), from The Pesticide Manual, 11th Ed. (1997), The British Crop Protection Council, London, page 985;

(XXXIV) 2-isopropoxyphenyl-methylcarbamate (Propoxur), from The Pesticide Manual, 11th Ed. (1997), The British Crop Protection Council, London, page 1036;

(XXXV) 1-(3,5-dichloro-2,4-difluorophenyl)-3-(2,6-difluorobenzoyl)urea (Teflubenzuron), from The Pesticide Manual, 11th Ed. (1997), The British Crop Protection Council, London, page 1158;

(XXXVI) S-tert-butylthiomethyl-O,O-dimethyl-phosphorodithioate (Terbufos), from The Pesticide Manual, 11th Ed. (1997), The British Crop Protection Council, London, page 1165;

(XXXVII) ethyl-(3-tert.-butyl-1-dimethylcarbamoyl-1H-1,2,4-triazol-5-yl-thio)-acetate, (Triazamate), from The Pesticide Manual, 11th Ed. (1997), The British Crop Protection Council, London, page 1224;

(XXXVIII) Abamectin, from The Pesticide Manual, 11th Ed. (1997), The British Crop Protection Council, London, page 3;

(XXXIX) 2-sec-butylphenyl-methylcarbamate (Fenobucarb), from The Pesticide Manual, 11th Ed. (1997), The British Crop Protection Council, London, page 516;

(XL) N-tert.-butyl-N'-(4-ethylbenzoyl)-3,5-dimethylbenzohydrazide (Tebufenozide), from The Pesticide Manual, 11th Ed. (1997), The British Crop Protection Council, London, page 1147;

(XLI) (±)-5-amino-1-(2,6-dichloro-α,α,α-trifluoro-p-tolyl)-4-trifluoromethyl-sulphinylpyrazol-3-carbonitrile (Fipronil), from The Pesticide Manual, 11th Ed. (1997), The British Crop Protection Council, London, page 545;

(XLII) (RS)-α-cyano-4-fluoro-3-phenoxybenzyl(1RS,3RS; 1 RS,3RS)-3-(2,2-dichlorovinyl)-2,2-dimethylcyclopropanecarboxylate (beta-Cyfluthrin), from The Pesticide Manual, 11th Ed. (1997), The British Crop Protection Council, London, page 295;

(XLIII) (4-ethoxyphenyl)-[3-(4-fluoro-3-phenoxyphenyl)propyl](dimethyl)silane (Silafluofen), from The Pesticide Manual, 11th Ed. (1997), The British Crop Protection Council, London, page 1105;

(XLIV) tert.-butyl (E)-α-(1,3-dimethyl-5-phenoxypyrazol-4-yl-methylenamino-oxy)-p-toluate (Fenpyroximate), from The Pesticide Manual, 11th Ed. (1997), The British Crop Protection Council, London, page 530;

(XLV) 2-tert.-butyl-5-(4-tert.-butylbenzylthio)-4-chloropyridazin-3(2H)-one (Pyridaben), from The Pesticide Manual, 11th Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11th Ed. (1997), The British Crop Protection Council, London, page 507;

(XLVII) 4-phenoxyphenyl-(RS)-2-(pyridyloxy)propyl-ether (Pyriproxyfen), from The Pesticide Manual, 11th Ed. (1997), The British Crop Protection Council, London, page 1073;

(XLVIII) 5-chloro-N-{2-[4-(2-ethoxyethyl)-2,3-dimethylphenoxy]ethyl}-6-ethylpyrimidine-4-amine (Pyrimidifen), from The Pesticide Manual, 11th Ed. (1997), The British Crop Protection Council, London, page 1070;

(XLIX) (E)-N-(6-chloro-3-pyridylmethyl)-N-ethyl-N'-methyl-2-nitrovinylidenediamine (Nitenpyram), from The Pesticide Manual, 11th Ed. (1997), The British Crop Protection Council, London, page 880;

(L) (E)-$N^1$-[(6-chloro-3-pyridyl)methyl]-$N^2$-cyano-$N^1$-methylacetamidine (NI-25, Acetamiprid), from The Pesticide Manual, 11th Ed. (1997), The British Crop Protection Council, London, page 9;

(LI) Avermectin $B_1$, from The Pesticide Manual, 11th Ed. (1997), The British Crop Protection Council, London, page 3;

(LII) an insect-active extract from a plant, especially (2R,6aS,12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11th Ed. (1997), The British Crop Protection Council, London, page 1097; and an extract from *Azadirachta indica*, especially azadirachtin, from The Pesticide Manual, 11th Ed. (1997), The British Crop Protection Council, London, page 59; and (LII) a preparation which contains insect-active nematodes, preferably *Heterorhabditis bactedophora* and *Heterorhabditis megidis*, from The Pesticide Manual, 11th Ed. (1997), The British Crop Protection Council, London, page 671; *Steinemema feltiae*, from The Pesticide Manual, 11th Ed. (1997), The British Crop Protection Council, London, page 1115 and *Steinemema scaptedsci*, from The Pesticide Manual, 11th Ed. (1997), The British Crop Protection Council, London, page 1116;

(LIV) a preparation obtainable from *Bacillus subtilis*, from The Pesticide Manual, 11th Ed. (1997), The British Crop Protection Council, London, page 72; or from a strain of *Bacillus thuringiensis* with the exception of compounds isolated from GC91 or from NCTC11821; The Pesticide Manual, 11th Ed. (1997), The British Crop Protection Council, London, page 73;

(LV) a preparation which contains insect-active fungi, preferably *Verticillium lecanii*, from The Pesticide Manual, 11th Ed. (1997), The British Crop Protection Council, London, page 1266; *Beauveda brogniartii*, from The Pesticide Manual, 11th Ed. (1997), The British Crop Protection Council, London, page 85 and *Beauveda bassiana*, from The Pesticide Manual, 11th Ed. (1997), The British Crop Protection Council, London, page 83;

(LVI) a preparation which contains insect-active viruses, preferably Neodipridon Sertifer NPV, from The Pesticide Manual, 11$^{th}$Ed. (1997), The British Crop Protection Council, London, page 1342; Mamestra brassicae NPV, from The Pesticide Manual, 11$^{th}$Ed. (1997), The British Crop Protection Council, London, page 759 and Cydia pomonella granulosis virus, from The Pesticide Manual, 11$^{th}$Ed. (1997), The British Crop Protection Council, London, page 291;

(CLXXXI) 7-chloro-2,3,4a,5-tetrahydro-2-[methoxycarbonyl(4-trifluoromethoxyphenyl)-carbamoyl]indol[1,2e]oxazoline-4a-carboxylate (DPX-MP062, Indoxycarb), from The Pesticide Manual, 11$^{th}$Ed. (1997), The British Crop Protection Council, London, page 453;

(CLXXXII) N'-tert.-butyl-N'-(3,5-dimethylbenzoyl)-3-methoxy-2-methylbenzohydrazide (RH-2485, Methoxyfenozide), from The Pesticide Manual, 11$^{th}$Ed. (1997), The British Crop Protection Council, London, page 1094; and (CLXXXIII) (N'-[4-methoxy-biphenyl-3-yl]-hydrazinecarboxylic acid isopropylester (D 2341), from Brighton Crop Protection Conference, 1996, 487-493;

($R_2$) Book of Abstracts, 212th ACS National Meeting Orlando, Fla., August 25-29 (1996), AGRO-020. Publisher: American Chemical Society, Washington, D.C. CONEN: 63BFAF.

As a consequence of the above details, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

As a rule, the anthelminthic compositions according to the invention contain 0.1 to 99% by weight, especially 0.1 to 95% by weight of active ingredient of formula I, Ia or mixtures thereof, 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, perorally, parenterally or subcutaneously, the composition being present in the form of solutions, emulsions, suspensions, (drenches), powders, tablets, boli, capsules and pour-on formulations.

The pour-on or spot-on method consists in applying the compound of formula I to a specific location of the skin or coat, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 20% by weight of a compound of formula I, 0.1 to 50% by weight of dispersing agent and 45 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

Anthelminthic compositions of this type, which are used by the end user, similarly form a constituent of the present invention.

In each of the processes according to the invention for pest control or in each of the pest control compositions according to the invention, the active ingredients of formula I can be used in all of their steric configurations or in mixtures thereof.

The invention also includes a method of prophylactically protecting warm-blooded animals, especially productive livestock, domestic animals and pets, against parasitic helminths, which is characterised in that the active ingredients of formula I or the active ingredient formulations prepared therefrom are administered to the animals as an additive to the feed, or to the drinks or also in solid or liquid form, orally or by injection or parenterally. The invention also includes the compounds of formula I according to the invention for usage in one of the said processes.

The following examples serve merely to illustrate the invention without restricting it, the term active ingredient representing a substance listed in table 1.

In particular, preferred formulations are made up as follows:

(%=percent by weight)

Formulation Examples

| 1. Granulate | a) | b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent subsequently concentrated by evaporation under vacuum. Granulates of this kind can be mixed with the animal feed.

2. Granulate

| active ingredient | 3% |
|---|---|
| polyethylene glycol (mw 200) | 3% |
| kaolin | 94% |

(mw = molecular weight)

The finely ground active ingredient is evenly applied in a mixer to the kaolin which has been moistened with polyethylene glycol. In this way, dust-free coated granules are obtained.

3. Tablets or Boli

| | | |
|---|---|---|
| I | active ingredient | 33.00% |
| | methylcellulose | 0.80% |
| | silicic acid. highly dispersed | 0.80% |
| | corn starch | 8.40% |
| II | lactose, cryst. | 22.50% |
| | corn starch | 17.00% |
| | microcryst. cellulose | 16.50% |
| | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.

II All 4 excipients are mixed thoroughly.

III The preliminary mixes obtained according to I and II are mixed and pressed into tablets or boli.

4. Injectables

A. Oily Vehicle (Slow Release)

| | | |
|---|---|---|
| 1. | active ingredient | 0.1-1.0 g |
| | groundnut oil | ad 100 ml |
| 2. | active ingredient | 0.1-1.0 g |
| | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 mm.

B Water-Miscible Solvent (Average Rate of Release)

| active ingredient | 0.1-1.0 g |
|---|---|
| 4-hydroxymethyl-1,3-dioxolane (glycerol formal) | 40 g |
| 1,2-propanediol | ad 100 ml |
| active ingredient | 0.1-1.0 g |
| glycerol dimethyl ketal | 40 g |
| 1,2-propanediol | ad 100 ml |

Preparation: The active ingredient is dissolved in part of the solvent whilst stirring, made up to the desired volume and sterile-filtered through a suitable membrane filter with a pore size of 0.22 mm.

C. Aqueous Solubilisate (Rapid Release)

| | | |
|---|---|---|
| 1. | active ingredient | 0.1-1.0 g |
| | polyethoxylated castor oil (40 ethylene oxide units) | 10 g |
| | 1,2-propanediol | 20 g |
| | benzyl alcohol | 1 g |
| | Aqua ad inject. | ad 100 ml |
| 2. | active ingredient | 0.1-1.0 g |
| | polyethoxylated sorbitan monooleate (20 ethylene oxide units) | 8 g |
| | 4-hydroxymethyl-1,3-dioxolane (glycerol formal) | 20 g |
| | benzyl alcohol | 1 g |
| | Aqua ad inject. | ad 100 ml |

Preparation: The active ingredient is dissolved in the solvents and the surfactant, and made up with water to the desired volume. Sterile filtration through an appropriate membrane filter of 0.22 mm pore size.

5. Pour On

A.

| active ingredient | 5 g |
|---|---|
| isopropyl myristate | 10 g |
| isopropanol | ad 100 ml |

B

| active ingredient | 2 g |
|---|---|
| hexyl laurate | 5 g |
| medium-chained triglyceride | 15 g |
| ethanol | ad 100 ml |

C.

| active ingredient | 2 g |
|---|---|
| oleyl oleate | 5 g |
| N-methyl-pyrrolidone | 40 g |
| isopropanol | ad 100 ml |

The aqueous systems may also preferably be used for oral and/or intraruminal application.

The compositions may also contain further additives, such as stabilisers, e.g. where appropriate epoxidised vegetable oils (epoxidised coconut oil, rapeseed oil, or soybean oil); antifoams, e.g. silicone oil, preservatives, viscosity regulators, binders, tackifiers, as well as fertilisers or other active ingredients to achieve special effects.

Further biologically active substances or additives, which are neutral towards the compounds of formula I and do not have a harmful effect on the host animal to be treated, as well as mineral salts or vitamins, may also be added to the described compositions.

The following examples serve to illustrate the invention. They do not limit the invention. The letter 'h' stands for hour.

PREPARATION EXAMPLES

Example 1

4-Benzoyl-N-[1-cyano-1-methyl-2-(2-trifluoromethylphenoxy)-ethyl]-benzamide

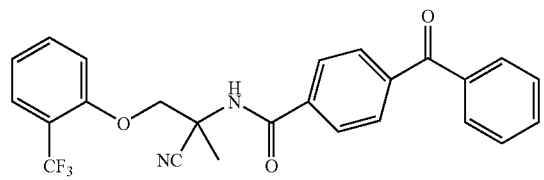

330 mg of benzophenone-4-carboxylic acid are dissolved in 6 ml of dichloromethane, then 283 mg of N-(3-dimethylaminopropyl)-N'-ethylcarbodiimide hydrochloride, 18 mg of 4-dimethylaminopyridine and 222 mg of ethyldiisopropylamine are added, and stirred for 20 minutes at room temperature. 300 mg of 2-amino-2-methyl-3-(2-trifluoromethylphenoxy)-propionitrile are subsequently added, and the mixture stirred for a further 40 hours. Afterwards, the mixed solution is washed with an aqueous sodium bicarbonate solution, then with a 1 n hydrochloric acid solution and finally with a saturated sodium chloride solution. The organic phase is then separated, dried with sodium sulphate, filtered and concentrated by evaporation. After recrystallisation in diethylether, the residue yields 372 mg of the title compound with a melting point of 121-123° C.

The substances named in the following table may also be prepared analogously to the above-described method. The values of the melting points are indicated in ° C. Bd signifies a direct bond, so that "Bd 3-$Ar_1$" signifies a bond between the 3-position on the phenyl ring and $Ar_1$.

TABLE 1

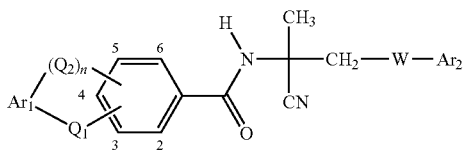

| No. | $Ar_1$ | $Ar_2$ | W | $Q_1$ | n | $Q_2$ | phys. data |
|---|---|---|---|---|---|---|---|
| 1.1 | $C_6H_5$ | $C_6H_5$ | O | 4-$CH_2$ | 0 | | |
| 1.2 | $C_6H_5$ | $C_6H_5$ | O | 3-$CH_2$ | 0 | | |
| 1.3 | $C_6H_5$ | $C_6H_5$ | O | 2-$CH_2$ | 0 | | |
| 1.4 | $C_6H_5$ | $C_6H_5$ | O | 4-$OCH_2$ | 0 | | |
| 1.5 | $C_6H_5$ | $C_6H_5$ | O | 3-$OCH_2$ | 0 | | |
| 1.6 | $C_6H_5$ | $C_6H_5$ | O | 2-$OCH_2$ | 0 | | |
| 1.7 | $C_6H_5$ | $C_6H_5$ | O | 4-S | 0 | | |
| 1.8 | $C_6H_5$ | $C_6H_5$ | O | 3-S | 0 | | |
| 1.9 | $C_6H_5$ | $C_6H_5$ | O | 2-S | 0 | | |
| 1.10 | $C_6H_5$ | $C_6H_5$ | O | 4-S(O) | 0 | | |
| 1.11 | $C_6H_5$ | $C_6H_5$ | O | 3-S(O) | 0 | | |
| 1.12 | $C_6H_5$ | $C_6H_5$ | O | 2-S(O) | 0 | | |
| 1.13 | $C_6H_5$ | $C_6H_5$ | O | 4-C(O) | 0 | | |
| 1.14 | $C_6H_4$ | $C_6H_5$ | O | 4-C(O) | 1 | Bd 3-$Ar_1$ | |
| 1.15 | $C_6H_4$ | $C_6H_5$ | O | 4-C(O) | 1 | 3-C(O) | |
| 1.16 | $C_6H_4$ | $C_6H_5$ | O | 4-C(O) | 1 | 3-$S(O_2)$ | |
| 1.17 | $C_6H_5$ | $C_6H_5$ | O | 3-C(O) | 0 | | |
| 1.18 | $C_6H_4$ | $C_6H_5$ | O | 3-C(O) | 1 | Bd 4-$Ar_1$ | |
| 1.19 | $C_6H_4$ | $C_6H_5$ | O | 3-C(O) | 1 | 4-$S(O_2)$ | |
| 1.20 | $C_6H_5$ | $C_6H_5$ | O | 2-C(O) | 0 | | |
| 1.21 | $C_6H_4$ | $C_6H_5$ | O | 2-C(O) | 1 | Bd 3-$Ar_1$ | |
| 1.22 | $C_6H_4$ | $C_6H_5$ | O | 2-C(O) | 1 | 3-C(O) | |
| 1.23 | $C_6H_4$ | $C_6H_5$ | O | 2-C(O) | 1 | 3-$S(O_2)$ | |
| 1.24 | $C_6H_5$ | $C_6H_5$ | S | 4-$CH_2$ | 0 | | |
| 1.25 | $C_6H_5$ | $C_6H_5$ | S | 3-$CH_2$ | 0 | | |
| 1.26 | $C_6H_5$ | $C_6H_5$ | S | 2-$CH_2$ | 0 | | |
| 1.27 | $C_6H_5$ | $C_6H_5$ | S | 4-$OCH_2$ | 0 | | |
| 1.28 | $C_6H_5$ | $C_6H_5$ | S | 3-$OCH_2$ | 0 | | |
| 1.29 | $C_6H_5$ | $C_6H_5$ | S | 2-$OCH_2$ | 0 | | |
| 1.30 | $C_6H_5$ | $C_6H_5$ | S | 4-S | 0 | | |
| 1.31 | $C_6H_5$ | $C_6H_5$ | S | 3-S | 0 | | |
| 1.32 | $C_6H_5$ | $C_6H_5$ | S | 2-S | 0 | | |
| 1.33 | $C_6H_5$ | $C_6H_5$ | S | 4-S(O) | 0 | | |
| 1.34 | $C_6H_5$ | $C_6H_5$ | S | 3-S(O) | 0 | | |
| 1.35 | $C_6H_5$ | $C_6H_5$ | S | 2-S(O) | 0 | | |
| 1.36 | $C_6H_5$ | $C_6H_5$ | S | 4-C(O) | 0 | | |
| 1.37 | $C_6H_4$ | $C_6H_5$ | S | 4-C(O) | 1 | Bd 3-$Ar_1$ | |
| 1.38 | $C_6H_4$ | $C_6H_5$ | S | 4-C(O) | 1 | 3-C(O) | |
| 1.39 | $C_6H_4$ | $C_6H_5$ | S | 4-C(O) | 1 | 3-$S(O_2)$ | |
| 1.40 | $C_6H_5$ | $C_6H_5$ | S | 3-C(O) | 0 | | |
| 1.41 | $C_6H_4$ | $C_6H_5$ | S | 3-C(O) | 1 | Bd 4-$Ar_1$ | |
| 1.42 | $C_6H_4$ | $C_6H_5$ | S | 3-C(O) | 1 | 4-$S(O_2)$ | |
| 1.43 | $C_6H_5$ | $C_6H_5$ | S | 2-C(O) | 0 | | |
| 1.44 | $C_6H_4$ | $C_6H_5$ | S | 2-C(O) | 1 | Bd 3-$Ar_1$ | |
| 1.45 | $C_6H_4$ | $C_6H_5$ | S | 2-C(O) | 1 | 3-C(O) | |
| 1.46 | $C_6H_4$ | $C_6H_5$ | S | 2-C(O) | 1 | 3-$S(O_2)$ | |
| 1.47 | $C_6H_5$ | $C_6H_4$-2-Cl | O | 4-$CH_2$ | 0 | | |
| 1.48 | $C_6H_5$ | $C_6H_4$-2-Cl | O | 3-$CH_2$ | 0 | | |
| 1.49 | $C_6H_5$ | $C_6H_4$-2-Cl | O | 2-$CH_2$ | 0 | | |
| 1.50 | $C_6H_5$ | $C_6H_4$-2-Cl | O | 4-$OCH_2$ | 0 | | |
| 1.51 | $C_6H_5$ | $C_6H_4$-2-Cl | O | 3-$OCH_2$ | 0 | | |
| 1.52 | $C_6H_5$ | $C_6H_4$-2-Cl | O | 2-$OCH_2$ | 0 | | |
| 1.53 | $C_6H_5$ | $C_6H_4$-2-Cl | O | 4-S | 0 | | |
| 1.54 | $C_6H_5$ | $C_6H_4$-2-Cl | O | 3-S | 0 | | |

TABLE 1-continued

| No. | Ar₁ | Ar₂ | W | Q₁ | n | Q₂ | phys. data |
|---|---|---|---|---|---|---|---|
| 1.55 | C₆H₅ | C₆H₄-2-Cl | O | 2-S | 0 | | |
| 1.56 | C₆H₅ | C₆H₄-2-Cl | O | 4-S(O) | 0 | | |
| 1.57 | C₆H₅ | C₆H₄-2-Cl | O | 3-S(O) | 0 | | |
| 1.58 | C₆H₅ | C₆H₄-2-Cl | O | 2-S(O) | 0 | | |
| 1.59 | C₆H₅ | C₆H₄-2-Cl | O | 4-C(O) | 0 | | m.p. 90-3° |
| 1.60 | C₆H₄ | C₆H₄-2-Cl | O | 4-C(O) | 1 | Bd 3-Ar₁ | |
| 1.61 | C₆H₄ | C₆H₄-2-Cl | O | 4-C(O) | 1 | 3-C(O) | |
| 1.62 | C₆H₄ | C₆H₄-2-Cl | O | 4-C(O) | 1 | 3-S(O₂) | |
| 1.63 | C₆H₅ | C₆H₄-2-Cl | O | 3-C(O) | 0 | | |
| 1.64 | C₆H₄ | C₆H₄-2-Cl | O | 3-C(O) | 1 | Bd 4-Ar₁ | |
| 1.65 | C₆H₄ | C₆H₄-2-Cl | O | 3-C(O) | 1 | 4-S(O₂) | |
| 1.66 | C₆H₅ | C₆H₄-2-Cl | O | 2-C(O) | 0 | | |
| 1.67 | C₆H₄ | C₆H₄-2-Cl | O | 2-C(O) | 1 | Bd 3-Ar₁ | |
| 1.68 | C₆H₄ | C₆H₄-2-Cl | O | 2-C(O) | 1 | 3-C(O) | |
| 1.69 | C₆H₄ | C₆H₄-2-Cl | O | 2-C(O) | 1 | 3-S(O₂) | |
| 1.70 | C₆H₅ | C₆H₄-2-Cl | S | 4-CH₂ | 0 | | |
| 1.71 | C₆H₅ | C₆H₄-2-Cl | S | 3-CH₂ | 0 | | |
| 1.72 | C₆H₅ | C₆H₄-2-Cl | S | 2-CH₂ | 0 | | |
| 1.73 | C₆H₅ | C₆H₄-2-Cl | S | 4-OCH₂ | 0 | | |
| 1.74 | C₆H₅ | C₆H₄-2-Cl | S | 3-OCH₂ | 0 | | |
| 1.75 | C₆H₅ | C₆H₄-2-Cl | S | 2-OCH₂ | 0 | | |
| 1.76 | C₆H₅ | C₆H₄-2-Cl | S | 4-S | 0 | | |
| 1.77 | C₆H₅ | C₆H₄-2-Cl | S | 3-S | 0 | | |
| 1.78 | C₆H₅ | C₆H₄-2-Cl | S | 2-S | 0 | | |
| 1.79 | C₆H₅ | C₆H₄-2-Cl | S | 4-S(O) | 0 | | |
| 1.80 | C₆H₅ | C₆H₄-2-Cl | S | 3-S(O) | 0 | | |
| 1.81 | C₆H₅ | C₆H₄-2-Cl | S | 2-S(O) | 0 | | |
| 1.82 | C₆H₅ | C₆H₄-2-Cl | S | 4-C(O) | 0 | | m.p. 109-10° |
| 1.83 | C₆H₄ | C₆H₄-2-Cl | S | 4-C(O) | 1 | Bd 3-Ar₁ | |
| 1.84 | C₆H₄ | C₆H₄-2-Cl | S | 4-C(O) | 1 | 3-C(O) | |
| 1.85 | C₆H₄ | C₆H₄-2-Cl | S | 4-C(O) | 1 | 3-S(O₂) | |
| 1.86 | C₆H₅ | C₆H₄-2-Cl | S | 3-C(O) | 0 | | |
| 1.87 | C₆H₄ | C₆H₄-2-Cl | S | 3-C(O) | 1 | Bd 4-Ar₁ | |
| 1.88 | C₆H₄ | C₆H₄-2-Cl | S | 3-C(O) | 1 | 4-S(O₂) | |
| 1.89 | C₆H₅ | C₆H₄-2-Cl | S | 2-C(O) | 0 | | |
| 1.90 | C₆H₄ | C₆H₄-2-Cl | S | 2-C(O) | 1 | Bd 3-Ar₁ | |
| 1.91 | C₆H₄ | C₆H₄-2-Cl | S | 2-C(O) | 1 | 3-C(O) | |
| 1.92 | C₆H₄ | C₆H₄-2-Cl | S | 2-C(O) | 1 | 3-S(O₂) | |
| 1.93 | C₆H₅ | C₆H₄-2-CF₃ | O | 4-CH₂ | 0 | | |
| 1.94 | C₆H₅ | C₆H₄-2-CF₃ | O | 3-CH₂ | 0 | | |
| 1.95 | C₆H₅ | C₆H₄-2-CF₃ | O | 2-CH₂ | 0 | | |
| 1.96 | C₆H₅ | C₆H₄-2-CF₃ | O | 4-OCH₂ | 0 | | m.p. 44-8° |
| 1.97 | C₆H₅ | C₆H₄-2-CF₃ | O | 3-OCH₂ | 0 | | |
| 1.98 | C₆H₅ | C₆H₄-2-CF₃ | O | 2-OCH₂ | 0 | | |
| 1.99 | C₆H₅ | C₆H₄-2-CF₃ | O | 4-S | 0 | | |
| 1.100 | C₆H₅ | C₆H₄-2-CF₃ | O | 3-S | 0 | | |
| 1.101 | C₆H₅ | C₆H₄-2-CF₃ | O | 2-S | 0 | | |
| 1.102 | C₆H₅ | C₆H₄-2-CF₃ | O | 4-S(O) | 0 | | |
| 1.103 | C₆H₅ | C₆H₄-2-CF₃ | O | 3-S(O) | 0 | | |
| 1.104 | C₆H₅ | C₆H₄-2-CF₃ | O | 2-S(O) | 0 | | |
| 1.105 | C₆H₅ | C₆H₄-2-CF₃ | O | 4-C(O) | 0 | | m.p. 121-3° |
| 1.106 | C₆H₄ | C₆H₄-2-CF₃ | O | 4-C(O) | 1 | Bd 3-Ar₁ | |
| 1.107 | C₆H₄ | C₆H₄-2-CF₃ | O | 4-C(O) | 1 | 3-C(O) | m.p. 74-8° |
| 1.108 | C₆H₄ | C₆H₄-2-CF₃ | O | 4-C(O) | 1 | 3-S(O₂) | m.p. 207-10° |
| 1.109 | C₆H₅ | C₆H₄-2-CF₃ | O | 3-C(O) | 0 | | |
| 1.110 | C₆H₄ | C₆H₄-2-CF₃ | O | 3-C(O) | 1 | Bd 4-Ar₁ | m.p. 90-3° |
| 1.111 | C₆H₄ | C₆H₄-2-CF₃ | O | 3-C(O) | 1 | 4-S(O₂) | |
| 1.112 | C₆H₅ | C₆H₄-2-CF₃ | O | 2-C(O) | 0 | | |
| 1.113 | C₆H₄ | C₆H₄-2-CF₃ | O | 2-C(O) | 1 | Bd 3-Ar₁ | |
| 1.114 | C₆H₄ | C₆H₄-2-CF₃ | O | 2-C(O) | 1 | 3-C(O) | |
| 1.115 | C₆H₄ | C₆H₄-2-CF₃ | O | 2-C(O) | 1 | 3-S(O₂) | |
| 1.116 | C₆H₅ | C₆H₄-2-CF₃ | S | 4-CH₂ | 0 | | |
| 1.117 | C₆H₅ | C₆H₄-2-CF₃ | S | 3-CH₂ | 0 | | |
| 1.118 | C₆H₅ | C₆H₄-2-CF₃ | S | 2-CH₂ | 0 | | |
| 1.119 | C₆H₅ | C₆H₄-2-CF₃ | S | 4-OCH₂ | 0 | | |
| 1.120 | C₆H₅ | C₆H₄-2-CF₃ | S | 3-OCH₂ | 0 | | |
| 1.121 | C₆H₅ | C₆H₄-2-CF₃ | S | 2-OCH₂ | 0 | | |
| 1.122 | C₆H₅ | C₆H₄-2-CF₃ | S | 4-S | 0 | | |

TABLE 1-continued

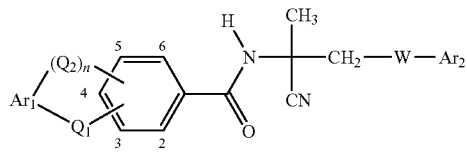

| No. | Ar$_1$ | Ar$_2$ | W | Q$_1$ | n | Q$_2$ | phys. data |
|---|---|---|---|---|---|---|---|
| 1.123 | C$_6$H$_5$ | C$_6$H$_4$-2-CF$_3$ | S | 3-S | 0 | | |
| 1.124 | C$_6$H$_5$ | C$_6$H$_4$-2-CF$_3$ | S | 2-S | 0 | | |
| 1.125 | C$_6$H$_5$ | C$_6$H$_4$-2-CF$_3$ | S | 4-S(O) | 0 | | |
| 1.126 | C$_6$H$_5$ | C$_6$H$_4$-2-CF$_3$ | S | 3-S(O) | 0 | | |
| 1.127 | C$_6$H$_5$ | C$_6$H$_4$-2-CF$_3$ | S | 2-S(O) | 0 | | |
| 1.128 | C$_6$H$_5$ | C$_6$H$_4$-2-CF$_3$ | S | 4-C(O) | 0 | | |
| 1.129 | C$_6$H$_4$ | C$_6$H$_4$-2-CF$_3$ | S | 4-C(O) | 1 | Bd 3-Ar$_1$ | |
| 1.130 | C$_6$H$_4$ | C$_6$H$_4$-2-CF$_3$ | S | 4-C(O) | 1 | 3-C(O) | |
| 1.131 | C$_6$H$_4$ | C$_6$H$_4$-2-CF$_3$ | S | 4-C(O) | 1 | 3-S(O$_2$) | |
| 1.132 | C$_6$H$_5$ | C$_6$H$_4$-2-CF$_3$ | S | 3-C(O) | 0 | | |
| 1.133 | C$_6$H$_4$ | C$_6$H$_4$-2-CF$_3$ | S | 3-C(O) | 1 | Bd 4-Ar$_1$ | |
| 1.134 | C$_6$H$_4$ | C$_6$H$_4$-2-CF$_3$ | S | 3-C(O) | 1 | 4-S(O$_2$) | |
| 1.135 | C$_6$H$_5$ | C$_6$H$_4$-2-CF$_3$ | S | 2-C(O) | 0 | | |
| 1.136 | C$_6$H$_4$ | C$_6$H$_4$-2-CF$_3$ | S | 2-C(O) | 1 | Bd 3-Ar$_1$ | |
| 1.137 | C$_6$H$_4$ | C$_6$H$_4$-2-CF$_3$ | S | 2-C(O) | 1 | 3-C(O) | |
| 1.138 | C$_6$H$_4$ | C$_6$H$_4$-2-CF$_3$ | S | 2-C(O) | 1 | 3-S(O$_2$) | |
| 1.139 | C$_6$H$_4$-4-F | C$_6$H$_5$ | O | 4-CH$_2$ | 0 | | |
| 1.140 | C$_6$H$_4$-4-F | C$_6$H$_5$ | O | 3-CH$_2$ | 0 | | |
| 1.141 | C$_6$H$_4$-4-F | C$_6$H$_5$ | O | 2-CH$_2$ | 0 | | |
| 1.142 | C$_6$H$_4$-4-F | C$_6$H$_5$ | O | 4-OCH$_2$ | 0 | | |
| 1.143 | C$_5$H$_4$-4-F | C$_6$H$_5$ | O | 3-OCH$_2$ | 0 | | |
| 1.144 | C$_6$H$_4$-4-F | C$_6$H$_5$ | O | 2-OCH$_2$ | 0 | | |
| 1.145 | C$_6$H$_4$-4-F | C$_6$H$_5$ | O | 4-S | 0 | | |
| 1.146 | C$_6$H$_4$-4-F | C$_6$H$_5$ | O | 3-S | 0 | | |
| 1.147 | C$_6$H$_4$-4-F | C$_6$H$_5$ | O | 2-S | 0 | | |
| 1.148 | C$_6$H$_4$-4-F | C$_6$H$_5$ | O | 4-S(O) | 0 | | |
| 1.149 | C$_6$H$_4$-4-F | C$_6$H$_5$ | O | 3-S(O) | 0 | | |
| 1.150 | C$_6$H$_4$-4-F | C$_6$H$_5$ | O | 2-S(O) | 0 | | |
| 1.151 | C$_6$H$_4$-4-F | C$_6$H$_5$ | O | 4-C(O) | 0 | | |
| 1.152 | C$_6$H$_3$-4-F | C$_6$H$_5$ | O | 4-C(O) | 1 | Bd 3-Ar$_1$ | |
| 1.153 | C$_6$H$_3$-4-F | C$_6$H$_5$ | O | 4-C(O) | 1 | 3-C(O) | |
| 1.154 | C$_6$H$_3$-4-F | C$_6$H$_5$ | O | 4-C(O) | 1 | 3-S(O$_2$) | |
| 1.155 | C$_6$H$_4$-4-F | C$_6$H$_5$ | O | 3-C(O) | 0 | | |
| 1.156 | C$_6$H$_3$-4-F | C$_6$H$_5$ | O | 3-C(O) | 1 | Bd 4-Ar$_1$ | |
| 1.157 | C$_6$H$_3$-4-F | C$_6$H$_5$ | O | 3-C(O) | 1 | 4-S(O$_2$) | |
| 1.158 | C$_6$H$_4$-4-F | C$_6$H$_5$ | O | 2-C(O) | 0 | | |
| 1.159 | C$_6$H$_3$-4-F | C$_6$H$_5$ | O | 2-C(O) | 1 | Bd 3-Ar$_1$ | |
| 1.160 | C$_6$H$_3$-4-F | C$_6$H$_5$ | O | 2-C(O) | 1 | 3-C(O) | |
| 1.161 | C$_6$H$_3$-4-F | C$_6$H$_5$ | O | 2-C(O) | 1 | 3-S(O$_2$) | |
| 1.162 | C$_6$H$_4$-4-F | C$_6$H$_5$ | S | 4-CH$_2$ | 0 | | |
| 1.163 | C$_6$H$_4$-4-F | C$_6$H$_5$ | S | 3-CH$_2$ | 0 | | |
| 1.164 | C$_6$H$_4$-4-F | C$_6$H$_5$ | S | 2-CH$_2$ | 0 | | |
| 1.165 | C$_6$H$_4$-4-F | C$_6$H$_5$ | S | 4-OCH$_2$ | 0 | | |
| 1.166 | C$_6$H$_4$-4-F | C$_6$H$_5$ | S | 3-OCH$_2$ | 0 | | |
| 1.167 | C$_6$H$_4$-4-F | C$_6$H$_5$ | S | 2-OCH$_2$ | 0 | | |
| 1.168 | C$_6$H$_4$-4-F | C$_6$H$_5$ | S | 4-S | 0 | | |
| 1.169 | C$_6$H$_4$-4-F | C$_6$H$_5$ | S | 3-S | 0 | | |
| 1.170 | C$_6$H$_4$-4-F | C$_6$H$_5$ | S | 2-S | 0 | | |
| 1.171 | C$_6$H$_4$-4-F | C$_6$H$_5$ | S | 4-S(O) | 0 | | |
| 1.172 | C$_6$H$_4$-4-F | C$_6$H$_5$ | S | 3-S(O) | 0 | | |
| 1.173 | C$_6$H$_4$-4-F | C$_6$H$_5$ | S | 2-S(O) | 0 | | |
| 1.174 | C$_6$H$_4$-4-F | C$_6$H$_5$ | S | 4-C(O) | 0 | | |
| 1.175 | C$_6$H$_3$-4-F | C$_6$H$_5$ | S | 4-C(O) | 1 | Bd 3-Ar$_1$ | |
| 1.176 | C$_6$H$_3$-4-F | C$_6$H$_5$ | S | 4-C(O) | 1 | 3-C(O) | |
| 1.177 | C$_6$H$_3$-4-F | C$_6$H$_5$ | S | 4-C(O) | 1 | 3-S(O$_2$) | |
| 1.178 | C$_6$H$_4$-4-F | C$_6$H$_5$ | S | 3-C(O) | 0 | | |
| 1.179 | C$_6$H$_3$-4-F | C$_6$H$_5$ | S | 3-C(O) | 1 | Bd 4-Ar$_1$ | |
| 1.180 | C$_6$H$_3$-4-F | C$_6$H$_5$ | S | 3-C(O) | 1 | 4-S(O$_2$) | |
| 1.181 | C$_6$H$_4$-4-F | C$_6$H$_5$ | S | 2-C(O) | 0 | | |
| 1.182 | C$_6$H$_3$-4-F | C$_6$H$_5$ | S | 2-C(O) | 1 | Bd 3-Ar$_1$ | |
| 1.183 | C$_6$H$_3$-4-F | C$_6$H$_5$ | S | 2-C(O) | 1 | 3-C(O) | |
| 1.184 | C$_6$H$_3$-4-F | C$_6$H$_5$ | S | 2-C(O) | 1 | 3-S(O$_2$) | |
| 1.185 | C$_6$H$_4$-4-F | C$_6$H$_4$-2-Cl | O | 4-CH$_2$ | 0 | | |
| 1.186 | C$_6$H$_4$-4-F | C$_6$H$_4$-2-Cl | O | 3-CH$_2$ | 0 | | |
| 1.187 | C$_6$H$_4$-4-F | C$_6$H$_4$-2-Cl | O | 2-CH$_2$ | 0 | | |
| 1.188 | C$_6$H$_4$-4-F | C$_6$H$_4$-2-Cl | O | 4-OCH$_2$ | 0 | | |
| 1.189 | C$_6$H$_4$-4-F | C$_6$H$_4$-2-Cl | O | 3-OCH$_2$ | 0 | | |
| 1.190 | C$_6$H$_4$-4-F | C$_6$H$_4$-2-Cl | O | 2-OCH$_2$ | 0 | | |

TABLE 1-continued

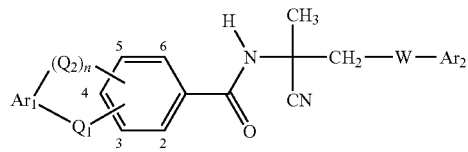

| No. | Ar₁ | Ar₂ | W | Q₁ | n | Q₂ | phys. data |
|---|---|---|---|---|---|---|---|
| 1.191 | C₆H₄-4-F | C₆H₄-2-Cl | O | 4-S | 0 | | |
| 1.192 | C₆H₄-4-F | C₆H₄-2-Cl | O | 3-S | 0 | | |
| 1.193 | C₆H₄-4-F | C₆H₄-2-Cl | O | 2-S | 0 | | |
| 1.194 | C₆H₄-4-F | C₆H₄-2-Cl | O | 4-S(O) | 0 | | |
| 1.195 | C₆H₄-4-F | C₆H₄-2-Cl | O | 3-(O) | 0 | | |
| 1.196 | C₆H₄-4-F | C₆H₄-2-Cl | O | 2-S(O) | 0 | | |
| 1.197 | C₆H₄-4-F | C₆H₄-2-Cl | O | 4-C(O) | 0 | | |
| 1.198 | C₆H₃-4-F | C₆H₄-2-Cl | O | 4-C(O) | 1 | Bd 3-Ar₁ | |
| 1.199 | C₆H₃-4-F | C₆H₄-2-Cl | O | 4-C(O) | 1 | 3-C(O) | |
| 1.200 | C₆H₃-4-F | C₆H₄-2-Cl | O | 4-C(O) | 1 | 3-S(O₂) | |
| 1.201 | C₆H₄-4-F | C₆H₄-2-Cl | O | 3-C(O) | 0 | | |
| 1.202 | C₆H₃-4-F | C₆H₄-2-Cl | O | 3-C(O) | 1 | Bd 4-Ar₁ | |
| 1.203 | C₆H₃-4-F | C₆H₄-2-Cl | O | 3-C(O) | 1 | 4-S(O₂) | |
| 1.204 | C₆H₄-4-F | C₆H₄-2-Cl | O | 2-C(O) | 0 | | |
| 1.205 | C₆H₃-4-F | C₆H₄-2-Cl | O | 2-C(O) | 1 | Bd 3-Ar₁ | |
| 1.206 | C₆H₃-4-F | C₆H₄-2-Cl | O | 2-C(O) | 1 | 3-C(O) | |
| 1.207 | C₆H₃-4-F | C₆H₄-2-Cl | O | 2-C(O) | 1 | 3-S(O₂) | |
| 1.208 | C₆H₄-4-F | C₆H₄-2-Cl | S | 4-CH₂ | 0 | | |
| 1.209 | C₆H₄-4-F | C₆H₄-2-Cl | S | 3-CH₂ | 0 | | |
| 1.210 | C₆H₄-4-F | C₆H₄-2-Cl | S | 2-CH₂ | 0 | | |
| 1.211 | C₆H₄-4-F | C₆H₄-2-Cl | S | 4-OCH₂ | 0 | | |
| 1.212 | C₆H₄-4-F | C₆H₄-2-Cl | S | 3-OCH₂ | 0 | | |
| 1.213 | C₆H₄-4-F | C₆H₄-2-Cl | S | 2-OCH₂ | 0 | | |
| 1.214 | C₆H₄-4-F | C₆H₄-2-Cl | S | 4-S | 0 | | |
| 1.215 | C₆H₄-4-F | C₆H₄-2-Cl | S | 3-S | 0 | | |
| 1.216 | C₆H₄-4-F | C₆H₄-2-Cl | S | 2-S | 0 | | |
| 1.217 | C₆H₄-4-F | C₆H₄-2-Cl | S | 4-S(O) | 0 | | |
| 1.218 | C₆H₄-4-F | C₆H₄-2-Cl | S | 3-S(O) | 0 | | |
| 1.219 | C₆H₄-4-F | C₆H₄-2-Cl | S | 2-S(O) | 0 | | |
| 1.220 | C₆H₄-4-F | C₆H₄-2-Cl | S | 4-C(O) | 0 | | |
| 1.221 | C₆H₃-4-F | C₆H₄-2-Cl | S | 4-C(O) | 1 | Bd 3-Ar₁ | |
| 1.222 | C₆H₃-4-F | C₆H₄-2-Cl | S | 4-C(O) | 1 | 3-C(O) | |
| 1.223 | C₆H₃-4-F | C₆H₄-2-Cl | S | 4-C(O) | 1 | 3-S(O₂) | |
| 1.224 | C₆H₄-4-F | C₆H₄-2-Cl | S | 3-C(O) | 0 | | |
| 1.225 | C₆H₃-4-F | C₆H₄-2-Cl | S | 3-C(O) | 1 | Bd 4-Ar₁ | |
| 1.226 | C₆H₃-4-F | C₆H₄-2-Cl | S | 3-C(O) | 1 | 4-S(O₂) | |
| 1.227 | C₆H₄-4-F | C₆H₄-2-Cl | S | 2-C(O) | 0 | | |
| 1.228 | C₆H₃-4-F | C₆H₄-2-Cl | S | 2-C(O) | 1 | Bd 3-Ar₁ | |
| 1.229 | C₆H₃-4-F | C₆H₄-2-Cl | S | 2-C(O) | 1 | 3-C(O) | |
| 1.230 | C₆H₃-4-F | C₆H₄-2-Cl | S | 2-C(O) | 1 | 3-S(O₂) | |
| 1.231 | C₆H₄-4-F | C₆H₄-2-CF₃ | O | 4-CH₂ | 0 | | |
| 1.232 | C₆H₄-4-F | C₆H₄-2-CF₃ | O | 3-CH₂ | 0 | | |
| 1.233 | C₆H₄-4-F | C₆H₄-2-CF₃ | O | 2-CH₂ | 0 | | |
| 1.234 | C₆H₄-4-F | C₆H₄-2-CF₃ | O | 4-OCH₂ | 0 | | |
| 1.235 | C₆H₄-4-F | C₆H₄-2-CF₃ | O | 3-OCH₂ | 0 | | |
| 1.236 | C₆H₄-4-F | C₆H₄-2-CF₃ | O | 2-OCH₂ | 0 | | |
| 1.237 | C₆H₄-4-F | C₆H₄-2-CF₃ | O | 4-S | 0 | | |
| 1.238 | C₆H₄-4-F | C₆H₄-2-CF₃ | O | 3-S | 0 | | |
| 1.239 | C₆H₄-4-F | C₆H₄-2-CF₃ | O | 2-S | 0 | | |
| 1.240 | C₆H₄-4-F | C₆H₄-2-CF₃ | O | 4-S(O) | 0 | | |
| 1.241 | C₆H₄-4-F | C₆H₄-2-CF₃ | O | 3-S(O) | 0 | | |
| 1.242 | C₆H₄-4-F | C₆H₄-2-CF₃ | O | 2-S(O) | 0 | | |
| 1.243 | C₆H₄-4-F | C₆H₄-2-CF₃ | O | 4-C(O) | 0 | | |
| 1.244 | C₆H₃-4-F | C₆H₄-2-CF₃ | O | 4-C(O) | 1 | Bd 3-Ar₁ | |
| 1.245 | C₆H₃-4-F | C₆H₄-2-CF₃ | O | 4-C(O) | 1 | 3-C(O) | |
| 1.246 | C₆H₃-4-F | C₆H₄-2-CF₃ | O | 4-C(O) | 1 | 3-S(O₂) | |
| 1.247 | C₆H₄-4-F | C₆H₄-2-CF₃ | O | 3-C(O) | 0 | | |
| 1.248 | C₆H₃-4-F | C₆H₄-2-CF₃ | O | 3-C(O) | 1 | Bd 4-Ar₁ | |
| 1.249 | C₆H₃-4-F | C₆H₄-2-CF₃ | O | 3-C(O) | 1 | 4-S(O₂) | |
| 1.250 | C₆H₄-4-F | C₆H₄-2-CF₃ | O | 2-C(O) | 0 | | |
| 1.251 | C₆H₃-4-F | C₆H₄-2-CF₃ | O | 2-C(O) | 1 | Bd 3-Ar₁ | |
| 1.252 | C₆H₃-4-F | C₆H₄-2-CF₃ | O | 2-C(O) | 1 | 3-C(O) | |
| 1.253 | C₆H₃-4-F | C₆H₄-2-CF₃ | O | 2-C(O) | 1 | 3-S(O₂) | |
| 1.254 | C₆H₄-4-F | C₆H₄-2-CF₃ | S | 4-CH₂ | 0 | | |
| 1.255 | C₆H₄-4-F | C₆H₄-2-CF₃ | S | 3-CH₂ | 0 | | |
| 1.256 | C₆H₄-4-F | C₆H₄-2-CF₃ | S | 2-CH₂ | 0 | | |
| 1.257 | C₆H₄-4-F | C₆H₄-2-CF₃ | S | 4-OCH₂ | 0 | | |
| 1.258 | C₆H₄-4-F | C₆H₄-2-CF₃ | S | 3-OCH₂ | 0 | | |

TABLE 1-continued

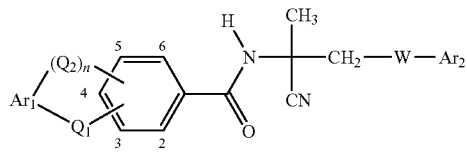

| No. | Ar$_1$ | Ar$_2$ | W | Q$_1$ | n | Q$_2$ | phys. data |
|---|---|---|---|---|---|---|---|
| 1.259 | C$_6$H$_4$-4-F | C$_6$H$_4$-2-CF$_3$ | S | 2-OCH$_2$ | 0 | | |
| 1.260 | C$_6$H$_4$-4-F | C$_6$H$_4$-2-CF$_3$ | S | 4-S | 0 | | |
| 1.261 | C$_6$H$_4$-4-F | C$_6$H$_4$-2-CF$_3$ | S | 3-S | 0 | | |
| 1.262 | C$_6$H$_4$-4-F | C$_6$H$_4$-2-CF$_3$ | S | 2-S | 0 | | |
| 1.263 | C$_6$H$_4$-4-F | C$_6$H$_4$-2-CF$_3$ | S | 4-S(O) | 0 | | |
| 1.264 | C$_6$H$_4$-4-F | C$_6$H$_4$-2-CF$_3$ | S | 3-S(O) | 0 | | |
| 1.265 | C$_6$H$_4$-4-F | C$_6$H$_4$-2-CF$_3$ | S | 2-S(O) | 0 | | |
| 1.266 | C$_6$H$_4$-4-F | C$_6$H$_4$-2-CF$_3$ | S | 4-C(O) | 0 | | |
| 1.267 | C$_6$H$_3$-4-F | C$_6$H$_4$-2-CF$_3$ | S | 4-C(O) | 1 | Bd 3-Ar$_1$ | |
| 1.268 | C$_6$H$_3$-4-F | C$_6$H$_4$-2-CF$_3$ | S | 4-C(O) | 1 | 3-C(O) | |
| 1.269 | C$_6$H$_3$-4-F | C$_6$H$_4$-2-CF$_3$ | S | 4-C(O) | 1 | 3-S(O$_2$) | |
| 1.270 | C$_6$H$_4$-4-F | C$_6$H$_4$-2-CF$_3$ | S | 3-C(O) | 0 | | |
| 1.271 | C$_6$H$_3$-4-F | C$_6$H$_4$-2-CF$_3$ | S | 3-C(O) | 1 | Bd 4-Ar$_1$ | |
| 1.272 | C$_6$H$_3$-4-F | C$_6$H$_4$-2-CF$_3$ | S | 3-C(O) | 1 | 4-S(O$_2$) | |
| 1.273 | C$_6$H$_4$-4-F | C$_6$H$_4$-2-CF$_3$ | S | 2-C(O) | 0 | | |
| 1.274 | C$_6$H$_3$-4-F | C$_6$H$_4$-2-CF$_3$ | S | 2-C(O) | 1 | Bd 3-Ar$_1$ | |
| 1.275 | C$_6$H$_3$-4-F | C$_6$H$_4$-2-CF$_3$ | S | 2-C(O) | 1 | 3-C(O) | |
| 1.276 | C$_6$H$_3$-4-F | C$_6$H$_4$-2-CF$_3$ | S | 2-C(O) | 1 | 3-S(O$_2$) | |
| 1.277 | C$_6$H$_4$-4-Cl | C$_6$H$_5$ | O | 4-CH$_2$ | 0 | | |
| 1.278 | C$_6$H$_4$-4-Cl | C$_6$H$_5$ | O | 3-CH$_2$ | 0 | | |
| 1.279 | C$_6$H$_4$-4-Cl | C$_6$H$_5$ | O | 2-CH$_2$ | 0 | | |
| 1.280 | C$_6$H$_4$-4-Cl | C$_6$H$_5$ | O | 4-OCH$_2$ | 0 | | |
| 1.281 | C$_6$H$_4$-4-Cl | C$_6$H$_5$ | O | 3-OCH$_2$ | 0 | | |
| 1.282 | C$_6$H$_4$-4-Cl | C$_6$H$_5$ | O | 2-OCH$_2$ | 0 | | |
| 1.283 | C$_6$H$_4$-4-Cl | C$_6$H$_5$ | O | 4-S | 0 | | |
| 1.284 | C$_6$H$_4$-4-Cl | C$_6$H$_5$ | O | 3-S | 0 | | |
| 1.285 | C$_6$H$_4$-4-Cl | C$_6$H$_5$ | O | 2-S | 0 | | |
| 1.286 | C$_6$H$_4$-4-Cl | C$_6$H$_5$ | O | 4-S(O) | 0 | | |
| 1.287 | C$_6$H$_4$-4-Cl | C$_6$H$_5$ | O | 3-S(O) | 0 | | |
| 1.288 | C$_6$H$_4$-4-Cl | C$_6$H$_5$ | O | 2-S(O) | 0 | | |
| 1.289 | C$_6$H$_4$-4-Cl | C$_6$H$_5$ | O | 4-C(O) | 0 | | |
| 1.290 | C$_6$H$_3$-4-Cl | C$_6$H$_5$ | O | 4-C(O) | 1 | Bd 3-Ar$_1$ | |
| 1.291 | C$_6$H$_3$-4-Cl | C$_6$H$_5$ | O | 4-C(O) | 1 | 3-C(O) | |
| 1.292 | C$_6$H$_3$-4-Cl | C$_6$H$_5$ | O | 4-C(O) | 1 | 3-S(O$_2$) | |
| 1.293 | C$_6$H$_4$-4-Cl | C$_6$H$_5$ | O | 3-C(O) | 0 | | |
| 1.294 | C$_6$H$_3$-4-Cl | C$_6$H$_5$ | O | 3-C(O) | 1 | Bd 4-Ar$_1$ | |
| 1.295 | C$_6$H$_3$-4-Cl | C$_6$H$_5$ | O | 3-C(O) | 1 | 4-S(O$_2$) | |
| 1.296 | C$_6$H$_4$-4-Cl | C$_6$H$_5$ | O | 2-C(O) | 0 | | |
| 1.297 | C$_6$H$_3$-4-Cl | C$_6$H$_5$ | O | 2-C(O) | 1 | Bd 3-Ar$_1$ | |
| 1.298 | C$_6$H$_3$-4-Cl | C$_6$H$_5$ | O | 2-C(O) | 1 | 3-C(O) | |
| 1.299 | C$_6$H$_3$-4-Cl | C$_6$H$_5$ | O | 2-C(O) | 1 | 3-S(O$_2$) | |
| 1.300 | C$_6$H$_4$-4-Cl | C$_6$H$_5$ | S | 4-CH$_2$ | 0 | | |
| 1.301 | C$_6$H$_4$-4-Cl | C$_6$H$_5$ | S | 3-CH$_2$ | 0 | | |
| 1.302 | C$_6$H$_4$-4-Cl | C$_6$H$_5$ | S | 2-CH$_2$ | 0 | | |
| 1.303 | C$_6$H$_4$-4-Cl | C$_6$H$_5$ | S | 4-OCH$_2$ | 0 | | |
| 1.304 | C$_6$H$_4$-4-Cl | C$_6$H$_5$ | S | 3-OCH$_2$ | 0 | | |
| 1.305 | C$_6$H$_4$-4-Cl | C$_6$H$_5$ | S | 2-OCH$_2$ | 0 | | |
| 1.306 | C$_6$H$_4$-4-Cl | C$_6$H$_5$ | S | 4-S | 0 | | |
| 1.307 | C$_6$H$_4$-4-Cl | C$_6$H$_5$ | S | 3-S | 0 | | |
| 1.308 | C$_6$H$_4$-4-Cl | C$_6$H$_5$ | S | 2-S | 0 | | |
| 1.309 | C$_6$H$_4$-4-Cl | C$_6$H$_5$ | S | 4-S(O) | 0 | | |
| 1.310 | C$_6$H$_4$-4-Cl | C$_6$H$_5$ | S | 3-S(O) | 0 | | |
| 1.311 | C$_6$H$_4$-4-Cl | C$_6$H$_5$ | S | 2-S(O) | 0 | | |
| 1.312 | C$_6$H$_4$-4-Cl | C$_6$H$_5$ | S | 4-C(O) | 0 | | |
| 1.313 | C$_6$H$_3$-4-Cl | C$_6$H$_5$ | S | 4-C(O) | 1 | Bd 3-Ar$_1$ | |
| 1.314 | C$_6$H$_3$-4-Cl | C$_6$H$_5$ | S | 4-C(O) | 1 | 3-C(O) | |
| 1.315 | C$_6$H$_3$-4-Cl | C$_6$H$_5$ | S | 4-C(O) | 1 | 3-S(O$_2$) | |
| 1.316 | C$_6$H$_4$-4-Cl | C$_6$H$_5$ | S | 3-C(O) | 0 | | |
| 1.317 | C$_6$H$_3$-4-Cl | C$_6$H$_5$ | S | 3-C(O) | 1 | Bd 4-Ar$_1$ | |
| 1.318 | C$_6$H$_3$-4-Cl | C$_6$H$_5$ | S | 3-C(O) | 1 | 4-S(O$_2$) | |
| 1.319 | C$_6$H$_4$-4-Cl | C$_6$H$_5$ | S | 2-C(O) | 0 | | |
| 1.320 | C$_6$H$_3$-4-Cl | C$_6$H$_5$ | S | 2-C(O) | 1 | Bd 3-Ar$_1$ | |
| 1.321 | C$_6$H$_3$-4-Cl | C$_6$H$_5$ | S | 2-C(O) | 1 | 3-C(O) | |
| 1.322 | C$_6$H$_3$-4-Cl | C$_6$H$_5$ | S | 2-C(O) | 1 | 3-S(O$_2$) | |
| 1.323 | C$_6$H$_4$-4-Cl | C$_6$H$_4$-2-Cl | O | 4-CH$_2$ | 0 | | |
| 1.324 | C$_6$H$_4$-4-Cl | C$_6$H$_4$-2-Cl | O | 3-CH$_2$ | 0 | | |
| 1.325 | C$_6$H$_4$-4-Cl | C$_6$H$_4$-2-Cl | O | 2-CH$_2$ | 0 | | |
| 1.326 | C$_6$H$_4$-4-Cl | C$_6$H$_4$-2-Cl | O | 4-OCH$_2$ | 0 | | |

TABLE 1-continued

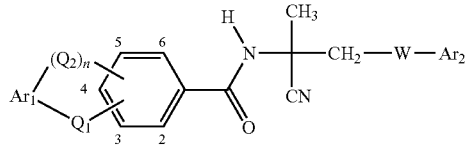

| No. | Ar$_1$ | Ar$_2$ | W | Q$_1$ | n | Q$_2$ | phys. data |
|---|---|---|---|---|---|---|---|
| 1.327 | C$_6$H$_4$-4-Cl | C$_6$H$_4$-2-Cl | O | 3-OCH$_2$ | 0 | | |
| 1.328 | C$_6$H$_4$-4-Cl | C$_6$H$_4$-2-Cl | O | 2-OCH$_2$ | 0 | | |
| 1.329 | C$_6$H$_4$-4-Cl | C$_6$H$_4$-2-Cl | O | 4-S | 0 | | |
| 1.330 | C$_6$H$_4$-4-Cl | C$_6$H$_4$-2-Cl | O | 3-S | 0 | | |
| 1.331 | C$_6$H$_4$-4-Cl | C$_6$H$_4$-2-Cl | O | 2-S | 0 | | |
| 1.332 | C$_6$H$_4$-4-Cl | C$_6$H$_4$-2-Cl | O | 4-S(O) | 0 | | |
| 1.333 | C$_6$H$_4$-4-Cl | C$_6$H$_4$-2-Cl | O | 3-S(O) | 0 | | |
| 1.334 | C$_6$H$_4$-4-Cl | C$_6$H$_4$-2-Cl | O | 2-S(O) | 0 | | |
| 1.335 | C$_6$H$_4$-4-Cl | C$_6$H$_4$-2-Cl | O | 4-C(O) | 0 | | |
| 1.336 | C$_6$H$_3$-4-Cl | C$_6$H$_4$-2-Cl | O | 4-C(O) | 1 | Bd 3-Ar$_1$ | |
| 1.337 | C$_6$H$_3$-4-Cl | C$_6$H$_4$-2-Cl | O | 4-C(O) | 1 | 3-C(O) | |
| 1.338 | C$_6$H$_3$-4-Cl | C$_6$H$_4$-2-Cl | O | 4-C(O) | 1 | 3-S(O$_2$) | |
| 1.339 | C$_6$H$_4$-4-Cl | C$_6$H$_4$-2-Cl | O | 3-C(O) | 0 | | |
| 1.340 | C$_6$H$_3$-4-Cl | C$_6$H$_4$-2-Cl | O | 3-C(O) | 1 | Bd 4-Ar$_1$ | |
| 1.341 | C$_6$H$_3$-4-Cl | C$_6$H$_4$-2-Cl | O | 3-C(O) | 1 | 4-S(O$_2$) | |
| 1.342 | C$_6$H$_4$-4-Cl | C$_6$H$_4$-2-Cl | O | 2-C(O) | 0 | | |
| 1.343 | C$_6$H$_3$-4-Cl | C$_6$H$_4$-2-Cl | O | 2-C(O) | 1 | Bd 3-Ar$_1$ | |
| 1.344 | C$_6$H$_3$-4-Cl | C$_6$H$_4$-2-Cl | O | 2-C(O) | 1 | 3-C(O) | |
| 1.345 | C$_6$H$_3$-4-Cl | C$_6$H$_4$-2-Cl | O | 2-C(O) | 1 | 3-S(O$_2$) | |
| 1.346 | C$_6$H$_4$-4-Cl | C$_6$H$_4$-2-Cl | S | 4-CH$_2$ | 0 | | |
| 1.347 | C$_6$H$_4$-4-Cl | C$_6$H$_4$-2-Cl | S | 3-CH$_2$ | 0 | | |
| 1.348 | C$_6$H$_4$-4-Cl | C$_6$H$_4$-2-Cl | S | 2-CH$_2$ | 0 | | |
| 1.349 | C$_6$H$_4$-4-Cl | C$_6$H$_4$-2-Cl | S | 4-OCH$_2$ | 0 | | |
| 1.350 | C$_6$H$_4$-4-Cl | C$_6$H$_4$-2-Cl | S | 3-OCH$_2$ | 0 | | |
| 1.351 | C$_6$H$_4$-4-Cl | C$_6$H$_4$-2-Cl | S | 2-OCH$_2$ | 0 | | |
| 1.352 | C$_6$H$_4$-4-Cl | C$_6$H$_4$-2-Cl | S | 4-S | 0 | | |
| 1.353 | C$_6$H$_4$-4-Cl | C$_6$H$_4$-2-Cl | S | 3-S | 0 | | |
| 1.354 | C$_6$H$_4$-4-Cl | C$_6$H$_4$-2-Cl | S | 2-S | 0 | | |
| 1.355 | C$_6$H$_4$-4-Cl | C$_6$H$_4$-2-Cl | S | 4-S(O) | 0 | | |
| 1.356 | C$_6$H$_4$-4-Cl | C$_6$H$_4$-2-Cl | S | 3-S(O) | 0 | | |
| 1.357 | C$_6$H$_4$-4-Cl | C$_6$H$_4$-2-Cl | S | 2-S(O) | 0 | | |
| 1.358 | C$_6$H$_4$-4-Cl | C$_6$H$_4$-2-Cl | S | 4-C(O) | 0 | | |
| 1.359 | C$_6$H$_3$-4-Cl | C$_6$H$_4$-2-Cl | S | 4-C(O) | 1 | Bd 3-Ar$_1$ | |
| 1.360 | C$_6$H$_3$-4-Cl | C$_6$H$_4$-2-Cl | S | 4-C(O) | 1 | 3-C(O) | |
| 1.361 | C$_6$H$_3$-4-Cl | C$_6$H$_4$-2-Cl | S | 4-C(O) | 1 | 3-S(O$_2$) | |
| 1.362 | C$_6$H$_4$-4-Cl | C$_6$H$_4$-2-Cl | S | 3-C(O) | 0 | | |
| 1.363 | C$_6$H$_3$-4-Cl | C$_6$H$_4$-2-Cl | S | 3-C(O) | 1 | Bd 4-Ar$_1$ | |
| 1.364 | C$_6$H$_3$-4-Cl | C$_6$H$_4$-2-Cl | S | 3-C(O) | 1 | 4-S(O$_2$) | |
| 1.365 | C$_6$H$_4$-4-Cl | C$_6$H$_4$-2-Cl | S | 2-C(O) | 0 | | |
| 1.366 | C$_6$H$_3$-4-Cl | C$_6$H$_4$-2-Cl | S | 2-C(O) | 1 | Bd 3-Ar$_1$ | |
| 1.367 | C$_6$H$_3$-4-Cl | C$_6$H$_4$-2-Cl | S | 2-C(O) | 1 | 3-C(O) | |
| 1.368 | C$_6$H$_3$-4-Cl | C$_6$H$_4$-2-Cl | S | 2-C(O) | 1 | 3-S(O$_2$) | |
| 1.369 | C$_6$H$_4$-4-Cl | C$_6$H$_4$-2-CF$_3$ | O | 4-CH$_2$ | 0 | | |
| 1.370 | C$_6$H$_4$-4-Cl | C$_6$H$_4$-2-CF$_3$ | O | 3-CH$_2$ | 0 | | |
| 1.371 | C$_6$H$_4$-4-Cl | C$_6$H$_4$-2-CF$_3$ | O | 2-CH$_2$ | 0 | | |
| 1.372 | C$_6$H$_4$-4-Cl | C$_6$H$_4$-2-CF$_3$ | O | 4-OCH$_2$ | 0 | | |
| 1.373 | C$_6$H$_4$-4-Cl | C$_6$H$_4$-2-CF$_3$ | O | 3-OCH$_2$ | 0 | | |
| 1.374 | C$_6$H$_4$-4-Cl | C$_6$H$_4$-2-CF$_3$ | O | 2-OCH$_2$ | 0 | | |
| 1.375 | C$_6$H$_4$-4-Cl | C$_6$H$_4$-2-CF$_3$ | O | 4-S | 0 | | |
| 1.376 | C$_6$H$_4$-4-Cl | C$_6$H$_4$-2-CF$_3$ | O | 3-S | 0 | | |
| 1.377 | C$_6$H$_4$-4-Cl | C$_6$H$_4$-2-CF$_3$ | O | 2-S | 0 | | |
| 1.378 | C$_6$H$_4$-4-Cl | C$_6$H$_4$-2-CF$_3$ | O | 4-S(O) | 0 | | |
| 1.379 | C$_6$H$_4$-4-Cl | C$_6$H$_4$-2-CF$_3$ | O | 3-S(O) | 0 | | |
| 1.380 | C$_6$H$_4$-4-Cl | C$_6$H$_4$-2-CF$_3$ | O | 2-S(O) | 0 | | |
| 1.381 | C$_6$H$_4$-4-Cl | C$_6$H$_4$-2-CF$_3$ | O | 4-C(O) | 0 | | |
| 1.382 | C$_6$H$_3$-4-Cl | C$_6$H$_4$-2-CF$_3$ | O | 4-C(O) | 1 | Bd 3-Ar$_1$ | |
| 1.383 | C$_6$H$_3$-4-Cl | C$_6$H$_4$-2-CF$_3$ | O | 4-C(O) | 1 | 3-C(O) | |
| 1.384 | C$_6$H$_3$-4-Cl | C$_6$H$_4$-2-CF$_3$ | O | 4-C(O) | 1 | 3-S(O$_2$) | |
| 1.385 | C$_6$H$_4$-4-Cl | C$_6$H$_4$-2-CF$_3$ | O | 3-C(O) | 0 | | |
| 1.386 | C$_6$H$_3$-4-Cl | C$_6$H$_4$-2-CF$_3$ | O | 3-C(O) | 1 | Bd 4-Ar$_1$ | |
| 1.387 | C$_6$H$_3$-4-Cl | C$_6$H$_4$-2-CF$_3$ | O | 3-C(O) | 1 | 4-S(O$_2$) | |
| 1.388 | C$_6$H$_4$-4-Cl | C$_6$H$_4$-2-CF$_3$ | O | 2-C(O) | 0 | | |
| 1.389 | C$_6$H$_3$-4-Cl | C$_6$H$_4$-2-CF$_3$ | O | 2-C(O) | 1 | Bd 3-Ar$_1$ | |
| 1.390 | C$_6$H$_3$-4-Cl | C$_6$H$_4$-2-CF$_3$ | O | 2-C(O) | 1 | 3-C(O) | |
| 1.391 | C$_6$H$_3$-4-Cl | C$_6$H$_4$-2-CF$_3$ | O | 2-C(O) | 1 | 3-S(O$_2$) | |
| 1.392 | C$_6$H$_4$-4-Cl | C$_6$H$_4$-2-CF$_3$ | S | 4-CH$_2$ | 0 | | |
| 1.393 | C$_6$H$_4$-4-Cl | C$_6$H$_4$-2-CF$_3$ | S | 3-CH$_2$ | 0 | | |
| 1.394 | C$_6$H$_4$-4-Cl | C$_6$H$_4$-2-CF$_3$ | S | 2-CH$_2$ | 0 | | |

TABLE 1-continued

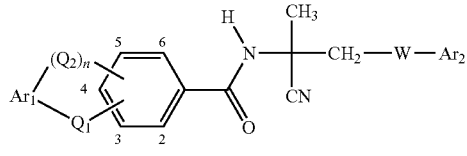

| No. | Ar$_1$ | Ar$_2$ | W | Q$_1$ | n | Q$_2$ | phys. data |
|---|---|---|---|---|---|---|---|
| 1.395 | C$_6$H$_4$-4-Cl | C$_6$H$_4$-2-CF$_3$ | S | 4-OCH$_2$ | 0 | | |
| 1.396 | C$_6$H$_4$-4-Cl | C$_6$H$_4$-2-CF$_3$ | S | 3-OCH$_2$ | 0 | | |
| 1.397 | C$_6$H$_4$-4-Cl | C$_6$H$_4$-2-CF$_3$ | S | 2-OCH$_2$ | 0 | | |
| 1.398 | C$_6$H$_4$-4-Cl | C$_6$H$_4$-2-CF$_3$ | S | 4-S | 0 | | |
| 1.399 | C$_6$H$_4$-4-Cl | C$_6$H$_4$-2-CF$_3$ | S | 3-S | 0 | | |
| 1.400 | C$_6$H$_4$-4-Cl | C$_6$H$_4$-2-CF$_3$ | S | 2-S | 0 | | |
| 1.401 | C$_6$H$_4$-4-Cl | C$_6$H$_4$-2-CF$_3$ | S | 4-S(O) | 0 | | |
| 1.402 | C$_6$H$_4$-4-Cl | C$_6$H$_4$-2-CF$_3$ | S | 3-S(O) | 0 | | |
| 1.403 | C$_6$H$_4$-4-Cl | C$_6$H$_4$-2-CF$_3$ | S | 2-S(O) | 0 | | |
| 1.404 | C$_6$H$_4$-4-Cl | C$_6$H$_4$-2-CF$_3$ | S | 4-C(O) | 0 | | |
| 1.405 | C$_6$H$_3$-4-Cl | C$_6$H$_4$-2-CF$_3$ | S | 4-C(O) | 1 | Bd 3-Ar$_1$ | |
| 1.406 | C$_6$H$_3$-4-Cl | C$_6$H$_4$-2-CF$_3$ | S | 4-C(O) | 1 | 3-C(O) | |
| 1.407 | C$_5$H$_3$-4-Cl | C$_6$H$_4$-2-CF$_3$ | S | 4-C(O) | 1 | 3-S(O$_2$) | |
| 1.408 | C$_6$H$_4$-4-Cl | C$_6$H$_4$-2-CF$_3$ | S | 3-C(O) | 0 | | |
| 1.409 | C$_6$H$_3$-4-Cl | C$_6$H$_4$-2-CF$_3$ | S | 3-C(O) | 1 | Bd 4-Ar$_1$ | |
| 1.410 | C$_6$H$_3$-4-Cl | C$_6$H$_4$-2-CF$_3$ | S | 3-C(O) | 1 | 4-S(O$_2$) | |
| 1.411 | C$_6$H$_4$-4-Cl | C$_6$H$_4$-2-CF$_3$ | S | 2-C(O) | 0 | | |
| 1.412 | C$_6$H$_3$-4-Cl | C$_6$H$_4$-2-CF$_3$ | S | 2-C(O) | 1 | Bd 3-Ar$_1$ | |
| 1.413 | C$_6$H$_3$-4-Cl | C$_6$H$_4$-2-CF$_3$ | S | 2-C(O) | 1 | 3-C(O) | |
| 1.414 | C$_6$H$_3$-4-Cl | C$_6$H$_4$-2-CF$_3$ | S | 2-C(O) | 1 | 3-S(O$_2$) | |
| 1.415 | C$_6$H$_4$-4-CH$_3$ | C$_6$H$_5$ | O | 4-CH$_2$ | 0 | | |
| 1.416 | C$_6$H$_4$-4-CH$_3$ | C$_6$H$_5$ | O | 3-CH$_2$ | 0 | | |
| 1.417 | C$_6$H$_4$-4-CH$_3$ | C$_6$H$_5$ | O | 2-CH$_2$ | 0 | | |
| 1.418 | C$_6$H$_4$-4-CH$_3$ | C$_6$H$_5$ | O | 4-OCH$_2$ | 0 | | |
| 1.419 | C$_6$H$_4$-4-CH$_3$ | C$_6$H$_5$ | O | 3-OCH$_2$ | 0 | | |
| 1.420 | C$_6$H$_4$-4-CH$_3$ | C$_6$H$_5$ | O | 2-OCH$_2$ | 0 | | |
| 1.421 | C$_6$H$_4$-4-CH$_3$ | C$_6$H$_5$ | O | 4-S | 0 | | |
| 1.422 | C$_6$H$_4$-4-CH$_3$ | C$_6$H$_5$ | O | 3-S | 0 | | |
| 1.423 | C$_6$H$_4$-4-CH$_3$ | C$_6$H$_5$ | O | 2-S | 0 | | |
| 1.424 | C$_6$H$_4$-4-CH$_3$ | C$_6$H$_5$ | O | 4-S(O) | 0 | | |
| 1.425 | C$_6$H$_4$-4-CH$_3$ | C$_6$H$_5$ | O | 3-S(O) | 0 | | |
| 1.426 | C$_6$H$_4$-4-CH$_3$ | C$_6$H$_5$ | O | 2-S(O) | 0 | | |
| 1.427 | C$_6$H$_4$-4-CH$_3$ | C$_6$H$_5$ | O | 4-C(O) | 0 | | |
| 1.428 | C$_6$H$_3$-4-CH$_3$ | C$_6$H$_5$ | O | 4-C(O) | 1 | Bd 3-Ar$_1$ | |
| 1.429 | C$_6$H$_3$-4-CH$_3$ | C$_6$H$_5$ | O | 4-C(O) | 1 | 3-C(O) | |
| 1.430 | C$_6$H$_3$-4-CH$_3$ | C$_6$H$_5$ | O | 4-C(O) | 1 | 3-S(O$_2$) | |
| 1.431 | C$_6$H$_4$-4-CH$_3$ | C$_6$H$_5$ | O | 3-C(O) | 0 | | |
| 1.432 | C$_6$H$_3$-4-CH$_3$ | C$_6$H$_5$ | O | 3-C(O) | 1 | Bd 4-Ar$_1$ | |
| 1.433 | C$_6$H$_3$-4-CH$_3$ | C$_6$H$_5$ | O | 3-C(O) | 1 | 4-S(O$_2$) | |
| 1.434 | C$_6$H$_4$-4-CH$_3$ | C$_6$H$_5$ | O | 2-C(O) | 0 | | |
| 1.435 | C$_6$H$_3$-4-CH$_3$ | C$_6$H$_5$ | O | 2-C(O) | 1 | Bd 3-Ar$_1$ | |
| 1.436 | C$_6$H$_3$-4-CH$_3$ | C$_6$H$_5$ | O | 2-C(O) | 1 | 3-C(O) | |
| 1.437 | C$_6$H$_3$-4-CH$_3$ | C$_6$H$_5$ | O | 2-C(O) | 1 | 3-S(O$_2$) | |
| 1.438 | C$_6$H$_4$-4-CH$_3$ | C$_6$H$_5$ | S | 4-CH$_2$ | 0 | | |
| 1.439 | C$_6$H$_4$-4-CH$_3$ | C$_6$H$_5$ | S | 3-CH$_2$ | 0 | | |
| 1.440 | C$_6$H$_4$-4-CH$_3$ | C$_6$H$_5$ | S | 2-CH$_2$ | 0 | | |
| 1.441 | C$_6$H$_4$-4-CH$_3$ | C$_6$H$_5$ | S | 4-OCH$_2$ | 0 | | |
| 1.442 | C$_6$H$_4$-4-CH$_3$ | C$_6$H$_5$ | S | 3-OCH$_2$ | 0 | | |
| 1.443 | C$_6$H$_4$-4-CH$_3$ | C$_6$H$_5$ | S | 2-OCH$_2$ | 0 | | |
| 1.444 | C$_6$H$_4$-4-CH$_3$ | C$_6$H$_5$ | S | 4-S | 0 | | |
| 1.445 | C$_6$H$_4$-4-CH$_3$ | C$_6$H$_5$ | S | 3-S | 0 | | |
| 1.446 | C$_6$H$_4$-4-CH$_3$ | C$_6$H$_5$ | S | 2-S | 0 | | |
| 1.447 | C$_6$H$_4$-4-CH$_3$ | C$_6$H$_5$ | S | 4-S(O) | 0 | | |
| 1.448 | C$_6$H$_4$-4-CH$_3$ | C$_6$H$_5$ | S | 3-S(O) | 0 | | |
| 1.449 | C$_6$H$_4$-4-CH$_3$ | C$_6$H$_5$ | S | 2-S(O) | 0 | | |
| 1.450 | C$_6$H$_4$-4-CH$_3$ | C$_6$H$_5$ | S | 4-C(O) | 0 | | |
| 1.451 | C$_6$H$_3$-4-CH$_3$ | C$_6$H$_5$ | S | 4-C(O) | 1 | Bd 3-Ar$_1$ | |
| 1.452 | C$_6$H$_3$-4-CH$_3$ | C$_6$H$_5$ | S | 4-C(O) | 1 | 3-C(O) | |
| 1.453 | C$_6$H$_3$-4-CH$_3$ | C$_6$H$_5$ | S | 4-C(O) | 1 | 3-S(O$_2$) | |
| 1.454 | C$_6$H$_3$-4-CH$_3$ | C$_6$H$_5$ | S | 3-C(O) | 0 | | |
| 1.455 | C$_6$H$_3$-4-CH$_3$ | C$_6$H$_5$ | S | 3-C(O) | 1 | Bd 4-Ar$_1$ | |
| 1.456 | C$_6$H$_3$-4-CH$_3$ | C$_6$H$_5$ | S | 3-C(O) | 1 | 4-S(O$_2$) | |
| 1.457 | C$_6$H$_3$-4-CH$_3$ | C$_6$H$_5$ | S | 2-C(O) | 0 | | |
| 1.458 | C$_6$H$_3$-4-CH$_3$ | C$_6$H$_5$ | S | 2-C(O) | 1 | Bd 3-Ar$_1$ | |
| 1.459 | C$_6$H$_3$-4-CH$_3$ | C$_6$H$_5$ | S | 2-C(O) | 1 | 3-C(O) | |
| 1.460 | C$_6$H$_3$-4-CH$_3$ | C$_6$H$_5$ | S | 2-C(O) | 1 | 3-S(O$_2$) | |
| 1.461 | C$_6$H$_4$-4-CH$_3$ | C$_6$H$_4$-2-Cl | O | 4-CH$_2$ | 0 | | |
| 1.462 | C$_6$H$_4$-4-CH$_3$ | C$_6$H$_4$-2-Cl | O | 3-CH$_2$ | 0 | | |

TABLE 1-continued

[Structure diagram: Ar₁ connected via (Q₂)ₙ and Q₁ to a benzene ring (positions 2,3,4,5,6) bearing a C(O)-NH-C(CH₃)(CN)-CH₂-W-Ar₂ group]

| No. | Ar₁ | Ar₂ | W | Q₁ | n | Q₂ | phys. data |
|---|---|---|---|---|---|---|---|
| 1.463 | C₆H₄-4-CH₃ | C₆H₄-2-Cl | O | 2-CH₂ | 0 | | |
| 1.464 | C₆H₄-4-CH₃ | C₆H₄-2-Cl | O | 4-OCH₂ | 0 | | |
| 1.465 | C₆H₄-4-CH₃ | C₆H₄-2-Cl | O | 3-OCH₂ | 0 | | |
| 1.466 | C₆H₄-4-CH₃ | C₆H₄-2-Cl | O | 2-OCH₂ | 0 | | |
| 1.467 | C₆H₄-4-CH₃ | C₆H₄-2-Cl | O | 4-S | 0 | | |
| 1.468 | C₆H₄-4-CH₃ | C₆H₄-2-Cl | O | 3-S | 0 | | |
| 1.469 | C₆H₄-4-CH₃ | C₆H₄-2-Cl | O | 2-S | 0 | | |
| 1.470 | C₆H₄-4-CH₃ | C₆H₄-2-Cl | O | 4-S(O) | 0 | | |
| 1.471 | C₆H₄-4-CH₃ | C₆H₄-2-Cl | O | 3-S(O) | 0 | | |
| 1.472 | C₆H₄-4-CH₃ | C₆H₄-2-Cl | O | 2-S(O) | 0 | | |
| 1.473 | C₆H₄-4-CH₃ | C₆H₄-2-Cl | O | 4-C(O) | 0 | | |
| 1.474 | C₆H₃-4-CH₃ | C₆H₄-2-Cl | O | 4-C(O) | 1 | Bd 3-Ar₁ | |
| 1.475 | C₆H₃-4-CH₃ | C₆H₄-2-Cl | O | 4-C(O) | 1 | 3-C(O) | |
| 1.476 | C₆H₃-4-CH₃ | C₆H₄-2-Cl | O | 4-C(O) | 1 | 3-S(O₂) | |
| 1.477 | C₆H₄-4-CH₃ | C₆H₄-2-Cl | O | 3-C(O) | 0 | | |
| 1.478 | C₆H₃-4-CH₃ | C₆H₄-2-Cl | O | 3-C(O) | 1 | Bd 4-Ar₁ | |
| 1.479 | C₆H₃-4-CH₃ | C₆H₄-2-Cl | O | 3-C(O) | 1 | 4-S(O₂) | |
| 1.480 | C₆H₄-4-CH₃ | C₆H₄-2-Cl | O | 2-C(O) | 0 | | |
| 1.481 | C₆H₃-4-CH₃ | C₆H₄-2-Cl | O | 2-C(O) | 1 | Bd 3-Ar₁ | |
| 1.482 | C₆H₃-4-CH₃ | C₆H₄-2-Cl | O | 2-C(O) | 1 | 3-C(O) | |
| 1.483 | C₆H₃-4-CH₃ | C₆H₄-2-Cl | O | 2-C(O) | 1 | 3-S(O₂) | |
| 1.484 | C₆H₄-4-CH₃ | C₆H₄-2-Cl | S | 4-CH₂ | 0 | | |
| 1.485 | C₆H₄-4-CH₃ | C₆H₄-2-Cl | S | 3-CH₂ | 0 | | |
| 1.486 | C₆H₄-4-CH₃ | C₆H₄-2-Cl | S | 2-CH₂ | 0 | | |
| 1.487 | C₆H₄-4-CH₃ | C₆H₄-2-Cl | S | 4-OCH₂ | 0 | | |
| 1.488 | C₆H₄-4-CH₃ | C₆H₄-2-Cl | S | 3-OCH₂ | 0 | | |
| 1.489 | C₆H₄-4-CH₃ | C₆H₄-2-Cl | S | 2-OCH₂ | 0 | | |
| 1.490 | C₆H₄-4-CH₃ | C₆H₄-2-Cl | S | 4-S | 0 | | |
| 1.491 | C₆H₄-4-CH₃ | C₆H₄-2-Cl | S | 3-S | 0 | | |
| 1.492 | C₆H₄-4-CH₃ | C₆H₄-2-Cl | S | 2-S | 0 | | |
| 1.493 | C₆H₄-4-CH₃ | C₆H₄-2-Cl | S | 4-S(O) | 0 | | |
| 1.494 | C₆H₄-4-CH₃ | C₆H₄-2-Cl | S | 3-S(O) | 0 | | |
| 1.495 | C₆H₄-4-CH₃ | C₆H₄-2-Cl | S | 2-S(O) | 0 | | |
| 1.496 | C₆H₄-4-CH₃ | C₆H₄-2-Cl | S | 4-C(O) | 0 | | |
| 1.497 | C₆H₃-4-CH₃ | C₆H₄-2-Cl | S | 4-C(O) | 1 | Bd 3-Ar₁ | |
| 1.498 | C₆H₃-4-CH₃ | C₆H₄-2-Cl | S | 4-C(O) | 1 | 3-C(O) | |
| 1.499 | C₆H₃-4-CH₃ | C₆H₄-2-Cl | S | 4-C(O) | 1 | 3-S(O₂) | |
| 1.500 | C₆H₄-4-CH₃ | C₆H₄-2-Cl | S | 3-C(O) | 0 | | |
| 1.501 | C₆H₃-4-CH₃ | C₆H₄-2-Cl | S | 3-C(O) | 1 | Bd 4-Ar₁ | |
| 1.502 | C₆H₃-4-CH₃ | C₆H₄-2-Cl | S | 3-C(O) | 1 | 4-S(O₂) | |
| 1.503 | C₆H₄-4-CH₃ | C₆H₄-2-Cl | S | 2-C(O) | 0 | | |
| 1.504 | C₆H₃-4-CH₃ | C₆H₄-2-Cl | S | 2-C(O) | 1 | Bd 3-Ar₁ | |
| 1.505 | C₆H₃-4-CH₃ | C₆H₄-2-Cl | S | 2-C(O) | 1 | 3-C(O) | |
| 1.506 | C₆H₃-4-CH₃ | C₆H₄-2-Cl | S | 2-C(O) | 1 | 3-S(O₂) | |
| 1.507 | C₆H₄-4-CH₃ | C₆H₄-2-CF₃ | O | 4-CH₂ | 0 | | |
| 1.508 | C₆H₄-4-CH₃ | C₆H₄-2-CF₃ | O | 3-CH₂ | 0 | | |
| 1.509 | C₆H₄-4-CH₃ | C₆H₄-2-CF₃ | O | 2-CH₂ | 0 | | |
| 1.510 | C₆H₄-4-CH₃ | C₆H₄-2-CF₃ | O | 4-OCH₂ | 0 | | |
| 1.511 | C₆H₄-4-CH₃ | C₆H₄-2-CF₃ | O | 3-OCH₂ | 0 | | |
| 1.512 | C₆H₄-4-CH₃ | C₆H₄-2-CF₃ | O | 2-OCH₂ | 0 | | |
| 1.513 | C₆H₄-4-CH₃ | C₆H₄-2-CF₃ | O | 4-S | 0 | | |
| 1.514 | C₆H₄-4-CH₃ | C₆H₄-2-CF₃ | O | 3-S | 0 | | |
| 1.515 | C₆H₄-4-CH₃ | C₆H₄-2-CF₃ | O | 2-S | 0 | | |
| 1.516 | C₆H₄-4-CH₃ | C₆H₄-2-CF₃ | O | 4-S(O) | 0 | | |
| 1.517 | C₆H₄-4-CH₃ | C₆H₄-2-CF₃ | O | 3-S(O) | 0 | | |
| 1.518 | C₆H₄-4-CH₃ | C₆H₄-2-CF₃ | O | 2-S(O) | 0 | | |
| 1.519 | C₆H₄-4-CH₃ | C₆H₄-2-CF₃ | O | 4-C(O) | 0 | | |
| 1.520 | C₆H₃-4-CH₃ | C₆H₄-2-CF₃ | O | 4-C(O) | 1 | Bd 3-Ar₁ | |
| 1.521 | C₆H₃-4-CH₃ | C₆H₄-2-CF₃ | O | 4-C(O) | 1 | 3-C(O) | |
| 1.522 | C₆H₃-4-CH₃ | C₆H₄-2-CF₃ | O | 4-C(O) | 1 | 3-S(O₂) | |
| 1.523 | C₆H₄-4-CH₃ | C₆H₄-2-CF₃ | O | 3-C(O) | 0 | | |
| 1.524 | C₆H₃-4-CH₃ | C₆H₄-2-CF₃ | O | 3-C(O) | 1 | Bd 4-Ar₁ | |
| 1.525 | C₆H₃-4-CH₃ | C₆H₄-2-CF₃ | O | 3-C(O) | 1 | 4-S(O₂) | |
| 1.526 | C₆H₄-4-CH₃ | C₆H₄-2-CF₃ | O | 2-C(O) | 0 | | |
| 1.527 | C₆H₃-4-CH₃ | C₆H₄-2-CF₃ | O | 2-C(O) | 1 | Bd 3-Ar₁ | |
| 1.528 | C₆H₃-4-CH₃ | C₆H₄-2-CF₃ | O | 2-C(O) | 1 | 3-C(O) | |
| 1.529 | C₆H₃-4-CH₃ | C₆H₄-2-CF₃ | O | 2-C(O) | 1 | 3-S(O₂) | |
| 1.530 | C₆H₄-4-CH₃ | C₆H₄-2-CF₃ | S | 4-CH₂ | 0 | | |

TABLE 1-continued

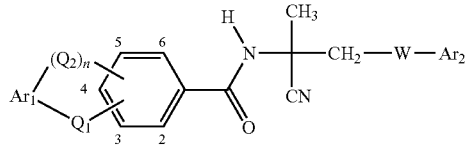

| No. | Ar$_1$ | Ar$_2$ | W | Q$_1$ | n | Q$_2$ | phys. data |
|---|---|---|---|---|---|---|---|
| 1.531 | C$_6$H$_4$-4-CH$_3$ | C$_6$H$_4$-2-CF$_3$ | S | 3-CH$_2$ | 0 | | |
| 1.532 | C$_6$H$_4$-4-CH$_3$ | C$_6$H$_4$-2-CF$_3$ | S | 2-CH$_2$ | 0 | | |
| 1.533 | C$_6$H$_4$-4-CH$_3$ | C$_6$H$_4$-2-CF$_3$ | S | 4-OCH$_2$ | 0 | | |
| 1.534 | C$_6$H$_4$-4-CH$_3$ | C$_6$H$_4$-2-CF$_3$ | S | 3-OCH$_2$ | 0 | | |
| 1.535 | C$_6$H$_4$-4-CH$_3$ | C$_6$H$_4$-2-CF$_3$ | S | 2-OCH$_2$ | 0 | | |
| 1.536 | C$_6$H$_4$-4-CH$_3$ | C$_6$H$_4$-2-CF$_3$ | S | 4-S | 0 | | |
| 1.537 | C$_6$H$_4$-4-CH$_3$ | C$_6$H$_4$-2-CF$_3$ | S | 3-S | 0 | | |
| 1.538 | C$_6$H$_4$-4-CH$_3$ | C$_6$H$_4$-2-CF$_3$ | S | 2-S | 0 | | |
| 1.539 | C$_6$H$_4$-4-CH$_3$ | C$_6$H$_4$-2-CF$_3$ | S | 4-S(O) | 0 | | |
| 1.540 | C$_6$H$_4$-4-CH$_3$ | C$_6$H$_4$-2-CF$_3$ | S | 3-S(O) | 0 | | |
| 1.541 | C$_6$H$_4$-4-CH$_3$ | C$_6$H$_4$-2-CF$_3$ | S | 2-S(O) | 0 | | |
| 1.542 | C$_6$H$_4$-4-CH$_3$ | C$_6$H$_4$-2-CF$_3$ | S | 4-C(O) | 0 | | |
| 1.543 | C$_6$H$_3$-4-CH$_3$ | C$_6$H$_4$-2-CF$_3$ | S | 4-C(O) | 1 | Bd 3-Ar$_1$ | |
| 1.544 | C$_6$H$_3$-4-CH$_3$ | C$_6$H$_4$-2-CF$_3$ | S | 4-C(O) | 1 | 3-C(O) | |
| 1.545 | C$_6$H$_3$-4-CH$_3$ | C$_6$H$_4$-2-CF$_3$ | S | 4-C(O) | 1 | 3-S(O$_2$) | |
| 1.546 | C$_6$H$_4$-4-CH$_3$ | C$_6$H$_4$-2-CF$_3$ | S | 3-C(O) | 0 | | |
| 1.547 | C$_6$H$_3$-4-CH$_3$ | C$_6$H$_4$-2-CF$_3$ | S | 3-C(O) | 1 | Bd 4-Ar$_1$ | |
| 1.548 | C$_6$H$_3$-4-CH$_3$ | C$_6$H$_4$-2-CF$_3$ | S | 3-C(O) | 1 | 4-S(O$_2$) | |
| 1.549 | C$_6$H$_4$-4-CH$_3$ | C$_6$H$_4$-2-CF$_3$ | S | 2-C(O) | 0 | | |
| 1.550 | C$_6$H$_3$-4-CH$_3$ | C$_6$H$_4$-2-CF$_3$ | S | 2-C(O) | 1 | Bd 3-Ar$_1$ | |
| 1.551 | C$_6$H$_3$-4-CH$_3$ | C$_6$H$_4$-2-CF$_3$ | S | 2-C(O) | 1 | 3-C(O) | |
| 1.552 | C$_6$H$_3$-4-CH$_3$ | C$_6$H$_4$-2-CF$_3$ | S | 2-C(O) | 1 | 3-S(O$_2$) | |
| 1.553 | C$_6$H$_4$-4-OCH$_3$ | C$_6$H$_5$ | O | 4-CH$_2$ | 0 | | |
| 1.554 | C$_6$H$_4$-4-OCH$_3$ | C$_6$H$_5$ | O | 3-CH$_2$ | 0 | | |
| 1.555 | C$_6$H$_4$-4-OCH$_3$ | C$_6$H$_5$ | O | 2-CH$_2$ | 0 | | |
| 1.556 | C$_6$H$_4$-4-OCH$_3$ | C$_6$H$_5$ | O | 4-OCH$_2$ | 0 | | |
| 1.557 | C$_6$H$_4$-4-OCH$_3$ | C$_6$H$_5$ | O | 3-OCH$_2$ | 0 | | |
| 1.558 | C$_6$H$_4$-4-OCH$_3$ | C$_6$H$_5$ | O | 2-OCH$_2$ | 0 | | |
| 1.559 | C$_6$H$_4$-4-OCH$_3$ | C$_6$H$_5$ | O | 4-S | 0 | | |
| 1.560 | C$_6$H$_4$-4-OCH$_3$ | C$_6$H$_5$ | O | 3-S | 0 | | |
| 1.561 | C$_6$H$_4$-4-OCH$_3$ | C$_6$H$_5$ | O | 2-S | 0 | | |
| 1.562 | C$_6$H$_4$-4-OCH$_3$ | C$_6$H$_5$ | O | 4-S(O) | 0 | | |
| 1.563 | C$_6$H$_4$-4-OCH$_3$ | C$_6$H$_5$ | O | 3-S(O) | 0 | | |
| 1.564 | C$_6$H$_4$-4-OCH$_3$ | C$_6$H$_5$ | O | 2-S(O) | 0 | | |
| 1.565 | C$_6$H$_4$-4-OCH$_3$ | C$_6$H$_5$ | O | 4-C(O) | 0 | | |
| 1.566 | C$_6$H$_3$-4-OCH$_3$ | C$_6$H$_5$ | O | 4-C(O) | 1 | Bd 3-Ar$_1$ | |
| 1.567 | C$_6$H$_3$-4-OCH$_3$ | C$_6$H$_5$ | O | 4-C(O) | 1 | 3-C(O) | |
| 1.568 | C$_6$H$_3$-4-OCH$_3$ | C$_6$H$_5$ | O | 4-C(O) | 1 | 3-S(O$_2$) | |
| 1.569 | C$_6$H$_4$-4-OCH$_3$ | C$_6$H$_5$ | O | 3-C(O) | 0 | | |
| 1.570 | C$_6$H$_3$-4-OCH$_3$ | C$_6$H$_5$ | O | 3-C(O) | 1 | Bd 4-Ar$_1$ | |
| 1.571 | C$_6$H$_3$-4-OCH$_3$ | C$_6$H$_5$ | O | 3-C(O) | 1 | 4-S(O$_2$) | |
| 1.572 | C$_6$H$_4$-4-OCH$_3$ | C$_6$H$_5$ | O | 2-C(O) | 0 | | |
| 1.573 | C$_6$H$_3$-4-OCH$_3$ | C$_6$H$_5$ | O | 2-C(O) | 1 | Bd 3-Ar$_1$ | |
| 1.574 | C$_6$H$_3$-4-OCH$_3$ | C$_6$H$_5$ | O | 2-C(O) | 1 | 3-C(O) | |
| 1.575 | C$_6$H$_3$-4-OCH$_3$ | C$_6$H$_5$ | O | 2-C(O) | 1 | 3-S(O$_2$) | |
| 1.576 | C$_6$H$_4$-4-OCH$_3$ | C$_6$H$_5$ | S | 4-CH$_2$ | 0 | | |
| 1.577 | C$_6$H$_4$-4-OCH$_3$ | C$_6$H$_5$ | S | 3-CH$_2$ | 0 | | |
| 1.578 | C$_6$H$_4$-4-OCH$_3$ | C$_6$H$_5$ | S | 2-CH$_2$ | 0 | | |
| 1.579 | C$_6$H$_4$-4-OCH$_3$ | C$_6$H$_5$ | S | 4-OCH$_2$ | 0 | | |
| 1.580 | C$_6$H$_4$-4-OCH$_3$ | C$_6$H$_5$ | S | 3-OCH$_2$ | 0 | | |
| 1.581 | C$_6$H$_4$-4-OCH$_3$ | C$_6$H$_5$ | S | 2-OCH$_2$ | 0 | | |
| 1.582 | C$_6$H$_4$-4-OCH$_3$ | C$_6$H$_5$ | S | 4-S | 0 | | |
| 1.583 | C$_6$H$_4$-4-OCH$_3$ | C$_6$H$_5$ | S | 3-S | 0 | | |
| 1.584 | C$_6$H$_4$-4-OCH$_3$ | C$_6$H$_5$ | S | 2-S | 0 | | |
| 1.585 | C$_6$H$_4$-4-OCH$_3$ | C$_6$H$_5$ | S | 4-S(O) | 0 | | |
| 1.586 | C$_6$H$_4$-4-OCH$_3$ | C$_6$H$_5$ | S | 3-S(O) | 0 | | |
| 1.587 | C$_6$H$_4$-4-OCH$_3$ | C$_6$H$_5$ | S | 2-S(O) | 0 | | |
| 1.588 | C$_6$H$_4$-4-OCH$_3$ | C$_6$H$_5$ | S | 4-C(O) | 0 | | |
| 1.589 | C$_6$H$_3$-4-OCH$_3$ | C$_6$H$_5$ | S | 4-C(O) | 1 | Bd 3-Ar$_1$ | |
| 1.590 | C$_6$H$_3$-4-OCH$_3$ | C$_6$H$_5$ | S | 4-C(O) | 1 | 3-C(O) | |
| 1.591 | C$_6$H$_3$-4-OCH$_3$ | C$_6$H$_5$ | S | 4-C(O) | 1 | 3-S(O$_2$) | |
| 1.592 | C$_6$H$_4$-4-OCH$_3$ | C$_6$H$_5$ | S | 3-C(O) | 0 | | |
| 1.593 | C$_6$H$_3$-4-OCH$_3$ | C$_6$H$_5$ | S | 3-C(O) | 1 | Bd 4-Ar$_1$ | |
| 1.594 | C$_6$H$_3$-4-OCH$_3$ | C$_6$H$_5$ | S | 3-C(O) | 1 | 4-S(O$_2$) | |
| 1.595 | C$_6$H$_4$-4-OCH$_3$ | C$_6$H$_5$ | S | 2-C(O) | 0 | | |
| 1.596 | C$_6$H$_3$-4-OCH$_3$ | C$_6$H$_5$ | S | 2-C(O) | 1 | Bd 3-Ar$_1$ | |
| 1.597 | C$_6$H$_3$-4-OCH$_3$ | C$_6$H$_5$ | S | 2-C(O) | 1 | 3-C(O) | |
| 1.598 | C$_6$H$_3$-4-OCH$_3$ | C$_6$H$_5$ | S | 2-C(O) | 1 | 3-S(O$_2$) | |

TABLE 1-continued

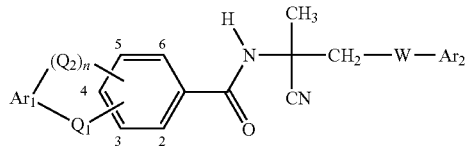

| No. | Ar$_1$ | Ar$_2$ | W | Q$_1$ | n | Q$_2$ | phys. data |
|---|---|---|---|---|---|---|---|
| 1.599 | C$_6$H$_4$-4-OCH$_3$ | C$_6$H$_4$-2-Cl | O | 4-CH$_2$ | 0 | | |
| 1.600 | C$_6$H$_4$-4-OCH$_3$ | C$_6$H$_4$-2-Cl | O | 3-CH$_2$ | 0 | | |
| 1.601 | C$_6$H$_4$-4-OCH$_3$ | C$_6$H$_4$-2-Cl | O | 2-CH$_2$ | 0 | | |
| 1.602 | C$_6$H$_4$-4-OCH$_3$ | C$_6$H$_4$-2-Cl | O | 4-OCH$_2$ | 0 | | |
| 1.603 | C$_6$H$_4$-4-OCH$_3$ | C$_6$H$_4$-2-Cl | O | 3-OCH$_2$ | 0 | | |
| 1.604 | C$_6$H$_4$-4-OCH$_3$ | C$_6$H$_4$-2-Cl | O | 2-OCH$_2$ | 0 | | |
| 1.605 | C$_6$H$_4$-4-OCH$_3$ | C$_6$H$_4$-2-Cl | O | 4-S | 0 | | |
| 1.606 | C$_6$H$_4$-4-OCH$_3$ | C$_6$H$_4$-2-Cl | O | 3-S | 0 | | |
| 1.607 | C$_5$H$_4$-4-OCH$_3$ | C$_6$H$_4$-2-Cl | O | 2-S | 0 | | |
| 1.608 | C$_6$H$_4$-4-OCH$_3$ | C$_6$H$_4$-2-Cl | O | 4-S(O) | 0 | | |
| 1.609 | C$_6$H$_4$-4-OCH$_3$ | C$_6$H$_4$-2-Cl | O | 3-S(O) | 0 | | |
| 1.610 | C$_6$H$_4$-4-OCH$_3$ | C$_6$H$_4$-2-Cl | O | 2-S(O) | 0 | | |
| 1.611 | C$_6$H$_4$-4-OCH$_3$ | C$_6$H$_4$-2-Cl | O | 4-C(O) | 0 | | |
| 1.612 | C$_6$H$_3$-4-OCH$_3$ | C$_6$H$_4$-2-Cl | O | 4-C(O) | 1 | Bd 3-Ar$_1$ | |
| 1.613 | C$_6$H$_3$-4-OCH$_3$ | C$_6$H$_4$-2-Cl | O | 4-C(O) | 1 | 3-C(O) | |
| 1.614 | C$_6$H$_3$-4-OCH$_3$ | C$_6$H$_4$-2-Cl | O | 4-C(O) | 1 | 3-S(O$_2$) | |
| 1.615 | C$_6$H$_4$-4-OCH$_3$ | C$_6$H$_4$-2-Cl | O | 3-C(O) | 0 | | |
| 1.616 | C$_6$H$_3$-4-OCH$_3$ | C$_6$H$_4$-2-Cl | O | 3-C(O) | 1 | Bd 4-Ar$_1$ | |
| 1.617 | C$_6$H$_3$-4-OCH$_3$ | C$_6$H$_4$-2-Cl | O | 3-C(O) | 1 | 4-S(O$_2$) | |
| 1.618 | C$_6$H$_4$-4-OCH$_3$ | C$_6$H$_4$-2-Cl | O | 2-C(O) | 0 | | |
| 1.619 | C$_6$H$_3$-4-OCH$_3$ | C$_6$H$_4$-2-Cl | O | 2-C(O) | 1 | Bd 3-Ar$_1$ | |
| 1.620 | C$_6$H$_3$-4-OCH$_3$ | C$_6$H$_4$-2-Cl | O | 2-C(O) | 1 | 3-C(O) | |
| 1.621 | C$_6$H$_3$-4-OCH$_3$ | C$_6$H$_4$-2-Cl | O | 2-C(O) | 1 | 3-S(O$_2$) | |
| 1.622 | C$_6$H$_4$-4-OCH$_3$ | C$_6$H$_4$-2-Cl | S | 4-CH$_2$ | 0 | | |
| 1.623 | C$_6$H$_4$-4-OCH$_3$ | C$_6$H$_4$-2-Cl | S | 3-CH$_2$ | 0 | | |
| 1.624 | C$_6$H$_4$-4-OCH$_3$ | C$_6$H$_4$-2-Cl | S | 2-CH$_2$ | 0 | | |
| 1.625 | C$_6$H$_4$-4-OCH$_3$ | C$_6$H$_4$-2-Cl | S | 4-OCH$_2$ | 0 | | |
| 1.626 | C$_6$H$_4$-4-OCH$_3$ | C$_6$H$_4$-2-Cl | S | 3-OCH$_2$ | 0 | | |
| 1.627 | C$_6$H$_4$-4-OCH$_3$ | C$_6$H$_4$-2-Cl | S | 2-OCH$_2$ | 0 | | |
| 1.628 | C$_6$H$_4$-4-OCH$_3$ | C$_6$H$_4$-2-Cl | S | 4-S | 0 | | |
| 1.629 | C$_6$H$_4$-4-OCH$_3$ | C$_6$H$_4$-2-Cl | S | 3-S | 0 | | |
| 1.630 | C$_6$H$_4$-4-OCH$_3$ | C$_6$H$_4$-2-Cl | S | 2-S | 0 | | |
| 1.631 | C$_6$H$_4$-4-OCH$_3$ | C$_6$H$_4$-2-Cl | S | 4-S(O) | 0 | | |
| 1.632 | C$_6$H$_4$-4-OCH$_3$ | C$_6$H$_4$-2-Cl | S | 3-S(O) | 0 | | |
| 1.633 | C$_6$H$_4$-4-OCH$_3$ | C$_6$H$_4$-2-Cl | S | 2-S(O) | 0 | | |
| 1.634 | C$_6$H$_4$-4-OCH$_3$ | C$_6$H$_4$-2-Cl | S | 4-C(O) | 0 | | |
| 1.635 | C$_6$H$_3$-4-OCH$_3$ | C$_6$H$_4$-2-Cl | S | 4-C(O) | 1 | Bd 3-Ar$_1$ | |
| 1.636 | C$_6$H$_3$-4-OCH$_3$ | C$_6$H$_4$-2-Cl | S | 4-C(O) | 1 | 3-C(O) | |
| 1.637 | C$_6$H$_3$-4-OCH$_3$ | C$_6$H$_4$-2-Cl | S | 4-C(O) | 1 | 3-S(O$_2$) | |
| 1.638 | C$_6$H$_4$-4-OCH$_3$ | C$_6$H$_4$-2-Cl | S | 3-C(O) | 0 | | |
| 1.639 | C$_6$H$_3$-4-OCH$_3$ | C$_6$H$_4$-2-Cl | S | 3-C(O) | 1 | Bd 4-Ar$_1$ | |
| 1.640 | C$_6$H$_3$-4-OCH$_3$ | C$_6$H$_4$-2-Cl | S | 3-C(O) | 1 | 4-S(O$_2$) | |
| 1.641 | C$_6$H$_4$-4-OCH$_3$ | C$_6$H$_4$-2-Cl | S | 2-C(O) | 0 | | |
| 1.642 | C$_6$H$_3$-4-OCH$_3$ | C$_6$H$_4$-2-Cl | S | 2-C(O) | 1 | Bd 3-Ar$_1$ | |
| 1.643 | C$_6$H$_3$-4-OCH$_3$ | C$_6$H$_4$-2-Cl | S | 2-C(O) | 1 | 3-C(O) | |
| 1.644 | C$_6$H$_3$-4-OCH$_3$ | C$_6$H$_4$-2-Cl | S | 2-C(O) | 1 | 3-S(O$_2$) | |
| 1.645 | C$_6$H$_4$-4-OCH$_3$ | C$_6$H$_4$-2-CF$_3$ | O | 4-CH$_2$ | 0 | | |
| 1.646 | C$_6$H$_4$-4-OCH$_3$ | C$_6$H$_4$-2-CF$_3$ | O | 3-CH$_2$ | 0 | | |
| 1.647 | C$_6$H$_4$-4-OCH$_3$ | C$_6$H$_4$-2-CF$_3$ | O | 2-CH$_2$ | 0 | | |
| 1.648 | C$_6$H$_4$-4-OCH$_3$ | C$_6$H$_4$-2-CF$_3$ | O | 4-OCH$_2$ | 0 | | |
| 1.649 | C$_6$H$_4$-4-OCH$_3$ | C$_6$H$_4$-2-CF$_3$ | O | 3-OCH$_2$ | 0 | | |
| 1.650 | C$_6$H$_4$-4-OCH$_3$ | C$_6$H$_4$-2-CF$_3$ | O | 2-OCH$_2$ | 0 | | |
| 1.651 | C$_6$H$_4$-4-OCH$_3$ | C$_6$H$_4$-2-CF$_3$ | O | 4-S | 0 | | |
| 1.652 | C$_6$H$_4$-4-OCH$_3$ | C$_6$H$_4$-2-CF$_3$ | O | 3-S | 0 | | |
| 1.653 | C$_6$H$_4$-4-OCH$_3$ | C$_6$H$_4$-2-CF$_3$ | O | 2-S | 0 | | |
| 1.654 | C$_6$H$_4$-4-OCH$_3$ | C$_6$H$_4$-2-CF$_3$ | O | 4-S(O) | 0 | | |
| 1.655 | C$_6$H$_4$-4-OCH$_3$ | C$_6$H$_4$-2-CF$_3$ | O | 3-S(O) | 0 | | |
| 1.656 | C$_6$H$_4$-4-OCH$_3$ | C$_6$H$_4$-2-CF$_3$ | O | 2-S(O) | 0 | | |
| 1.657 | C$_6$H$_4$-4-OCH$_3$ | C$_6$H$_4$-2-CF$_3$ | O | 4-C(O) | 0 | | |
| 1.658 | C$_6$H$_3$-4-OCH$_3$ | C$_6$H$_4$-2-CF$_3$ | O | 4-C(O) | 1 | Bd 3-Ar$_1$ | |
| 1.659 | C$_6$H$_3$-4-OCH$_3$ | C$_6$H$_4$-2-CF$_3$ | O | 4-C(O) | 1 | 3-C(O) | |
| 1.660 | C$_6$H$_3$-4-OCH$_3$ | C$_6$H$_4$-2-CF$_3$ | O | 4-C(O) | 1 | 3-S(O$_2$) | |
| 1.661 | C$_6$H$_4$-4-OCH$_3$ | C$_6$H$_4$-2-CF$_3$ | O | 3-C(O) | 0 | | |
| 1.662 | C$_6$H$_3$-4-OCH$_3$ | C$_6$H$_4$-2-CF$_3$ | O | 3-C(O) | 1 | Bd 4-Ar$_1$ | |
| 1.663 | C$_6$H$_3$-4-OCH$_3$ | C$_6$H$_4$-2-CF$_3$ | O | 3-C(O) | 1 | 4-S(O$_2$) | |
| 1.664 | C$_6$H$_4$-4-OCH$_3$ | C$_6$H$_4$-2-CF$_3$ | O | 2-C(O) | 0 | | |
| 1.665 | C$_6$H$_3$-4-OCH$_3$ | C$_6$H$_4$-2-CF$_3$ | O | 2-C(O) | 1 | Bd 3-Ar$_1$ | |
| 1.666 | C$_6$H$_3$-4-OCH$_3$ | C$_6$H$_4$-2-CF$_3$ | O | 2-C(O) | 1 | 3-C(O) | |

TABLE 1-continued

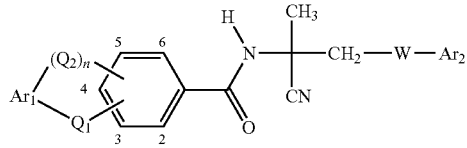

| No. | Ar$_1$ | Ar$_2$ | W | Q$_1$ | n | Q$_2$ | phys. data |
|---|---|---|---|---|---|---|---|
| 1.667 | C$_6$H$_3$-4-OCH$_3$ | C$_6$H$_4$-2-CF$_3$ | O | 2-C(O) | 1 | 3-S(O$_2$) | |
| 1.668 | C$_6$H$_4$-4-OCH$_3$ | C$_6$H$_4$-2-CF$_3$ | S | 4-CH$_2$ | 0 | | |
| 1.669 | C$_6$H$_4$-4-OCH$_3$ | C$_6$H$_4$-2-CF$_3$ | S | 3-CH$_2$ | 0 | | |
| 1.670 | C$_6$H$_4$-4-OCH$_3$ | C$_6$H$_4$-2-CF$_3$ | S | 2-CH$_2$ | 0 | | |
| 1.671 | C$_6$H$_4$-4-OCH$_3$ | C$_6$H$_4$-2-CF$_3$ | S | 4-OCH$_2$ | 0 | | |
| 1.672 | C$_6$H$_4$-4-OCH$_3$ | C$_6$H$_4$-2-CF$_3$ | S | 3-OCH$_2$ | 0 | | |
| 1.673 | C$_6$H$_4$-4-OCH$_3$ | C$_6$H$_4$-2-CF$_3$ | S | 2-OCH$_2$ | 0 | | |
| 1.674 | C$_6$H$_4$-4-OCH$_3$ | C$_6$H$_4$-2-CF$_3$ | S | 4-S | 0 | | |
| 1.675 | C$_6$H$_4$-4-OCH$_3$ | C$_6$H$_4$-2-CF$_3$ | S | 3-S | 0 | | |
| 1.676 | C$_6$H$_4$-4-OCH$_3$ | C$_6$H$_4$-2-CF$_3$ | S | 2-S | 0 | | |
| 1.677 | C$_6$H$_4$-4-OCH$_3$ | C$_6$H$_4$-2-CF$_3$ | S | 4-S(O) | 0 | | |
| 1.678 | C$_6$H$_4$-4-OCH$_3$ | C$_6$H$_4$-2-CF$_3$ | S | 3-S(O) | 0 | | |
| 1.679 | C$_6$H$_4$-4-OCH$_3$ | C$_6$H$_4$-2-CF$_3$ | S | 2-S(O) | 0 | | |
| 1.680 | C$_6$H$_4$-4-OCH$_3$ | C$_6$H$_4$-2-CF$_3$ | S | 4-C(O) | 0 | | |
| 1.681 | C$_6$H$_3$-4-OCH$_3$ | C$_6$H$_4$-2-CF$_3$ | S | 4-C(O) | 1 | Bd 3-Ar$_1$ | |
| 1.682 | C$_6$H$_3$-4-OCH$_3$ | C$_6$H$_4$-2-CF$_3$ | S | 4-C(O) | 1 | 3-C(O) | |
| 1.683 | C$_6$H$_3$-4-OCH$_3$ | C$_6$H$_4$-2-CF$_3$ | S | 4-C(O) | 1 | 3-S(O$_2$) | |
| 1.684 | C$_5$H$_4$-4-OCH$_3$ | C$_6$H$_4$-2-CF$_3$ | S | 3-C(O) | 0 | | |
| 1.685 | C$_6$H$_3$-4-OCH$_3$ | C$_6$H$_4$-2-CF$_3$ | S | 3-C(O) | 1 | Bd 4-Ar$_1$ | |
| 1.686 | C$_6$H$_3$-4-OCH$_3$ | C$_6$H$_4$-2-CF$_3$ | S | 3-C(O) | 1 | 4-S(O$_2$) | |
| 1.687 | C$_6$H$_4$-4-OCH$_3$ | C$_6$H$_4$-2-CF$_3$ | S | 2-C(O) | 0 | | |
| 1.688 | C$_6$H$_3$-4-OCH$_3$ | C$_6$H$_4$-2-CF$_3$ | S | 2-C(O) | 1 | Bd 3-Ar$_1$ | |
| 1.689 | C$_6$H$_3$-4-OCH$_3$ | C$_6$H$_4$-2-CF$_3$ | S | 2-C(O) | 1 | 3-C(O) | |
| 1.690 | C$_6$H$_3$-4-OCH$_3$ | C$_6$H$_4$-2-CF$_3$ | S | 2-C(O) | 1 | 3-S(O$_2$) | |
| 1.691 | C$_6$H$_4$-4-CF$_3$ | C$_6$H$_5$ | O | 4-CH$_2$ | 0 | | |
| 1.692 | C$_6$H$_4$-4-CF$_3$ | C$_6$H$_5$ | O | 3-CH$_2$ | 0 | | |
| 1.693 | C$_6$H$_4$-4-CF$_3$ | C$_6$H$_5$ | O | 2-CH$_2$ | 0 | | |
| 1.694 | C$_6$H$_4$-4-CF$_3$ | C$_6$H$_5$ | O | 4-OCH$_2$ | 0 | | |
| 1.695 | C$_6$H$_4$-4-CF$_3$ | C$_6$H$_5$ | O | 3-OCH$_2$ | 0 | | |
| 1.696 | C$_6$H$_4$-4-CF$_3$ | C$_6$H$_5$ | O | 2-OCH$_2$ | 0 | | |
| 1.697 | C$_6$H$_4$-4-CF$_3$ | C$_6$H$_5$ | O | 4-S | 0 | | |
| 1.698 | C$_6$H$_4$-4-CF$_3$ | C$_6$H$_5$ | O | 3-S | 0 | | |
| 1.699 | C$_6$H$_4$-4-CF$_3$ | C$_6$H$_5$ | O | 2-S | 0 | | |
| 1.700 | C$_6$H$_4$-4-CF$_3$ | C$_6$H$_5$ | O | 4-S(O) | 0 | | |
| 1.701 | C$_6$H$_4$-4-CF$_3$ | C$_6$H$_5$ | O | 3-S(O) | 0 | | |
| 1.702 | C$_6$H$_4$-4-CF$_3$ | C$_6$H$_5$ | O | 2-S(O) | 0 | | |
| 1.703 | C$_6$H$_4$-4-CF$_3$ | C$_6$H$_5$ | O | 4-C(O) | 0 | | m.p. 146° |
| 1.704 | C$_6$H$_3$-4-CF$_3$ | C$_6$H$_5$ | O | 4-C(O) | 1 | Bd 3-Ar$_1$ | |
| 1.705 | C$_6$H$_3$-4-CF$_3$ | C$_6$H$_5$ | O | 4-C(O) | 1 | 3-C(O) | |
| 1.706 | C$_6$H$_3$-4-CF$_3$ | C$_6$H$_5$ | O | 4-C(O) | 1 | 3-S(O$_2$) | |
| 1.707 | C$_6$H$_4$-4-CF$_3$ | C$_6$H$_5$ | O | 3-C(O) | 0 | | |
| 1.708 | C$_6$H$_3$-4-CF$_3$ | C$_6$H$_5$ | O | 3-C(O) | 1 | Bd 4-Ar$_1$ | |
| 1.709 | C$_6$H$_3$-4-CF$_3$ | C$_6$H$_5$ | O | 3-C(O) | 1 | 4-S(O$_2$) | |
| 1.710 | C$_6$H$_4$-4-CF$_3$ | C$_6$H$_5$ | O | 2-C(O) | 0 | | |
| 1.711 | C$_6$H$_3$-4-CF$_3$ | C$_6$H$_5$ | O | 2-C(O) | 1 | Bd 3-Ar$_1$ | |
| 1.712 | C$_6$H$_3$-4-CF$_3$ | C$_6$H$_5$ | O | 2-C(O) | 1 | 3-C(O) | |
| 1.713 | C$_6$H$_3$-4-CF$_3$ | C$_6$H$_5$ | O | 2-C(O) | 1 | 3-S(O$_2$) | |
| 1.714 | C$_5$H$_4$-4-CF$_3$ | C$_6$H$_5$ | S | 4-CH$_2$ | 0 | | |
| 1.715 | C$_6$H$_4$-4-CF$_3$ | C$_6$H$_5$ | S | 3-CH$_2$ | 0 | | |
| 1.716 | C$_6$H$_4$-4-CF$_3$ | C$_6$H$_5$ | S | 2-CH$_2$ | 0 | | |
| 1.717 | C$_6$H$_4$-4-CF$_3$ | C$_6$H$_5$ | S | 4-OCH$_2$ | 0 | | |
| 1.718 | C$_6$H$_4$-4-CF$_3$ | C$_6$H$_5$ | S | 3-OCH$_2$ | 0 | | |
| 1.719 | C$_6$H$_4$-4-CF$_3$ | C$_6$H$_5$ | S | 2-OCH$_2$ | 0 | | |
| 1.720 | C$_6$H$_4$-4-CF$_3$ | C$_6$H$_5$ | S | 4-S | 0 | | |
| 1.721 | C$_6$H$_4$-4-CF$_3$ | C$_6$H$_5$ | S | 3-S | 0 | | |
| 1.722 | C$_6$H$_4$-4-CF$_3$ | C$_6$H$_5$ | S | 2-S | 0 | | |
| 1.723 | C$_6$H$_4$-4-CF$_3$ | C$_6$H$_5$ | S | 4-S(O) | 0 | | |
| 1.724 | C$_6$H$_4$-4-CF$_3$ | C$_6$H$_5$ | S | 3-S(O) | 0 | | |
| 1.725 | C$_6$H$_4$-4-CF$_3$ | C$_6$H$_5$ | S | 2-S(O) | 0 | | |
| 1.726 | C$_6$H$_4$-4-CF$_3$ | C$_6$H$_5$ | S | 4-C(O) | 0 | | |
| 1.727 | C$_6$H$_3$-4-CF$_3$ | C$_6$H$_5$ | S | 4-C(O) | 1 | Bd 3-Ar$_1$ | |
| 1.728 | C$_6$H$_3$-4-CF$_3$ | C$_6$H$_5$ | S | 4-C(O) | 1 | 3-C(O) | |
| 1.729 | C$_6$H$_3$-4-CF$_3$ | C$_6$H$_5$ | S | 4-C(O) | 1 | 3-S(O$_2$) | |
| 1.730 | C$_6$H$_4$-4-CF$_3$ | C$_6$H$_5$ | S | 3-C(O) | 0 | | |
| 1.731 | C$_6$H$_3$-4-CF$_3$ | C$_6$H$_5$ | S | 3-C(O) | 1 | Bd 4-Ar$_1$ | |
| 1.732 | C$_6$H$_3$-4-CF$_3$ | C$_6$H$_5$ | S | 3-C(O) | 1 | 4-S(O$_2$) | |
| 1.733 | C$_6$H$_4$-4-CF$_3$ | C$_6$H$_5$ | S | 2-C(O) | 0 | | |
| 1.734 | C$_6$H$_3$-4-CF$_3$ | C$_6$H$_5$ | S | 2-C(O) | 1 | Bd 3-Ar$_1$ | |

TABLE 1-continued

| No. | Ar$_1$ | Ar$_2$ | W | Q$_1$ | n | Q$_2$ | phys. data |
|---|---|---|---|---|---|---|---|
| 1.735 | C$_6$H$_3$-4-CF$_3$ | C$_6$H$_5$ | S | 2-C(O) | 1 | 3-C(O) | |
| 1.736 | C$_6$H$_3$-4-CF$_3$ | C$_6$H$_5$ | S | 2-C(O) | 1 | 3-S(O$_2$) | |
| 1.737 | C$_6$H$_4$-4-CF$_3$ | C$_6$H$_4$-2-Cl | O | 4-CH$_2$ | 0 | | |
| 1.738 | C$_6$H$_4$-4-CF$_3$ | C$_6$H$_4$-2-Cl | O | 3-CH$_2$ | 0 | | |
| 1.739 | C$_6$H$_4$-4-CF$_3$ | C$_6$H$_4$-2-Cl | O | 2-CH$_2$ | 0 | | |
| 1.740 | C$_6$H$_4$-4-CF$_3$ | C$_6$H$_4$-2-Cl | O | 4-OCH$_2$ | 0 | | |
| 1.741 | C$_6$H$_4$-4-CF$_3$ | C$_6$H$_4$-2-Cl | O | 3-OCH$_2$ | 0 | | |
| 1.742 | C$_6$H$_4$-4-CF$_3$ | C$_6$H$_4$-2-Cl | O | 2-OCH$_2$ | 0 | | |
| 1.743 | C$_6$H$_4$-4-CF$_3$ | C$_6$H$_4$-2-Cl | O | 4-S | 0 | | |
| 1.744 | C$_6$H$_4$-4-CF$_3$ | C$_6$H$_4$-2-Cl | O | 3-S | 0 | | |
| 1.745 | C$_6$H$_4$-4-CF$_3$ | C$_6$H$_4$-2-Cl | O | 2-S | 0 | | |
| 1.746 | C$_6$H$_4$-4-CF$_3$ | C$_6$H$_4$-2-Cl | O | 4-S(O) | 0 | | |
| 1.747 | C$_6$H$_4$-4-CF$_3$ | C$_6$H$_4$-2-Cl | O | 3-S(O) | 0 | | |
| 1.748 | C$_6$H$_4$-4-CF$_3$ | C$_6$H$_4$-2-Cl | O | 2-S(O) | 0 | | |
| 1.749 | C$_6$H$_4$-4-CF$_3$ | C$_6$H$_4$-2-Cl | O | 4-C(O) | 0 | | |
| 1.750 | C$_6$H$_3$-4-CF$_3$ | C$_6$H$_4$-2-Cl | O | 4-C(O) | 1 | Bd 3-Ar$_1$ | |
| 1.751 | C$_6$H$_3$-4-CF$_3$ | C$_6$H$_4$-2-Cl | O | 4-C(O) | 1 | 3-C(O) | |
| 1.752 | C$_6$H$_3$-4-CF$_3$ | C$_6$H$_4$-2-Cl | O | 4-C(O) | 1 | 3-S(O$_2$) | |
| 1.753 | C$_6$H$_4$-4-CF$_3$ | C$_6$H$_4$-2-Cl | O | 3-C(O) | 0 | | |
| 1.754 | C$_6$H$_3$-4-CF$_3$ | C$_6$H$_4$-2-Cl | O | 3-C(O) | 1 | Bd 4-Ar$_1$ | |
| 1.755 | C$_6$H$_3$-4-CF$_3$ | C$_6$H$_4$-2-Cl | O | 3-C(O) | 1 | 4-S(O$_2$) | |
| 1.756 | C$_6$H$_4$-4-CF$_3$ | C$_6$H$_4$-2-Cl | O | 2-C(O) | 0 | | |
| 1.757 | C$_6$H$_3$-4-CF$_3$ | C$_6$H$_4$-2-Cl | O | 2-C(O) | 1 | Bd 3-Ar$_1$ | |
| 1.758 | C$_6$H$_3$-4-CF$_3$ | C$_6$H$_4$-2-Cl | O | 2-C(O) | 1 | 3-C(O) | |
| 1.759 | C$_6$H$_3$-4-CF$_3$ | C$_6$H$_4$-2-Cl | O | 2-C(O) | 1 | 3-S(O$_2$) | |
| 1.760 | C$_6$H$_4$-4-CF$_3$ | C$_6$H$_4$-2-Cl | S | 4-CH$_2$ | 0 | | |
| 1.761 | C$_6$H$_4$-4-CF$_3$ | C$_6$H$_4$-2-Cl | S | 3-CH$_2$ | 0 | | |
| 1.762 | C$_6$H$_4$-4-CF$_3$ | C$_6$H$_4$-2-Cl | S | 2-CH$_2$ | 0 | | |
| 1.763 | C$_6$H$_4$-4-CF$_3$ | C$_6$H$_4$-2-Cl | S | 4-OCH$_2$ | 0 | | |
| 1.764 | C$_6$H$_4$-4-CF$_3$ | C$_6$H$_4$-2-Cl | S | 3-OCH$_2$ | 0 | | |
| 1.765 | C$_6$H$_4$-4-CF$_3$ | C$_6$H$_4$-2-Cl | S | 2-OCH$_2$ | 0 | | |
| 1.766 | C$_6$H$_4$-4-CF$_3$ | C$_6$H$_4$-2-Cl | S | 4-S | 0 | | |
| 1.767 | C$_6$H$_4$-4-CF$_3$ | C$_6$H$_4$-2-Cl | S | 3-S | 0 | | |
| 1.768 | C$_6$H$_4$-4-CF$_3$ | C$_6$H$_4$-2-Cl | S | 2-S | 0 | | |
| 1.769 | C$_6$H$_4$-4-CF$_3$ | C$_5$H$_4$-2-Cl | S | 4-S(O) | 0 | | |
| 1.770 | C$_6$H$_4$-4-CF$_3$ | C$_6$H$_4$-2-Cl | S | 3-S(O) | 0 | | |
| 1.771 | C$_6$H$_4$-4-CF$_3$ | C$_6$H$_4$-2-Cl | S | 2-S(O) | 0 | | |
| 1.772 | C$_6$H$_4$-4-CF$_3$ | C$_5$H$_4$-2-Cl | S | 4-C(O) | 0 | | |
| 1.773 | C$_6$H$_3$-4-CF$_3$ | C$_6$H$_4$-2-Cl | S | 4-C(O) | 1 | Bd 3-Ar$_1$ | |
| 1.774 | C$_6$H$_3$-4-CF$_3$ | C$_6$H$_4$-2-Cl | S | 4-C(O) | 1 | 3-C(O) | |
| 1.775 | C$_6$H$_3$-4-CF$_3$ | C$_6$H$_4$-2-Cl | S | 4-C(O) | 1 | 3-S(O$_2$) | |
| 1.776 | C$_6$H$_4$-4-CF$_3$ | C$_6$H$_4$-2-Cl | S | 3-C(O) | 0 | | |
| 1.777 | C$_6$H$_3$-4-CF$_3$ | C$_6$H$_4$-2-Cl | S | 3-C(O) | 1 | Bd 4-Ar$_1$ | |
| 1.778 | C$_6$H$_3$-4-CF$_3$ | C$_6$H$_4$-2-Cl | S | 3-C(O) | 1 | 4-S(O$_2$) | |
| 1.779 | C$_6$H$_4$-4-CF$_3$ | C$_6$H$_4$-2-Cl | S | 2-C(O) | 0 | | |
| 1.780 | C$_6$H$_3$-4-CF$_3$ | C$_6$H$_4$-2-Cl | S | 2-C(O) | 1 | Bd 3-Ar$_1$ | |
| 1.781 | C$_6$H$_3$-4-CF$_3$ | C$_6$H$_4$-2-Cl | S | 2-C(O) | 1 | 3-C(O) | |
| 1.782 | C$_6$H$_3$-4-CF$_3$ | C$_6$H$_4$-2-Cl | S | 2-C(O) | 1 | 3-S(O$_2$) | |
| 1.783 | C$_6$H$_4$-4-CF$_3$ | C$_6$H$_4$-2-CF$_3$ | O | 4-CH$_2$ | 0 | | |
| 1.784 | C$_6$H$_4$-4-CF$_3$ | C$_6$H$_4$-2-CF$_3$ | O | 3-CH$_2$ | 0 | | |
| 1.785 | C$_6$H$_4$-4-CF$_3$ | C$_6$H$_4$-2-CF$_3$ | O | 2-CH$_2$ | 0 | | |
| 1.786 | C$_6$H$_4$-4-CF$_3$ | C$_6$H$_4$-2-CF$_3$ | O | 4-OCH$_2$ | 0 | | |
| 1.787 | C$_6$H$_4$-4-CF$_3$ | C$_6$H$_4$-2-CF$_3$ | O | 3-OCH$_2$ | 0 | | |
| 1.788 | C$_6$H$_4$-4-CF$_3$ | C$_6$H$_4$-2-CF$_3$ | O | 2-OCH$_2$ | 0 | | |
| 1.789 | C$_6$H$_4$-4-CF$_3$ | C$_6$H$_4$-2-CF$_3$ | O | 4-S | 0 | | |
| 1.790 | C$_6$H$_4$-4-CF$_3$ | C$_6$H$_4$-2-CF$_3$ | O | 3-S | 0 | | |
| 1.791 | C$_6$H$_4$-4-CF$_3$ | C$_6$H$_4$-2-CF$_3$ | O | 2-S | 0 | | |
| 1.792 | C$_6$H$_4$-4-CF$_3$ | C$_6$H$_4$-2-CF$_3$ | O | 4-S(O) | 0 | | |
| 1.793 | C$_6$H$_4$-4-CF$_3$ | C$_6$H$_4$-2-CF$_3$ | O | 3-S(O) | 0 | | |
| 1.794 | C$_6$H$_4$-4-CF$_3$ | C$_6$H$_4$-2-CF$_3$ | O | 2-S(O) | 0 | | |
| 1.795 | C$_6$H$_4$-4-CF$_3$ | C$_6$H$_4$-2-CF$_3$ | O | 4-C(O) | 0 | | |
| 1.796 | C$_6$H$_3$-4-CF$_3$ | C$_6$H$_4$-2-CF$_3$ | O | 4-C(O) | 1 | Bd 3-Ar$_1$ | |
| 1.797 | C$_6$H$_3$-4-CF$_3$ | C$_6$H$_4$-2-CF$_3$ | O | 4-C(O) | 1 | 3-C(O) | |
| 1.798 | C$_6$H$_3$-4-CF$_3$ | C$_6$H$_4$-2-CF$_3$ | O | 4-C(O) | 1 | 3-S(O$_2$) | |
| 1.799 | C$_6$H$_4$-4-CF$_3$ | C$_6$H$_4$-2-CF$_3$ | O | 3-C(O) | 0 | | |
| 1.800 | C$_6$H$_3$-4-CF$_3$ | C$_6$H$_4$-2-CF$_3$ | O | 3-C(O) | 1 | Bd 4-Ar$_1$ | |
| 1.801 | C$_6$H$_3$-4-CF$_3$ | C$_6$H$_4$-2-CF$_3$ | O | 3-C(O) | 1 | 4-S(O$_2$) | |
| 1.802 | C$_6$H$_4$-4-CF$_3$ | C$_6$H$_4$-2-CF$_3$ | O | 2-C(O) | 0 | | |

TABLE 1-continued

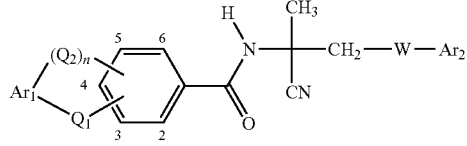

| No. | Ar₁ | Ar₂ | W | Q₁ | n | Q₂ | phys. data |
|---|---|---|---|---|---|---|---|
| 1.803 | C₆H₃-4-CF₃ | C₆H₄-2-CF₃ | O | 2-C(O) | 1 | Bd 3-Ar₁ | |
| 1.804 | C₆H₃-4-CF₃ | C₆H₄-2-CF₃ | O | 2-C(O) | 1 | 3-C(O) | |
| 1.805 | C₆H₃-4-CF₃ | C₆H₄-2-CF₃ | O | 2-C(O) | 1 | 3-S(O₂) | |
| 1.806 | C₆H₄-4-CF₃ | C₆H₄-2-CF₃ | S | 4-CH₂ | 0 | | |
| 1.807 | C₆H₄-4-CF₃ | C₆H₄-2-CF₃ | S | 3-CH₂ | 0 | | |
| 1.808 | C₆H₄-4-CF₃ | C₆H₄-2-CF₃ | S | 2-CH₂ | 0 | | |
| 1.809 | C₆H₄-4-CF₃ | C₆H₄-2-CF₃ | S | 4-OCH₂ | 0 | | |
| 1.810 | C₆H₄-4-CF₃ | C₆H₄-2-CF₃ | S | 3-OCH₂ | 0 | | |
| 1.811 | C₆H₄-4-CF₃ | C₆H₄-2-CF₃ | S | 2-OCH₂ | 0 | | |
| 1.812 | C₆H₄-4-CF₃ | C₆H₄-2-CF₃ | S | 4-S | 0 | | |
| 1.813 | C₆H₄-4-CF₃ | C₆H₄-2-CF₃ | S | 3-S | 0 | | |
| 1.814 | C₆H₄-4-CF₃ | C₆H₄-2-CF₃ | S | 2-S | 0 | | |
| 1.815 | C₆H₄-4-CF₃ | C₆H₄-2-CF₃ | S | 4-S(O) | 0 | | |
| 1.816 | C₆H₄-4-CF₃ | C₆H₄-2-CF₃ | S | 3-S(O) | 0 | | |
| 1.817 | C₆H₄-4-CF₃ | C₆H₄-2-CF₃ | S | 2-S(O) | 0 | | |
| 1.818 | C₆H₄-4-CF₃ | C₆H₄-2-CF₃ | S | 4-C(O) | 0 | | |
| 1.819 | C₆H₃-4-CF₃ | C₆H₄-2-CF₃ | S | 4-C(O) | 1 | Bd 3-Ar₁ | |
| 1.820 | C₆H₃-4-CF₃ | C₆H₄-2-CF₃ | S | 4-C(O) | 1 | 3-C(O) | |
| 1.821 | C₆H₃-4-CF₃ | C₆H₄-2-CF₃ | S | 4-C(O) | 1 | 3-S(O₂) | |
| 1.822 | C₆H₄-4-CF₃ | C₆H₄-2-CF₃ | S | 3-C(O) | 0 | | |
| 1.823 | C₆H₃-4-CF₃ | C₆H₄-2-CF₃ | S | 3-C(O) | 1 | Bd 4-Ar₁ | |
| 1.824 | C₆H₃-4-CF₃ | C₆H₄-2-CF₃ | S | 3-C(O) | 1 | 4-S(O₂) | |
| 1.825 | C₆H₄-4-CF₃ | C₆H₄-2-CF₃ | S | 2-C(O) | 0 | | |
| 1.826 | C₆H₃-4-CF₃ | C₆H₄-2-CF₃ | S | 2-C(O) | 1 | Bd 3-Ar₁ | |
| 1.827 | C₆H₃-4-CF₃ | C₆H₄-2-CF₃ | S | 2-C(O) | 1 | 3-C(O) | |
| 1.828 | C₆H₃-4-CF₃ | C₆H₄-2-CF₃ | S | 2-C(O) | 1 | 3-S(O₂) | |
| 1.829 | C₆H₄-4-OCF₃ | C₆H₅ | O | 4-CH₂ | 0 | | |
| 1.830 | C₆H₄-4-OCF₃ | C₆H₅ | O | 3-CH₂ | 0 | | |
| 1.831 | C₆H₄-4-OCF₃ | C₆H₅ | O | 2-CH₂ | 0 | | |
| 1.832 | C₆H₄-4-OCF₃ | C₆H₅ | O | 4-OCH₂ | 0 | | |
| 1.833 | C₆H₄-4-OCF₃ | C₆H₅ | O | 3-OCH₂ | 0 | | |
| 1.834 | C₆H₄-4-OCF₃ | C₆H₅ | O | 2-OCH₂ | 0 | | |
| 1.835 | C₆H₄-4-OCF₃ | C₆H₅ | O | 4-S | 0 | | |
| 1.836 | C₆H₄-4-OCF₃ | C₆H₅ | O | 3-S | 0 | | |
| 1.837 | C₆H₄-4-OCF₃ | C₆H₅ | O | 2-S | 0 | | |
| 1.838 | C₆H₄-4-OCF₃ | C₆H₅ | O | 4-S(O) | 0 | | |
| 1.839 | C₆H₄-4-OCF₃ | C₆H₅ | O | 3-S(O) | 0 | | |
| 1.840 | C₆H₄-4-OCF₃ | C₆H₅ | O | 2-S(O) | 0 | | |
| 1.841 | C₆H₄-4-OCF₃ | C₆H₅ | O | 4-C(O) | 0 | | |
| 1.842 | C₆H₃-4-OCF₃ | C₆H₅ | O | 4-C(O) | 1 | Bd 3-Ar₁ | |
| 1.843 | C₆H₃-4-OCF₃ | C₆H₅ | O | 4-C(O) | 1 | 3-C(O) | |
| 1.844 | C₆H₃-4-OCF₃ | C₆H₅ | O | 4-C(O) | 1 | 3-S(O₂) | |
| 1.845 | C₆H₄-4-OCF₃ | C₆H₅ | O | 3-C(O) | 0 | | |
| 1.846 | C₆H₃-4-OCF₃ | C₆H₅ | O | 3-C(O) | 1 | Bd 4-Ar₁ | |
| 1.847 | C₆H₃-4-OCF₃ | C₆H₅ | O | 3-C(O) | 1 | 4-S(O₂) | |
| 1.848 | C₆H₄-4-OCF₃ | C₆H₅ | O | 2-C(O) | 0 | | |
| 1.849 | C₆H₃-4-OCF₃ | C₆H₅ | O | 2-C(O) | 1 | Bd 3-Ar₁ | |
| 1.850 | C₆H₃-4-OCF₃ | C₆H₅ | O | 2-C(O) | 1 | 3-C(O) | |
| 1.851 | C₆H₃-4-OCF₃ | C₆H₅ | O | 2-C(O) | 1 | 3-S(O₂) | |
| 1.852 | C₆H₄-4-OCF₃ | C₆H₅ | S | 4-CH₂ | 0 | | |
| 1.853 | C₆H₄-4-OCF₃ | C₆H₅ | S | 3-CH₂ | 0 | | |
| 1.854 | C₆H₄-4-OCF₃ | C₆H₅ | S | 2-CH₂ | 0 | | |
| 1.855 | C₆H₄-4-OCF₃ | C₆H₅ | S | 4-OCH₂ | 0 | | |
| 1.856 | C₆H₄-4-OCF₃ | C₆H₅ | S | 3-OCH₂ | 0 | | |
| 1.857 | C₆H₄-4-OCF₃ | C₆H₅ | S | 2-OCH₂ | 0 | | |
| 1.858 | C₆H₄-4-OCF₃ | C₆H₅ | S | 4-S | 0 | | |
| 1.859 | C₆H₄-4-OCF₃ | C₆H₅ | S | 3-S | 0 | | |
| 1.860 | C₆H₄-4-OCF₃ | C₆H₅ | S | 2-S | 0 | | |
| 1.861 | C₆H₄-4-OCF₃ | C₆H₅ | S | 4-S(O) | 0 | | |
| 1.862 | C₆H₄-4-OCF₃ | C₆H₅ | S | 3-S(O) | 0 | | |
| 1.863 | C₆H₄-4-OCF₃ | C₆H₅ | S | 2-S(O) | 0 | | |
| 1.864 | C₆H₄-4-OCF₃ | C₆H₅ | S | 4-C(O) | 0 | | |
| 1.865 | C₆H₃-4-OCF₃ | C₆H₅ | S | 4-C(O) | 1 | Bd 3-Ar₁ | |
| 1.866 | C₆H₃-4-OCF₃ | C₆H₅ | S | 4-C(O) | 1 | 3-C(O) | |
| 1.867 | C₆H₃-4-OCF₃ | C₆H₅ | S | 4-C(O) | 1 | 3-S(O₂) | |
| 1.868 | C₆H₄-4-OCF₃ | C₆H₅ | S | 3-C(O) | 0 | | |
| 1.869 | C₆H₃-4-OCF₃ | C₆H₅ | S | 3-C(O) | 1 | Bd 4-Ar₁ | |
| 1.870 | C₆H₃-4-OCF₃ | C₆H₅ | S | 3-C(O) | 1 | 4-S(O₂) | |

TABLE 1-continued

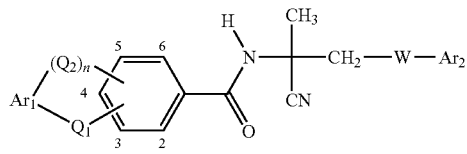

| No. | Ar$_1$ | Ar$_2$ | W | Q$_1$ | n | Q$_2$ | phys. data |
|---|---|---|---|---|---|---|---|
| 1.871 | C$_6$H$_4$-4-OCF$_3$ | C$_6$H$_5$ | S | 2-C(O) | 0 | | |
| 1.872 | C$_6$H$_3$-4-OCF$_3$ | C$_6$H$_5$ | S | 2-C(O) | 1 | Bd 3-Ar$_1$ | |
| 1.873 | C$_6$H$_3$-4-OCF$_3$ | C$_6$H$_5$ | S | 2-C(O) | 1 | 3-C(O) | |
| 1.874 | C$_6$H$_3$-4-OCF$_3$ | C$_6$H$_5$ | S | 2-C(O) | 1 | 3-S(O$_2$) | |
| 1.875 | C$_6$H$_4$-4-OCF$_3$ | C$_6$H$_4$-2-Cl | O | 4-CH$_2$ | 0 | | |
| 1.876 | C$_6$H$_4$-4-OCF$_3$ | C$_6$H$_4$-2-Cl | O | 3-CH$_2$ | 0 | | |
| 1.877 | C$_6$H$_4$-4-OCF$_3$ | C$_6$H$_4$-2-Cl | O | 2-CH$_2$ | 0 | | |
| 1.878 | C$_6$H$_4$-4-OCF$_3$ | C$_6$H$_4$-2-Cl | O | 4-OCH$_2$ | 0 | | |
| 1.879 | C$_6$H$_4$-4-OCF$_3$ | C$_6$H$_4$-2-Cl | O | 3-OCH$_2$ | 0 | | |
| 1.880 | C$_6$H$_4$-4-OCF$_3$ | C$_6$H$_4$-2-Cl | O | 2-OCH$_2$ | 0 | | |
| 1.881 | C$_6$H$_4$-4-OCF$_3$ | C$_6$H$_4$-2-Cl | O | 4-S | 0 | | |
| 1.882 | C$_6$H$_4$-4-OCF$_3$ | C$_6$H$_4$-2-Cl | O | 3-S | 0 | | |
| 1.883 | C$_6$H$_4$-4-OCF$_3$ | C$_6$H$_4$-2-Cl | O | 2-S | 0 | | |
| 1.884 | C$_6$H$_4$-4-OCF$_3$ | C$_6$H$_4$-2-Cl | O | 4-S(O) | 0 | | |
| 1.885 | C$_6$H$_4$-4-OCF$_3$ | C$_6$H$_4$-2-Cl | O | 3-S(O) | 0 | | |
| 1.886 | C$_6$H$_4$-4-OCF$_3$ | C$_6$H$_4$-2-Cl | O | 2-S(O) | 0 | | |
| 1.887 | C$_6$H$_4$-4-OCF$_3$ | C$_6$H$_4$-2-Cl | O | 4-C(O) | 0 | | |
| 1.888 | C$_6$H$_3$-4-OCF$_3$ | C$_6$H$_4$-2-Cl | O | 4-C(O) | 1 | Bd 3-Ar$_1$ | |
| 1.889 | C$_6$H$_3$-4-OCF$_3$ | C$_6$H$_4$-2-Cl | O | 4-C(O) | 1 | 3-C(O) | |
| 1.890 | C$_6$H$_3$-4-OCF$_3$ | C$_6$H$_4$-2-Cl | O | 4-C(O) | 1 | 3-S(O$_2$) | |
| 1.891 | C$_6$H$_4$-4-OCF$_3$ | C$_6$H$_4$-2-Cl | O | 3-C(O) | 0 | | |
| 1.892 | C$_6$H$_3$-4-OCF$_3$ | C$_6$H$_4$-2-Cl | O | 3-C(O) | 1 | Bd 4-Ar$_1$ | |
| 1.893 | C$_6$H$_3$-4-OCF$_3$ | C$_6$H$_4$-2-Cl | O | 3-C(O) | 1 | 4-S(O$_2$) | |
| 1.894 | C$_6$H$_4$-4-OCF$_3$ | C$_6$H$_4$-2-Cl | O | 2-C(O) | 0 | | |
| 1.895 | C$_6$H$_3$-4-OCF$_3$ | C$_6$H$_4$-2-Cl | O | 2-C(O) | 1 | Bd 3-Ar$_1$ | |
| 1.896 | C$_6$H$_3$-4-OCF$_3$ | C$_6$H$_4$-2-Cl | O | 2-C(O) | 1 | 3-C(O) | |
| 1.897 | C$_6$H$_3$-4-OCF$_3$ | C$_6$H$_4$-2-Cl | O | 2-C(O) | 1 | 3-S(O$_2$) | |
| 1.898 | C$_6$H$_4$-4-OCF$_3$ | C$_6$H$_4$-2-Cl | S | 4-CH$_2$ | 0 | | |
| 1.899 | C$_6$H$_4$-4-OCF$_3$ | C$_6$H$_4$-2-Cl | S | 3-CH$_2$ | 0 | | |
| 1.900 | C$_6$H$_4$-4-OCF$_3$ | C$_6$H$_4$-2-Cl | S | 2-CH$_2$ | 0 | | |
| 1.901 | C$_6$H$_4$-4-OCF$_3$ | C$_6$H$_4$-2-Cl | S | 4-OCH$_2$ | 0 | | |
| 1.902 | C$_6$H$_4$-4-OCF$_3$ | C$_6$H$_4$-2-Cl | S | 3-OCH$_2$ | 0 | | |
| 1.903 | C$_6$H$_4$-4-OCF$_3$ | C$_6$H$_4$-2-Cl | S | 2-OCH$_2$ | 0 | | |
| 1.904 | C$_6$H$_4$-4-OCF$_3$ | C$_6$H$_4$-2-Cl | S | 4-S | 0 | | |
| 1.905 | C$_6$H$_4$-4-OCF$_3$ | C$_6$H$_4$-2-Cl | S | 3-S | 0 | | |
| 1.906 | C$_6$H$_4$-4-OCF$_3$ | C$_6$H$_4$-2-Cl | S | 2-S | 0 | | |
| 1.907 | C$_6$H$_4$-4-OCF$_3$ | C$_6$H$_4$-2-Cl | S | 4-S(O) | 0 | | |
| 1.908 | C$_6$H$_4$-4-OCF$_3$ | C$_6$H$_4$-2-Cl | S | 3-S(O) | 0 | | |
| 1.909 | C$_6$H$_4$-4-OCF$_3$ | C$_6$H$_4$-2-Cl | S | 2-S(O) | 0 | | |
| 1.910 | C$_6$H$_4$-4-OCF$_3$ | C$_6$H$_4$-2-Cl | S | 4-C(O) | 0 | | |
| 1.911 | C$_6$H$_3$-4-OCF$_3$ | C$_6$H$_4$-2-Cl | S | 4-C(O) | 1 | Bd 3-Ar$_1$ | |
| 1.912 | C$_6$H$_3$-4-OCF$_3$ | C$_6$H$_4$-2-Cl | S | 4-C(O) | 1 | 3-C(O) | |
| 1.913 | C$_6$H$_3$-4-OCF$_3$ | C$_6$H$_4$-2-Cl | S | 4-C(O) | 1 | 3-S(O$_2$) | |
| 1.914 | C$_6$H$_4$-4-OCF$_3$ | C$_6$H$_4$-2-Cl | S | 3-C(O) | 0 | | |
| 1.915 | C$_6$H$_3$-4-OCF$_3$ | C$_6$H$_4$-2-Cl | S | 3-C(O) | 1 | Bd 4-Ar$_1$ | |
| 1.916 | C$_6$H$_3$-4-OCF$_3$ | C$_6$H$_4$-2-Cl | S | 3-C(O) | 1 | 4-S(O$_2$) | |
| 1.917 | C$_6$H$_4$-4-OCF$_3$ | C$_6$H$_4$-2-Cl | S | 2-C(O) | 0 | | |
| 1.918 | C$_6$H$_3$-4-OCF$_3$ | C$_6$H$_4$-2-Cl | S | 2-C(O) | 1 | Bd 3-Ar$_1$ | |
| 1.919 | C$_6$H$_3$-4-OCF$_3$ | C$_6$H$_4$-2-Cl | S | 2-C(O) | 1 | 3-C(O) | |
| 1.920 | C$_6$H$_3$-4-OCF$_3$ | C$_6$H$_4$-2-Cl | S | 2-C(O) | 1 | 3-S(O$_2$) | |
| 1.921 | C$_6$H$_4$-4-OCF$_3$ | C$_6$H$_4$-2-CF$_3$ | O | 4-CH$_2$ | 0 | | |
| 1.922 | C$_6$H$_4$-4-OCF$_3$ | C$_6$H$_4$-2-CF$_3$ | O | 3-CH$_2$ | 0 | | |
| 1.923 | C$_6$H$_4$-4-OCF$_3$ | C$_6$H$_4$-2-CF$_3$ | O | 2-CH$_2$ | 0 | | |
| 1.924 | C$_6$H$_4$-4-OCF$_3$ | C$_6$H$_4$-2-CF$_3$ | O | 4-OCH$_2$ | 0 | | |
| 1.925 | C$_6$H$_4$-4-OCF$_3$ | C$_6$H$_4$-2-CF$_3$ | O | 3-OCH$_2$ | 0 | | |
| 1.926 | C$_6$H$_4$-4-OCF$_3$ | C$_6$H$_4$-2-CF$_3$ | O | 2-OCH$_2$ | 0 | | |
| 1.927 | C$_6$H$_4$-4-OCF$_3$ | C$_6$H$_4$-2-CF$_3$ | O | 4-S | 0 | | |
| 1.928 | C$_6$H$_4$-4-OCF$_3$ | C$_6$H$_4$-2-CF$_3$ | O | 3-S | 0 | | |
| 1.929 | C$_6$H$_4$-4-OCF$_3$ | C$_6$H$_4$-2-CF$_3$ | O | 2-S | 0 | | |
| 1.930 | C$_6$H$_4$-4-OCF$_3$ | C$_6$H$_4$-2-CF$_3$ | O | 4-S(O) | 0 | | |
| 1.931 | C$_6$H$_4$-4-OCF$_3$ | C$_6$H$_4$-2-CF$_3$ | O | 3-S(O) | 0 | | |
| 1.932 | C$_6$H$_4$-4-OCF$_3$ | C$_6$H$_4$-2-CF$_3$ | O | 2-S(O) | 0 | | |
| 1.933 | C$_6$H$_4$-4-OCF$_3$ | C$_6$H$_4$-2-CF$_3$ | O | 4-C(O) | 0 | | |
| 1.934 | C$_6$H$_3$-4-OCF$_3$ | C$_6$H$_4$-2-CF$_3$ | O | 4-C(O) | 1 | Bd 3-Ar$_1$ | |
| 1.935 | C$_6$H$_3$-4-OCF$_3$ | C$_6$H$_4$-2-CF$_3$ | O | 4-C(O) | 1 | 3-C(O) | |
| 1.936 | C$_6$H$_3$-4-OCF$_3$ | C$_6$H$_4$-2-CF$_3$ | O | 4-C(O) | 1 | 3-S(O$_2$) | |
| 1.937 | C$_6$H$_4$-4-OCF$_3$ | C$_6$H$_4$-2-CF$_3$ | O | 3-C(O) | 0 | | |
| 1.938 | C$_6$H$_3$-4-OCF$_3$ | C$_6$H$_4$-2-CF$_3$ | O | 3-C(O) | 1 | Bd 4-Ar$_1$ | |

TABLE 1-continued

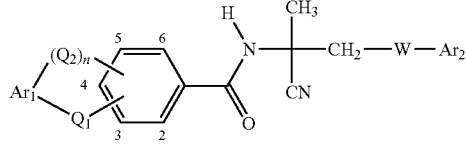

| No. | Ar$_1$ | Ar$_2$ | W | Q$_1$ | n | Q$_2$ | phys. data |
|---|---|---|---|---|---|---|---|
| 1.939 | C$_6$H$_3$-4-OCF$_3$ | C$_6$H$_4$-2-CF$_3$ | O | 3-C(O) | 1 | 4-S(O$_2$) | |
| 1.940 | C$_6$H$_4$-4-OCF$_3$ | C$_6$H$_4$-2-CF$_3$ | O | 2-C(O) | 0 | | |
| 1.941 | C$_6$H$_3$-4-OCF$_3$ | C$_6$H$_4$-2-CF$_3$ | O | 2-C(O) | 1 | Bd 3-Ar$_1$ | |
| 1.942 | C$_6$H$_3$-4-OCF$_3$ | C$_6$H$_4$-2-CF$_3$ | O | 2-C(O) | 1 | 3-C(O) | |
| 1.943 | C$_6$H$_3$-4-OCF$_3$ | C$_6$H$_4$-2-CF$_3$ | O | 2-C(O) | 1 | 3-S(O$_2$) | |
| 1.944 | C$_6$H$_4$-4-OCF$_3$ | C$_6$H$_4$-2-CF$_3$ | S | 4-CH$_2$ | 0 | | |
| 1.945 | C$_6$H$_4$-4-OCF$_3$ | C$_6$H$_4$-2-CF$_3$ | S | 3-CH$_2$ | 0 | | |
| 1.946 | C$_6$H$_4$-4-OCF$_3$ | C$_6$H$_4$-2-CF$_3$ | S | 2-CH$_2$ | 0 | | |
| 1.947 | C$_6$H$_4$-4-OCF$_3$ | C$_6$H$_4$-2-CF$_3$ | S | 4-OCH$_2$ | 0 | | |
| 1.948 | C$_6$H$_4$-4-OCF$_3$ | C$_6$H$_4$-2-CF$_3$ | S | 3-OCH$_2$ | 0 | | |
| 1.949 | C$_6$H$_4$-4-OCF$_3$ | C$_6$H$_4$-2-CF$_3$ | S | 2-OCH$_2$ | 0 | | |
| 1.950 | C$_6$H$_4$-4-OCF$_3$ | C$_6$H$_4$-2-CF$_3$ | S | 4-S | 0 | | |
| 1.951 | C$_6$H$_4$-4-OCF$_3$ | C$_6$H$_4$-2-CF$_3$ | S | 3-S | 0 | | |
| 1.952 | C$_6$H$_4$-4-OCF$_3$ | C$_6$H$_4$-2-CF$_3$ | S | 2-S | 0 | | |
| 1.953 | C$_6$H$_4$-4-OCF$_3$ | C$_6$H$_4$-2-CF$_3$ | S | 4-S(O) | 0 | | |
| 1.954 | C$_6$H$_4$-4-OCF$_3$ | C$_6$H$_4$-2-CF$_3$ | S | 3-S(O) | 0 | | |
| 1.955 | C$_6$H$_4$-4-OCF$_3$ | C$_6$H$_4$-2-CF$_3$ | S | 2-S(O) | 0 | | |
| 1.956 | C$_6$H$_4$-4-OCF$_3$ | C$_6$H$_4$-2-CF$_3$ | S | 4-C(O) | 0 | | |
| 1.957 | C$_6$H$_3$-4-OCF$_3$ | C$_6$H$_4$-2-CF$_3$ | S | 4-C(O) | 1 | Bd 3-Ar$_1$ | |
| 1.958 | C$_6$H$_3$-4-OCF$_3$ | C$_6$H$_4$-2-CF$_3$ | S | 4-C(O) | 1 | 3-C(O) | |
| 1.959 | C$_6$H$_3$-4-OCF$_3$ | C$_6$H$_4$-2-CF$_3$ | S | 4-C(O) | 1 | 3-S(O$_2$) | |
| 1.960 | C$_6$H$_4$-4-OCF$_3$ | C$_6$H$_4$-2-CF$_3$ | S | 3-C(O) | 0 | | |
| 1.961 | C$_6$H$_3$-4-OCF$_3$ | C$_6$H$_4$-2-CF$_3$ | S | 3-C(O) | 1 | Bd 4-Ar$_1$ | |
| 1.962 | C$_6$H$_3$-4-OCF$_3$ | C$_6$H$_4$-2-CF$_3$ | S | 3-C(O) | 1 | 4-S(O$_2$) | |
| 1.963 | C$_6$H$_4$-4-OCF$_3$ | C$_6$H$_4$-2-CF$_3$ | S | 2-C(O) | 0 | | |
| 1.964 | C$_6$H$_3$-4-OCF$_3$ | C$_6$H$_4$-2-CF$_3$ | S | 2-C(O) | 1 | Bd 3-Ar$_1$ | |
| 1.965 | C$_6$H$_3$-4-OCF$_3$ | C$_6$H$_4$-2-CF$_3$ | S | 2-C(O) | 1 | 3-C(O) | |
| 1.966 | C$_6$H$_3$-4-OCF$_3$ | C$_6$H$_4$-2-CF$_3$ | S | 2-C(O) | 1 | 3-S(O$_2$) | |
| 1.967 | C$_6$H$_4$-4-t-C$_4$H$_9$ | C$_6$H$_5$ | O | 4-CH$_2$ | 0 | | |
| 1.968 | C$_6$H$_4$-4-t-C$_4$H$_9$ | C$_6$H$_5$ | O | 3-CH$_2$ | 0 | | |
| 1.969 | C$_6$H$_4$-4-t-C$_4$H$_9$ | C$_6$H$_5$ | O | 2-CH$_2$ | 0 | | |
| 1.970 | C$_6$H$_4$-4-t-C$_4$H$_9$ | C$_6$H$_5$ | O | 4-OCH$_2$ | 0 | | |
| 1.971 | C$_6$H$_4$-4-t-C$_4$H$_9$ | C$_6$H$_5$ | O | 3-OCH$_2$ | 0 | | |
| 1.972 | C$_6$H$_4$-4-t-C$_4$H$_9$ | C$_6$H$_5$ | O | 2-OCH$_2$ | 0 | | |
| 1.973 | C$_6$H$_4$-4-t-C$_4$H$_9$ | C$_6$H$_5$ | O | 4-S | 0 | | |
| 1.974 | C$_6$H$_4$-4-t-C$_4$H$_9$ | C$_6$H$_5$ | O | 3-S | 0 | | |
| 1.975 | C$_6$H$_4$-4-t-C$_4$H$_9$ | C$_6$H$_5$ | O | 2-S | 0 | | |
| 1.976 | C$_6$H$_4$-4-t-C$_4$H$_9$ | C$_6$H$_5$ | O | 4-S(O) | 0 | | |
| 1.977 | C$_6$H$_4$-4-t-C$_4$H$_9$ | C$_6$H$_5$ | O | 3-S(O) | 0 | | |
| 1.978 | C$_6$H$_4$-4-t-C$_4$H$_9$ | C$_6$H$_5$ | O | 2-S(O) | 0 | | |
| 1.979 | C$_6$H$_4$-4-t-C$_4$H$_9$ | C$_6$H$_5$ | O | 4-C(O) | 0 | | |
| 1.980 | C$_6$H$_3$-4-t-C$_4$H$_9$ | C$_6$H$_5$ | O | 4-C(O) | 1 | Bd 3-Ar$_1$ | |
| 1.981 | C$_6$H$_3$-4-t-C$_4$H$_9$ | C$_6$H$_5$ | O | 4-C(O) | 1 | 3-C(O) | |
| 1.982 | C$_6$H$_3$-4-t-C$_4$H$_9$ | C$_6$H$_5$ | O | 4-C(O) | 1 | 3-S(O$_2$) | |
| 1.983 | C$_6$H$_4$-4-t-C$_4$H$_9$ | C$_6$H$_5$ | O | 3-C(O) | 0 | | |
| 1.984 | C$_6$H$_3$-4-t-C$_4$H$_9$ | C$_6$H$_5$ | O | 3-C(O) | 1 | Bd 4-Ar$_1$ | |
| 1.985 | C$_6$H$_3$-4-t-C$_4$H$_9$ | C$_6$H$_5$ | O | 3-C(O) | 1 | 4-S(O$_2$) | |
| 1.986 | C$_6$H$_4$-4-t-C$_4$H$_9$ | C$_6$H$_5$ | O | 2-C(O) | 0 | | |
| 1.987 | C$_6$H$_3$-4-t-C$_4$H$_9$ | C$_6$H$_5$ | O | 2-C(O) | 1 | Bd 3-Ar$_1$ | |
| 1.988 | C$_6$H$_3$-4-t-C$_4$H$_9$ | C$_6$H$_5$ | O | 2-C(O) | 1 | 3-C(O) | |
| 1.989 | C$_6$H$_3$-4-t-C$_4$H$_9$ | C$_6$H$_5$ | O | 2-C(O) | 1 | 3-S(O$_2$) | |
| 1.990 | C$_6$H$_4$-4-t-C$_4$H$_9$ | C$_6$H$_5$ | S | 4-CH$_2$ | 0 | | |
| 1.991 | C$_6$H$_4$-4-t-C$_4$H$_9$ | C$_6$H$_5$ | S | 3-CH$_2$ | 0 | | |
| 1.992 | C$_6$H$_4$-4-t-C$_4$H$_9$ | C$_6$H$_5$ | S | 2-CH$_2$ | 0 | | |
| 1.993 | C$_6$H$_4$-4-t-C$_4$H$_9$ | C$_6$H$_5$ | S | 4-OCH$_2$ | 0 | | |
| 1.994 | C$_6$H$_4$-4-t-C$_4$H$_9$ | C$_6$H$_5$ | S | 3-OCH$_2$ | 0 | | |
| 1.995 | C$_6$H$_4$-4-t-C$_4$H$_9$ | C$_6$H$_5$ | S | 2-OCH$_2$ | 0 | | |
| 1.996 | C$_6$H$_4$-4-t-C$_4$H$_9$ | C$_6$H$_5$ | S | 4-S | 0 | | |
| 1.997 | C$_6$H$_4$-4-t-C$_4$H$_9$ | C$_6$H$_5$ | S | 3-S | 0 | | |
| 1.998 | C$_6$H$_4$-4-t-C$_4$H$_9$ | C$_6$H$_5$ | S | 2-S | 0 | | |
| 1.999 | C$_6$H$_4$-4-t-C$_4$H$_9$ | C$_6$H$_5$ | S | 4-S(O) | 0 | | |
| 1.1000 | C$_6$H$_4$-4-t-C$_4$H$_9$ | C$_6$H$_5$ | S | 3-S(O) | 0 | | |
| 1.1001 | C$_6$H$_4$-4-t-C$_4$H$_9$ | C$_6$H$_5$ | S | 2-S(O) | 0 | | |
| 1.1002 | C$_6$H$_4$-4-t-C$_4$H$_9$ | C$_6$H$_5$ | S | 4-C(O) | 0 | | |
| 1.1003 | C$_6$H$_3$-4-t-C$_4$H$_9$ | C$_6$H$_5$ | S | 4-C(O) | 1 | Bd 3-Ar$_1$ | |
| 1.1004 | C$_6$H$_3$-4-t-C$_4$H$_9$ | C$_6$H$_5$ | S | 4-C(O) | 1 | 3-C(O) | |
| 1.1005 | C$_6$H$_3$-4-t-C$_4$H$_9$ | C$_6$H$_5$ | S | 4-C(O) | 1 | 3-S(O$_2$) | |
| 1.1006 | C$_6$H$_4$-4-t-C$_4$H$_9$ | C$_6$H$_5$ | S | 3-C(O) | 0 | | |

TABLE 1-continued

[Structure: Ar₁—Q₁—(Q₂)ₙ—C₆H₃(positions 2,3,4,5,6)—C(O)—N(H)—C(CH₃)(CN)—CH₂—W—Ar₂]

| No. | Ar₁ | Ar₂ | W | Q₁ | n | Q₂ | phys. data |
|---|---|---|---|---|---|---|---|
| 1.1007 | C₆H₃-4-t-C₄H₉ | C₆H₅ | S | 3-C(O) | 1 | Bd 4-Ar₁ | |
| 1.1008 | C₆H₃-4-t-C₄H₉ | C₆H₅ | S | 3-C(O) | 1 | 4-S(O₂) | |
| 1.1009 | C₆H₄-4-t-C₄H₉ | C₆H₅ | S | 2-C(O) | 0 | | |
| 1.1010 | C₆H₃-4-t-C₄H₉ | C₆H₅ | S | 2-C(O) | 1 | Bd 3-Ar₁ | |
| 1.1011 | C₆H₃-4-t-C₄H₉ | C₆H₅ | S | 2-C(O) | 1 | 3-C(O) | |
| 1.1012 | C₆H₃-4-t-C₄H₉ | C₆H₅ | S | 2-C(O) | 1 | 3-S(O₂) | |
| 1.1013 | C₆H₄-4-t-C₄H₉ | C₆H₄-2-Cl | O | 4-CH₂ | 0 | | |
| 1.1014 | C₆H₄-4-t-C₄H₉ | C₆H₄-2-Cl | O | 3-CH₂ | 0 | | |
| 1.1015 | C₆H₄-4-t-C₄H₉ | C₆H₄-2-Cl | O | 2-CH₂ | 0 | | |
| 1.1016 | C₆H₄-4-t-C₄H₉ | C₆H₄-2-Cl | O | 4-OCH₂ | 0 | | |
| 1.1017 | C₆H₄-4-t-C₄H₉ | C₆H₄-2-Cl | O | 3-OCH₂ | 0 | | |
| 1.1018 | C₆H₄-4-t-C₄H₉ | C₆H₄-2-Cl | O | 2-OCH₂ | 0 | | |
| 1.1019 | C₆H₄-4-t-C₄H₉ | C₆H₄-2-Cl | O | 4-S | 0 | | |
| 1.1020 | C₆H₄-4-t-C₄H₉ | C₆H₄-2-Cl | O | 3-S | 0 | | |
| 1.1021 | C₆H₄-4-t-C₄H₉ | C₆H₄-2-Cl | O | 2-S | 0 | | |
| 1.1022 | C₆H₄-4-t-C₄H₉ | C₆H₄-2-Cl | O | 4-S(O) | 0 | | |
| 1.1023 | C₆H₄-4-t-C₄H₉ | C₆H₄-2-Cl | O | 3-S(O) | 0 | | |
| 1.1024 | C₆H₄-4-t-C₄H₉ | C₆H₄-2-Cl | O | 2-S(O) | 0 | | |
| 1.1025 | C₆H₄-4-t-C₄H₉ | C₆H₄-2-Cl | O | 4-C(O) | 0 | | |
| 1.1026 | C₆H₃-4-t-C₄H₉ | C₆H₄-2-Cl | O | 4-C(O) | 1 | Bd 3-Ar₁ | |
| 1.1027 | C₆H₃-4-t-C₄H₉ | C₆H₄-2-Cl | O | 4-C(O) | 1 | 3-C(O) | |
| 1.1028 | C₆H₃-4-t-C₄H₉ | C₆H₄-2-Cl | O | 4-C(O) | 1 | 3-S(O₂) | |
| 1.1029 | C₆H₄-4-t-C₄H₉ | C₆H₄-2-Cl | O | 3-C(O) | 0 | | |
| 1.1030 | C₆H₃-4-t-C₄H₉ | C₆H₄-2-Cl | O | 3-C(O) | 1 | Bd 4-Ar₁ | |
| 1.1031 | C₆H₃-4-t-C₄H₉ | C₆H₄-2-Cl | O | 3-C(O) | 1 | 4-S(O₂) | |
| 1.1032 | C₆H₄-4-t-C₄H₉ | C₆H₄-2-Cl | O | 2-C(O) | 0 | | |
| 1.1033 | C₆H₃-4-t-C₄H₉ | C₆H₄-2-Cl | O | 2-C(O) | 1 | Bd 3-Ar₁ | |
| 1.1034 | C₆H₃-4-t-C₄H₉ | C₆H₄-2-Cl | O | 2-C(O) | 1 | 3-C(O) | |
| 1.1035 | C₆H₃-4-t-C₄H₉ | C₆H₄-2-Cl | O | 2-C(O) | 1 | 3-S(O₂) | |
| 1.1036 | C₆H₄-4-t-C₄H₉ | C₆H₄-2-Cl | S | 4-CH₂ | 0 | | |
| 1.1037 | C₆H₄-4-t-C₄H₉ | C₆H₄-2-Cl | S | 3-CH₂ | 0 | | |
| 1.1038 | C₆H₄-4-t-C₄H₉ | C₆H₄-2-Cl | S | 2-CH₂ | 0 | | |
| 1.1039 | C₆H₄-4-t-C₄H₉ | C₆H₄-2-Cl | S | 4-OCH₂ | 0 | | |
| 1.1040 | C₆H₄-4-t-C₄H₉ | C₆H₄-2-Cl | S | 3-OCH₂ | 0 | | |
| 1.1041 | C₆H₄-4-t-C₄H₉ | C₆H₄-2-Cl | S | 2-OCH₂ | 0 | | |
| 1.1042 | C₆H₄-4-t-C₄H₉ | C₆H₄-2-Cl | S | 4-S | 0 | | |
| 1.1043 | C₆H₄-4-t-C₄H₉ | C₆H₄-2-Cl | S | 3-S | 0 | | |
| 1.1044 | C₅H₄-4-t-C₄H₉ | C₆H₄-2-Cl | S | 2-S | 0 | | |
| 1.1045 | C₆H₄-4-t-C₄H₉ | C₆H₄-2-Cl | S | 4-S(O) | 0 | | |
| 1.1046 | C₆H₄-4-t-C₄H₉ | C₆H₄-2-Cl | S | 3-S(O) | 0 | | |
| 1.1047 | C₆H₄-4-t-C₄H₉ | C₆H₄-2-Cl | S | 2-S(O) | 0 | | |
| 1.1048 | C₆H₄-4-t-C₄H₉ | C₆H₄-2-Cl | S | 4-C(O) | 0 | | |
| 1.1049 | C₆H₃-4-t-C₄H₉ | C₆H₄-2-Cl | S | 4-C(O) | 1 | Bd 3-Ar₁ | |
| 1.1050 | C₆H₃-4-t-C₄H₉ | C₆H₄-2-Cl | S | 4-C(O) | 1 | 3-C(O) | |
| 1.1051 | C₆H₃-4-t-C₄H₉ | C₆H₄-2-Cl | S | 4-C(O) | 1 | 3-S(O₂) | |
| 1.1052 | C₆H₄-4-t-C₄H₉ | C₆H₄-2-Cl | S | 3-C(O) | 0 | | |
| 1.1053 | C₆H₃-4-t-C₄H₉ | C₆H₄-2-Cl | S | 3-C(O) | 1 | Bd 4-Ar₁ | |
| 1.1054 | C₆H₃-4-t-C₄H₉ | C₅H₄-2-Cl | S | 3-C(O) | 1 | 4-S(O₂) | |
| 1.1055 | C₆H₄-4-t-C₄H₉ | C₆H₄-2-Cl | S | 2-C(O) | 0 | | |
| 1.1056 | C₆H₃-4-t-C₄H₉ | C₆H₄-2-Cl | S | 2-C(O) | 1 | Bd 3-Ar₁ | |
| 1.1057 | C₅H₃-4-t-C₄H₉ | C₆H₄-2-Cl | S | 2-C(O) | 1 | 3-C(O) | |
| 1.1058 | C₆H₃-4-t-C₄H₉ | C₆H₄-2-Cl | S | 2-C(O) | 1 | 3-S(O₂) | |
| 1.1059 | C₆H₄-4-t-C₄H₉ | C₆H₄-2-CF₃ | O | 4-CH₂ | 0 | | |
| 1.1060 | C₆H₄-4-t-C₄H₉ | C₆H₄-2-CF₃ | O | 3-CH₂ | 0 | | |
| 1.1061 | C₆H₄-4-t-C₄H₉ | C₆H₄-2-CF₃ | O | 2-CH₂ | 0 | | |
| 1.1062 | C₆H₄-4-t-C₄H₉ | C₆H₄-2-CF₃ | O | 4-OCH₂ | 0 | | |
| 1.1063 | C₆H₄-4-t-C₄H₉ | C₆H₄-2-CF₃ | O | 3-OCH₂ | 0 | | |
| 1.1064 | C₆H₄-4-t-C₄H₉ | C₆H₄-2-CF₃ | O | 2-OCH₂ | 0 | | |
| 1.1065 | C₆H₄-4-t-C₄H₉ | C₆H₄-2-CF₃ | O | 4-S | 0 | | |
| 1.1066 | C₆H₄-4-t-C₄H₉ | C₆H₄-2-CF₃ | O | 3-S | 0 | | |
| 1.1067 | C₆H₄-4-t-C₄H₉ | C₆H₄-2-CF₃ | O | 2-S | 0 | | |
| 1.1068 | C₆H₄-4-t-C₄H₉ | C₆H₄-2-CF₃ | O | 4-S(O) | 0 | | |
| 1.1069 | C₆H₄-4-t-C₄H₉ | C₆H₄-2-CF₃ | O | 3-S(O) | 0 | | |
| 1.1070 | C₆H₄-4-t-C₄H₉ | C₆H₄-2-CF₃ | O | 2-S(O) | 0 | | |
| 1.1071 | C₆H₄-4-t-C₄H₉ | C₆H₄-2-CF₃ | O | 4-C(O) | 0 | | |
| 1.1072 | C₆H₃-4-t-C₄H₉ | C₆H₄-2-CF₃ | O | 4-C(O) | 1 | Bd 3-Ar₁ | |
| 1.1073 | C₅H₃-4-t-C₄H₉ | C₆H₄-2-CF₃ | O | 4-C(O) | 1 | 3-C(O) | |
| 1.1074 | C₆H₃-4-t-C₄H₉ | C₆H₄-2-CF₃ | O | 4-C(O) | 1 | 3-S(O₂) | |

TABLE 1-continued

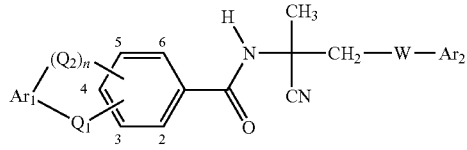

| No. | Ar₁ | Ar₂ | W | Q₁ | n | Q₂ | phys. data |
|---|---|---|---|---|---|---|---|
| 1.1075 | C₆H₄-4-t-C₄H₉ | C₆H₄-2-CF₃ | O | 3-C(O) | 0 | | |
| 1.1076 | C₆H₃-4-t-C₄H₉ | C₆H₄-2-CF₃ | O | 3-C(O) | 1 | Bd 4-Ar₁ | |
| 1.1077 | C₆H₃-4-t-C₄H₉ | C₆H₄-2-CF₃ | O | 3-C(O) | 1 | 4-S(O₂) | |
| 1.1078 | C₆H₄-4-t-C₄H₉ | C₆H₄-2-CF₃ | O | 2-C(O) | 0 | | |
| 1.1079 | C₆H₃-4-t-C₄H₉ | C₆H₄-2-CF₃ | O | 2-C(O) | 1 | Bd 3-Ar₁ | |
| 1.1080 | C₆H₃-4-t-C₄H₉ | C₆H₄-2-CF₃ | O | 2-C(O) | 1 | 3-C(O) | |
| 1.1081 | C₆H₃-4-t-C₄H₉ | C₆H₄-2-CF₃ | O | 2-C(O) | 1 | 3-S(O₂) | |
| 1.1082 | C₆H₄-4-t-C₄H₉ | C₆H₄-2-CF₃ | S | 4-CH₂ | 0 | | |
| 1.1083 | C₆H₄-4-t-C₄H₉ | C₆H₄-2-CF₃ | S | 3-CH₂ | 0 | | |
| 1.1084 | C₆H₄-4-t-C₄H₉ | C₆H₄-2-CF₃ | S | 2-CH₂ | 0 | | |
| 1.1085 | C₆H₄-4-t-C₄H₉ | C₆H₄-2-CF₃ | S | 4-OCH₂ | 0 | | |
| 1.1086 | C₆H₄-4-t-C₄H₉ | C₆H₄-2-CF₃ | S | 3-OCH₂ | 0 | | |
| 1.1087 | C₆H₄-4-t-C₄H₉ | C₆H₄-2-CF₃ | S | 2-OCH₂ | 0 | | |
| 1.1088 | C₆H₄-4-t-C₄H₉ | C₆H₄-2-CF₃ | S | 4-S | 0 | | |
| 1.1089 | C₆H₄-4-t-C₄H₉ | C₆H₄-2-CF₃ | S | 3-S | 0 | | |
| 1.1090 | C₆H₄-4-t-C₄H₉ | C₆H₄-2-CF₃ | S | 2-S | 0 | | |
| 1.1091 | C₆H₄-4-t-C₄H₉ | C₆H₄-2-CF₃ | S | 4-S(O) | 0 | | |
| 1.1092 | C₆H₄-4-t-C₄H₉ | C₆H₄-2-CF₃ | S | 3-S(O) | 0 | | |
| 1.1093 | C₆H₄-4-t-C₄H₉ | C₆H₄-2-CF₃ | S | 2-S(O) | 0 | | |
| 1.1094 | C₆H₄-4-t-C₄H₉ | C₆H₄-2-CF₃ | S | 4-C(O) | 0 | | |
| 1.1095 | C₆H₃-4-t-C₄H₉ | C₆H₄-2-CF₃ | S | 4-C(O) | 1 | Bd 3-Ar₁ | |
| 1.1096 | C₆H₃-4-t-C₄H₉ | C₆H₄-2-CF₃ | S | 4-C(O) | 1 | 3-C(O) | |
| 1.1097 | C₆H₃-4-t-C₄H₉ | C₆H₄-2-CF₃ | S | 4-C(O) | 1 | 3-S(O₂) | |
| 1.1098 | C₆H₄-4-t-C₄H₉ | C₆H₄-2-CF₃ | S | 3-C(O) | 0 | | |
| 1.1099 | C₆H₃-4-t-C₄H₉ | C₆H₄-2-CF₃ | S | 3-C(O) | 1 | Bd 4-Ar₁ | |
| 1.1100 | C₆H₃-4-t-C₄H₉ | C₆H₄-2-CF₃ | S | 3-C(O) | 1 | 4-S(O₂) | |
| 1.1101 | C₆H₄-4-t-C₄H₉ | C₆H₄-2-CF₃ | S | 2-C(O) | 0 | | |
| 1.1102 | C₆H₃-4-t-C₄H₉ | C₆H₄-2-CF₃ | S | 2-C(O) | 1 | Bd 3-Ar₁ | |
| 1.1103 | C₆H₃-4-t-C₄H₉ | C₆H₄-2-CF₃ | S | 2-C(O) | 1 | 3-C(O) | |
| 1.1104 | C₆H₃-4-t-C₄H₉ | C₆H₄-2-CF₃ | S | 2-C(O) | 1 | 3-S(O₂) | |
| 1.1105 | 3-C₅H₄N | C₆H₅ | O | 4-CH₂ | 0 | | |
| 1.1106 | 3-C₅H₄N | C₆H₅ | O | 3-CH₂ | 0 | | |
| 1.1107 | 3-C₅H₄N | C₆H₅ | O | 2-CH₂ | 0 | | |
| 1.1108 | 3-C₅H₄N | C₆H₅ | O | 4-OCH₂ | 0 | | |
| 1.1109 | 3-C₅H₄N | C₆H₅ | O | 3-OCH₂ | 0 | | |
| 1.1110 | 3-C₅H₄N | C₆H₅ | O | 2-OCH₂ | 0 | | |
| 1.1111 | 3-C₅H₄N | C₆H₅ | O | 4-S | 0 | | |
| 1.1112 | 3-C₅H₄N | C₆H₅ | O | 3-S | 0 | | |
| 1.1113 | 3-C₅H₄N | C₆H₅ | O | 2-S | 0 | | |
| 1.1114 | 3-C₅H₄N | C₆H₅ | O | 4-S(O) | 0 | | |
| 1.1115 | 3-C₅H₄N | C₆H₅ | O | 3-S(O) | 0 | | |
| 1.1116 | 3-C₅H₄N | C₆H₅ | O | 2-S(O) | 0 | | |
| 1.1117 | 3-C₅H₄N | C₆H₅ | O | 4-C(O) | 0 | | |
| 1.1118 | 3-C₅H₄N | C₆H₅ | O | 3-C(O) | 0 | | |
| 1.1119 | 3-C₅H₄N | C₆H₅ | O | 2-C(O) | 0 | | |
| 1.1120 | 3-C₅H₄N | C₆H₅ | S | 4-CH₂ | 0 | | |
| 1.1121 | 3-C₅H₄N | C₆H₅ | S | 3-CH₂ | 0 | | |
| 1.1122 | 3-C₅H₄N | C₆H₅ | S | 2-CH₂ | 0 | | |
| 1.1123 | 3-C₅H₄N | C₆H₅ | S | 4-OCH₂ | 0 | | |
| 1.1124 | 3-C₅H₄N | C₆H₅ | S | 3-OCH₂ | 0 | | |
| 1.1125 | 3-C₅H₄N | C₆H₅ | S | 2-OCH₂ | 0 | | |
| 1.1126 | 3-C₅H₄N | C₆H₅ | S | 4-S | 0 | | |
| 1.1127 | 3-C₅H₄N | C₆H₅ | S | 3-S | 0 | | |
| 1.1128 | 3-C₅H₄N | C₆H₅ | S | 2-S | 0 | | |
| 1.1129 | 3-C₅H₄N | C₆H₅ | S | 4-S(O) | 0 | | |
| 1.1130 | 3-C₅H₄N | C₆H₅ | S | 3-S(O) | 0 | | |
| 1.1131 | 3-C₅H₄N | C₆H₅ | S | 2-S(O) | 0 | | |
| 1.1132 | 3-C₅H₄N | C₆H₅ | S | 4-C(O) | 0 | | |
| 1.1133 | 3-C₅H₄N | C₆H₅ | S | 3-C(O) | 0 | | |
| 1.1134 | 3-C₅H₄N | C₆H₅ | S | 2-C(O) | 0 | | |
| 1.1135 | 3-C₅H₄N | C₆H₄-2-Cl | O | 4-CH₂ | 0 | | |
| 1.1136 | 3-C₅H₄N | C₆H₄-2-Cl | O | 3-CH₂ | 0 | | |
| 1.1137 | 3-C₅H₄N | C₆H₄-2-Cl | O | 2-CH₂ | 0 | | |
| 1.1138 | 3-C₅H₄N | C₆H₄-2-Cl | O | 4-OCH₂ | 0 | | |
| 1.1139 | 3-C₅H₄N | C₆H₄-2-Cl | O | 3-OCH₂ | 0 | | |
| 1.1140 | 3-C₅H₄N | C₆H₄-2-Cl | O | 2-OCH₂ | 0 | | |
| 1.1141 | 3-C₅H₄N | C₆H₄-2-Cl | O | 4-S | 0 | | |
| 1.1142 | 3-C₅H₄N | C₆H₄-2-Cl | O | 3-S | 0 | | |

TABLE 1-continued

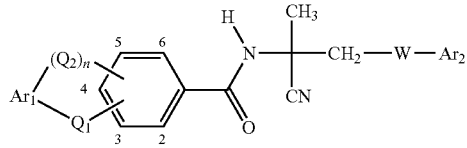

| No. | Ar₁ | Ar₂ | W | Q₁ | n | Q₂ | phys. data |
|---|---|---|---|---|---|---|---|
| 1.1143 | 3-C₅H₄N | C₆H₄-2-Cl | O | 2-S | 0 | | |
| 1.1144 | 3-C₅H₄N | C₆H₄-2-Cl | O | 4-S(O) | 0 | | |
| 1.1145 | 3-C₅H₄N | C₆H₄-2-Cl | O | 3-S(O) | 0 | | |
| 1.1146 | 3-C₅H₄N | C₆H₄-2-Cl | O | 2-S(O) | 0 | | |
| 1.1147 | 3-C₅H₄N | C₆H₄-2-Cl | O | 4-C(O) | 0 | | |
| 1.1148 | 3-C₅H₄N | C₆H₄-2-Cl | O | 3-C(O) | 0 | | |
| 1.1149 | 3-C₅H₄N | C₆H₄-2-Cl | O | 2-C(O) | 0 | | |
| 1.1150 | 3-C₅H₄N | C₆H₄-2-Cl | S | 4-CH₂ | 0 | | |
| 1.1151 | 3-C₅H₄N | C₆H₄-2-Cl | S | 3-CH₂ | 0 | | |
| 1.1152 | 3-C₅H₄N | C₆H₄-2-Cl | S | 2-CH₂ | 0 | | |
| 1.1153 | 3-C₅H₄N | C₆H₄-2-Cl | S | 4-OCH₂ | 0 | | |
| 1.1154 | 3-C₅H₄N | C₆H₄-2-Cl | S | 3-OCH₂ | 0 | | |
| 1.1155 | 3-C₅H₄N | C₆H₄-2-Cl | S | 2-OCH₂ | 0 | | |
| 1.1156 | 3-C₅H₄N | C₆H₄-2-Cl | S | 4-S | 0 | | |
| 1.1157 | 3-C₅H₄N | C₆H₄-2-Cl | S | 3-S | 0 | | |
| 1.1158 | 3-C₅H₄N | C₆H₄-2-Cl | S | 2-S | 0 | | |
| 1.1159 | 3-C₅H₄N | C₆H₄-2-Cl | S | 4-S(O) | 0 | | |
| 1.1160 | 3-C₅H₄N | C₆H₄-2-Cl | S | 3-S(O) | 0 | | |
| 1.1161 | 3-C₅H₄N | C₆H₄-2-Cl | S | 2-S(O) | 0 | | |
| 1.1162 | 3-C₅H₄N | C₆H₄-2-Cl | S | 4-C(O) | 0 | | |
| 1.1163 | 3-C₅H₄N | C₆H₄-2-Cl | S | 3-C(O) | 0 | | |
| 1.1164 | 3-C₅H₄N | C₆H₄-2-Cl | S | 2-C(O) | 0 | | |
| 1.1165 | 3-C₅H₄N | C₆H₄-2-CF₃ | O | 4-CH₂ | 0 | | |
| 1.1166 | 3-C₅H₄N | C₆H₄-2-CF₃ | O | 3-CH₂ | 0 | | |
| 1.1167 | 3-C₅H₄N | C₆H₄-2-CF₃ | O | 2-CH₂ | 0 | | |
| 1.1168 | 3-C₅H₄N | C₆H₄-2-CF₃ | O | 4-OCH₂ | 0 | | |
| 1.1169 | 3-C₅H₄N | C₆H₄-2-CF₃ | O | 3-OCH₂ | 0 | | |
| 1.1170 | 3-C₆H₄N | C₆H₄-2-CF₃ | O | 2-OCH₂ | 0 | | |
| 1.1171 | 3-C₅H₄N | C₆H₄-2-CF₃ | O | 4-S | 0 | | |
| 1.1172 | 3-C₅H₄N | C₆H₄-2-CF₃ | O | 3-S | 0 | | |
| 1.1173 | 3-C₅H₄N | C₆H₄-2-CF₃ | O | 2-S | 0 | | |
| 1.1174 | 3-C₅H₄N | C₆H₄-2-CF₃ | O | 4-S(O) | 0 | | |
| 1.1175 | 3-C₅H₄N | C₆H₄-2-CF₃ | O | 3-S(O) | 0 | | |
| 1.1176 | 3-C₅H₄N | C₆H₄-2-CF₃ | O | 2-S(O) | 0 | | |
| 1.1177 | 3-C₅H₄N | C₆H₄-2-CF₃ | O | 4-C(O) | 0 | | |
| 1.1178 | 3-C₅H₄N | C₆H₄-2-CF₃ | O | 3-C(O) | 0 | | |
| 1.1179 | 3-C₅H₄N | C₆H₄-2-CF₃ | O | 2-C(O) | 0 | | |
| 1.1180 | 3-C₅H₄N | C₆H₄-2-CF₃ | S | 4-CH₂ | 0 | | |
| 1.1181 | 3-C₅H₄N | C₆H₄-2-CF₃ | S | 3-CH₂ | 0 | | |
| 1.1182 | 3-C₅H₄N | C₆H₄-2-CF₃ | S | 2-CH₂ | 0 | | |
| 1.1183 | 3-C₅H₄N | C₆H₄-2-CF₃ | S | 4-OCH₂ | 0 | | |
| 1.1184 | 3-C₅H₄N | C₆H₄-2-CF₃ | S | 3-OCH₂ | 0 | | |
| 1.1185 | 3-C₅H₄N | C₆H₄-2-CF₃ | S | 2-OCH₂ | 0 | | |
| 1.1186 | 3-C₅H₄N | C₆H₄-2-CF₃ | S | 4-S | 0 | | |
| 1.1187 | 3-C₅H₄N | C₆H₄-2-CF₃ | S | 3-S | 0 | | |
| 1.1188 | 3-C₅H₄N | C₆H₄-2-CF₃ | S | 2-S | 0 | | |
| 1.1189 | 3-C₅H₄N | C₆H₄-2-CF₃ | S | 4-S(O) | 0 | | |
| 1.1190 | 3-C₅H₄N | C₆H₄-2-CF₃ | S | 3-S(O) | 0 | | |
| 1.1191 | 3-C₅H₄N | C₆H₄-2-CF₃ | S | 2-S(O) | 0 | | |
| 1.1192 | 3-C₅H₄N | C₆H₄-2-CF₃ | S | 4-C(O) | 0 | | |
| 1.1193 | 3-C₅H₄N | C₆H₄-2-CF₃ | S | 3-C(O) | 0 | | |
| 1.1194 | 3-C₆H₄N | C₆H₄-2-CF₃ | S | 2-C(O) | 0 | | |
| 1.1195 | 2-C₄H₃S | C₆H₅ | O | 4-CH₂ | 0 | | |
| 1.1196 | 2-C₄H₃S | C₆H₅ | O | 3-CH₂ | 0 | | |
| 1.1197 | 2-C₄H₃S | C₆H₅ | O | 2-CH₂ | 0 | | |
| 1.1198 | 2-C₄H₃S | C₆H₅ | O | 4-OCH₂ | 0 | | |
| 1.1199 | 2-C₄H₃S | C₆H₅ | O | 3-OCH₂ | 0 | | |
| 1.1200 | 2-C₄H₃S | C₆H₅ | O | 2-OCH₂ | 0 | | |
| 1.1201 | 2-C₄H₃S | C₆H₅ | O | 4-S | 0 | | |
| 1.1202 | 2-C₄H₃S | C₆H₅ | O | 3-S | 0 | | |
| 1.1203 | 2-C₄H₃S | C₆H₅ | O | 2-S | 0 | | |
| 1.1204 | 2-C₄H₃S | C₆H₅ | O | 4-S(O) | 0 | | |
| 1.1205 | 2-C₄H₃S | C₆H₅ | O | 3-S(O) | 0 | | |
| 1.1206 | 2-C₄H₃S | C₆H₅ | O | 2-S(O) | 0 | | |
| 1.1207 | 2-C₄H₃S | C₆H₅ | O | 4-C(O) | 0 | | |
| 1.1208 | 2-C₄H₃S | C₆H₅ | O | 3-C(O) | 0 | | |
| 1.1209 | 2-C₄H₃S | C₆H₅ | O | 2-C(O) | 0 | | |
| 1.1210 | 2-C₄H₃S | C₆H₅ | S | 4-CH₂ | 0 | | |

TABLE 1-continued

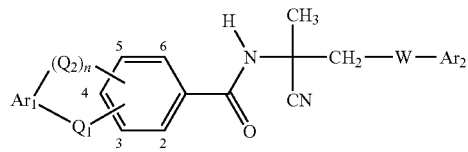

| No. | Ar$_1$ | Ar$_2$ | W | Q$_1$ | n | Q$_2$ | phys. data |
|---|---|---|---|---|---|---|---|
| 1.1211 | 2-C$_4$H$_3$S | C$_6$H$_5$ | S | 3-CH$_2$ | 0 | | |
| 1.1212 | 2-C$_4$H$_3$S | C$_6$H$_5$ | S | 2-CH$_2$ | 0 | | |
| 1.1213 | 2-C$_4$H$_3$S | C$_6$H$_5$ | S | 4-OCH$_2$ | 0 | | |
| 1.1214 | 2-C$_4$H$_3$S | C$_6$H$_5$ | S | 3-OCH$_2$ | 0 | | |
| 1.1215 | 2-C$_4$H$_3$S | C$_6$H$_5$ | S | 2-OCH$_2$ | 0 | | |
| 1.1216 | 2-C$_4$H$_3$S | C$_6$H$_5$ | S | 4-S | 0 | | |
| 1.1217 | 2-C$_4$H$_3$S | C$_6$H$_5$ | S | 3-S | 0 | | |
| 1.1218 | 2-C$_4$H$_3$S | C$_6$H$_5$ | S | 2-S | 0 | | |
| 1.1219 | 2-C$_4$H$_3$S | C$_6$H$_5$ | S | 4-S(O) | 0 | | |
| 1.1220 | 2-C$_4$H$_3$S | C$_6$H$_5$ | S | 3-S(O) | 0 | | |
| 1.1221 | 2-C$_4$H$_3$S | C$_6$H$_5$ | S | 2-S(O) | 0 | | |
| 1.1222 | 2-C$_4$H$_3$S | C$_6$H$_5$ | S | 4-C(O) | 0 | | |
| 1.1223 | 2-C$_4$H$_3$S | C$_6$H$_5$ | S | 3-C(O) | 0 | | |
| 1.1224 | 2-C$_4$H$_3$S | C$_6$H$_5$ | S | 2-C(O) | 0 | | |
| 1.1225 | 2-C$_4$H$_3$S | C$_6$H$_4$-2-Cl | O | 4-CH$_2$ | 0 | | |
| 1.1226 | 2-C$_4$H$_3$S | C$_6$H$_4$-2-Cl | O | 3-CH$_2$ | 0 | | |
| 1.1227 | 2-C$_4$H$_3$S | C$_6$H$_4$-2-Cl | O | 2-CH$_2$ | 0 | | |
| 1.1228 | 2-C$_4$H$_3$S | C$_6$H$_4$-2-Cl | O | 4-OCH$_2$ | 0 | | |
| 1.1229 | 2-C$_4$H$_3$S | C$_6$H$_4$-2-Cl | O | 3-OCH$_2$ | 0 | | |
| 1.1230 | 2-C$_4$H$_3$S | C$_6$H$_4$-2-Cl | O | 2-OCH$_2$ | 0 | | |
| 1.1231 | 2-C$_4$H$_3$S | C$_6$H$_4$-2-Cl | O | 4-S | 0 | | |
| 1.1232 | 2-C$_4$H$_3$S | C$_6$H$_4$-2-Cl | O | 3-S | 0 | | |
| 1.1233 | 2-C$_4$H$_3$S | C$_6$H$_4$-2-Cl | O | 2-S | 0 | | |
| 1.1234 | 2-C$_4$H$_3$S | C$_6$H$_4$-2-Cl | O | 4-S(O) | 0 | | |
| 1.1235 | 2-C$_4$H$_3$S | C$_6$H$_4$-2-Cl | O | 3-S(O) | 0 | | |
| 1.1236 | 2-C$_4$H$_3$S | C$_6$H$_4$-2-Cl | O | 2-S(O) | 0 | | |
| 1.1237 | 2-C$_4$H$_3$S | C$_6$H$_4$-2-Cl | O | 4-C(O) | 0 | | |
| 1.1238 | 2-C$_4$H$_3$S | C$_6$H$_4$-2-Cl | O | 3-C(O) | 0 | | |
| 1.1239 | 2-C$_4$H$_3$S | C$_6$H$_4$-2-Cl | O | 2-C(O) | 0 | | |
| 1.1240 | 2-C$_4$H$_3$S | C$_6$H$_4$-2-Cl | S | 4-CH$_2$ | 0 | | |
| 1.1241 | 2-C$_4$H$_3$S | C$_6$H$_4$-2-Cl | S | 3-CH$_2$ | 0 | | |
| 1.1242 | 2-C$_4$H$_3$S | C$_6$H$_4$-2-Cl | S | 2-CH$_2$ | 0 | | |
| 1.1243 | 2-C$_4$H$_3$S | C$_6$H$_4$-2-Cl | S | 4-OCH$_2$ | 0 | | |
| 1.1244 | 2-C$_4$H$_3$S | C$_6$H$_4$-2-Cl | S | 3-OCH$_2$ | 0 | | |
| 1.1245 | 2-C$_4$H$_3$S | C$_6$H$_4$-2-Cl | S | 2-OCH$_2$ | 0 | | |
| 1.1246 | 2-C$_4$H$_3$S | C$_6$H$_4$-2-Cl | S | 4-S | 0 | | |
| 1.1247 | 2-C$_4$H$_3$S | C$_6$H$_4$-2-Cl | S | 3-S | 0 | | |
| 1.1248 | 2-C$_4$H$_3$S | C$_6$H$_4$-2-Cl | S | 2-S | 0 | | |
| 1.1249 | 2-C$_4$H$_3$S | C$_6$H$_4$-2-Cl | S | 4-S(O) | 0 | | |
| 1.1250 | 2-C$_4$H$_3$S | C$_6$H$_4$-2-Cl | S | 3-S(O) | 0 | | |
| 1.1251 | 2-C$_4$H$_3$S | C$_6$H$_4$-2-Cl | S | 2-S(O) | 0 | | |
| 1.1252 | 2-C$_4$H$_3$S | C$_6$H$_4$-2-Cl | S | 4-C(O) | 0 | | |
| 1.1253 | 2-C$_4$H$_3$S | C$_6$H$_4$-2-Cl | S | 3-C(O) | 0 | | |
| 1.1254 | 2-C$_4$H$_3$S | C$_6$H$_4$-2-Cl | S | 2-C(O) | 0 | | |
| 1.1255 | 2-C$_4$H$_3$S | C$_6$H$_4$-2-CF$_3$ | O | 4-CH$_2$ | 0 | | |
| 1.1256 | 2-C$_4$H$_3$S | C$_6$H$_4$-2-CF$_3$ | O | 3-CH$_2$ | 0 | | |
| 1.1257 | 2-C$_4$H$_3$S | C$_6$H$_4$-2-CF$_3$ | O | 2-CH$_2$ | 0 | | |
| 1.1258 | 2-C$_4$H$_3$S | C$_6$H$_4$-2-CF$_3$ | O | 4-OCH$_2$ | 0 | | |
| 1.1259 | 2-C$_4$H$_3$S | C$_6$H$_4$-2-CF$_3$ | O | 3-OCH$_2$ | 0 | | |
| 1.1260 | 2-C$_4$H$_3$S | C$_6$H$_4$-2-CF$_3$ | O | 2-OCH$_2$ | 0 | | |
| 1.1261 | 2-C$_4$H$_3$S | C$_6$H$_4$-2-CF$_3$ | O | 4-S | 0 | | |
| 1.1262 | 2-C$_4$H$_3$S | C$_6$H$_4$-2-CF$_3$ | O | 3-S | 0 | | |
| 1.1263 | 2-C$_4$H$_3$S | C$_6$H$_4$-2-CF$_3$ | O | 2-S | 0 | | |
| 1.1264 | 2-C$_4$H$_3$S | C$_6$H$_4$-2-CF$_3$ | O | 4-S(O) | 0 | | |
| 1.1265 | 2-C$_4$H$_3$S | C$_6$H$_4$-2-CF$_3$ | O | 3-S(O) | 0 | | |
| 1.1266 | 2-C$_4$H$_3$S | C$_6$H$_4$-2-CF$_3$ | O | 2-S(O) | 0 | | |
| 1.1267 | 2-C$_4$H$_3$S | C$_6$H$_4$-2-CF$_3$ | O | 4-C(O) | 0 | | |
| 1.1268 | 2-C$_4$H$_3$S | C$_6$H$_4$-2-CF$_3$ | O | 3-C(O) | 0 | | |
| 1.1269 | 2-C$_4$H$_3$S | C$_6$H$_4$-2-CF$_3$ | O | 2-C(O) | 0 | | |
| 1.1270 | 2-C$_4$H$_3$S | C$_6$H$_4$-2-CF$_3$ | S | 4-CH$_2$ | 0 | | |
| 1.1271 | 2-C$_4$H$_3$S | C$_6$H$_4$-2-CF$_3$ | S | 3-CH$_2$ | 0 | | |
| 1.1272 | 2-C$_4$H$_3$S | C$_6$H$_4$-2-CF$_3$ | S | 2-CH$_2$ | 0 | | |
| 1.1273 | 2-C$_4$H$_3$S | C$_6$H$_4$-2-CF$_3$ | S | 4-OCH$_2$ | 0 | | |
| 1.1274 | 2-C$_4$H$_3$S | C$_6$H$_4$-2-CF$_3$ | S | 3-OCH$_2$ | 0 | | |
| 1.1275 | 2-C$_4$H$_3$S | C$_6$H$_4$-2-CF$_3$ | S | 2-OCH$_2$ | 0 | | |
| 1.1276 | 2-C$_4$H$_3$S | C$_6$H$_4$-2-CF$_3$ | S | 4-S | 0 | | |
| 1.1277 | 2-C$_4$H$_3$S | C$_6$H$_4$-2-CF$_3$ | S | 3-S | 0 | | |
| 1.1278 | 2-C$_4$H$_3$S | C$_6$H$_4$-2-CF$_3$ | S | 2-S | 0 | | |

TABLE 1-continued

[Structure: Ar$_1$-Q$_1$-(Q$_2$)$_n$-[benzene ring positions 2,3,4,5,6]-C(O)-N(H)-C(CH$_3$)(CN)-CH$_2$-W-Ar$_2$]

| No. | Ar$_1$ | Ar$_2$ | W | Q$_1$ | n | Q$_2$ | phys. data |
|---|---|---|---|---|---|---|---|
| 1.1279 | 2-C$_4$H$_3$S | C$_6$H$_4$-2-CF$_3$ | S | 4-S(O) | 0 | | |
| 1.1280 | 2-C$_4$H$_3$S | C$_6$H$_4$-2-CF$_3$ | S | 3-S(O) | 0 | | |
| 1.1281 | 2-C$_4$H$_3$S | C$_6$H$_4$-2-CF$_3$ | S | 2-S(O) | 0 | | |
| 1.1282 | 2-C$_4$H$_3$S | C$_6$H$_4$-2-CF$_3$ | S | 4-C(O) | 0 | | |
| 1.1283 | 2-C$_4$H$_3$S | C$_6$H$_4$-2-CF$_3$ | S | 3-C(O) | 0 | | |
| 1.1284 | 2-C$_4$H$_3$S | C$_6$H$_4$-2-CF$_3$ | S | 2-C(O) | 0 | | |

TABLE 2

[Structure: phenyl-Q$_1$-[benzene ring positions 2,3,4,5,6]-C(O)-N(H)-C(CH$_3$)(CN)-CH$_2$-O-Ar$_2$]

| No. | Q$_1$ | Ar$_2$ | phys. data |
|---|---|---|---|
| 2.1 | 4-CH(OH) | C$_6$H$_4$-2-CF$_3$ | m.p. 72° |
| 2.2 | 4-C(CH$_3$)(OH) | C$_6$H$_4$-2-CF$_3$ | m.p. 108-10° |
| 2.3 | 4-C(NOCH$_3$) | C$_6$H$_4$-2-CF$_3$ | m.p. 61° |
| 2.4 | 4-C(O) | C$_6$H$_3$-2-Cl-5-CH$_3$ | m.p. 148-50° |
| 2.5 | 4-C(O) | C$_6$H$_3$-2,5-Cl$_2$ | m.p. 160-2° |
| 2.6 | 4-C(O) | C$_6$H$_2$-2-Br-4,5-F$_2$ | m.p. 69-71° |

Biological Examples

1. In-Vivo Test on *Trichostrongylus colubriformis* and *Haemonchus contortus* on Mongolian Gerbils (*Meiones unguiculatus*) Using Peroral Application Six to eight week old Mongolian gerbils are infected by artificial feeding with ca. 2000 third instar larvae each of *T. colubriformis* and *H. contortus*. 6 days after infection, the gerbils are lightly anaesthetised with N$_2$O and treated by peroral application with the test compounds, dissolved in a mixture of 2 parts DMSO and 1 part polyethylene glycol (PEG 300), in quantities of 100, 32 and 10-0.1 mg/kg. On day 9 (3 days after treatment), when most of the *H. contortus* that are still present are late 4th instar larvae and most of the *T. colubdformis* are immature adults, the gerbils are killed in order to count the worms. The efficacy is calculated as the % reduction of the number of worms in each gerbil, compared with the geometric average of number of worms from 8 infected and untreated gerbils.

In this test, a vast reduction in nematode infestation is achieved with compounds of formula I, especially from Table 1. In particular, compounds 1.59 and 1.105 effect a 100% reduction in *Trichostrongylus* infestation even at doses of 32 mg/kg.

To examine the insecticidal and/or acaricidal activity of the compounds of formula I on animals and plants, the following test methods may be used.

2. Insecticidal Stomach Toxicant Activity on *Spodoptera littoralils*

Potted cotton plants at the 5-leaf stage are each sprayed with an acetonic/aqueous test solution containing 1, 3, 12.5 or 50 ppm of the compound to be tested.

After drying of the spray deposit, the plants are colonised with ca. 30 larvae (L$_1$ stage) of *Spodoptera littoralis*. Two plants are used per test compound and per test species. The test is carried out at ca. 24° C. and at 60% relative humidity. Evaluations and intermediate evaluations on moribund animals, larvae and feeding damage are made after 24, 48 and 72 h.

3. Activity on Phytotoxic Acarids

OP-Sensitive *Tetranychus urticae*

The primary leaves of bean plants (*Phaseolus vulgais*) are covered 16 hours before the test with a mass-cultivated piece of leaf infested with *T. urticae*. After removing the piece of leaf, the plants that are infested with all stages of the mites are sprayed to drip point with a test solution containing either 0.2, 0.4 or 1.6 ppm of the compound to be tested. The temperature in the greenhouse is ca. 25° C. After 7 days, an evaluation of the percentage of mobile stages (adults and nymphs) and of eggs is made under a microscope.

4. Activity on L$_1$ Larvae of *Lucilia sedcata*

1 ml of an aqueous suspension of the active substance to be tested is admixed with 3 ml of a special larvae growth medium at ca. 50° C., so that a homogenate of either 250 or 125 ppm of active ingredient content is obtained. Ca. 30 *Lucilia* larvae (L$_1$) are used in each test tube sample. After 4 days, the mortality rate is determined.

5. Acaricidal Activity on *Boophilus microplus* (Biarra Strain)

A piece of sticky tape is attached horizontally to a PVC sheet, so that 10 fully engorged female ticks of *Boophilus microplus* (Biarra strain) can be adhered thereto by their backs, side by side, in a row. Using an injection needle, 1 µl of a liquid is injected into each tick. The liquid is a 1:1 mixture of polyethylene glycol and acetone and it contains, dissolved therein, a certain amount of active ingredient chosen from 1, 0.1 or 0.01 µg per tick. Control animals are given an injection without active ingredient. After treatment, the animals are kept under normal conditions in an insectarium at ca. 28° C. and at 80% relative humidity until oviposition takes place and the larvae have hatched from the eggs of the control animals. The activity of a tested substance is determined by $IR_{90}$, i.e. an evaluation is made of the dosage of active ingredient at which 9 out of 10 female ticks (=90%) lay eggs that are infertile even after 30 days.

6. In Vitro Efficacy on Engorged Female *Boophilus microbus* (BIARRA):

4×10 engorged female ticks of the OP-resistant BIARRA strain are adhered to a sticky strip and covered for 1 hour with a cotton-wool ball soaked in an emulsion or suspension of the test compound in concentrations of 500, 125, 31 and 8 ppm respectively. Evaluation takes place 28 days later based on mortality, oviposition and hatched larvae.

An indication of the activity of the test compounds is shown by the number of females that
- die quickly before laying eggs,
- survive for some time without laying eggs,
- lay eggs in which no embryos are formed,
- lay eggs in which embryos form, from which no larvae hatch, and
- lay eggs in which embryos form, from which larvae normally hatch within 26 to 27 days.

7. Contact Action on *Aphis craccivora*

Pea seedlings that have been infested with all stages of development of the aphids are sprayed with a solution of active ingredient prepared from an emulsion concentrate, the solution containing 50, 25 or 12.5 ppm of active ingredient, as desired. After 3 days, an evaluation is made of more than 80% of aphids that are either dead or have fallen off. Only at this level of activity is a preparation classified as effective.

8. Larvicidal Activity on *Aedes aegypti*

A sufficient quantity of a 0.1% acetonic solution of the active ingredient for a chosen concentration of 10, 3.3 or 1.6 ppm to be attained, is added by pipette to the surface of 150 ml of water in a container. After evaporation of the acetone, the container is covered with ca. 30-403-day old *Aedes* larvae. After 1, 2 and 5 days, the mortality is tested.

9. In Vivo Efficacy on Adult *Ctenoceohalides felis* on Domestic Cats After Oral Treatment The test substances are given orally to domestic cats in a gelatin capsule before or after feeding, the dose varying between 0.5 and 20 mg/kg. On days 1, 3, 7 and 10 after treatment, each cat is exposed to 100 fleas (ca. 50 male and ca. 50 female), depending on the result of previous flea colonisation. The efficacy (in % reduction in flea numbers) is based on the number of living fleas found after combing for 10 minutes one day after each new flea colonisation, whereby the efficacy in % corresponds to the arithmetic average of the number of living fleas on control animals minus the number of living fleas on the treated animals, divided by the arithmetic average of the number of living fleas on control animals and multiplied by 100.

The dying fleas found in the cat cages and by combing are collected, placed in an incubator at 28° C. and 70% relative humidity and after 24 hours are tested for survival/mortality. If the majority of dying fleas die, the test compound is regarded as a flea adulticide, and if the majority survive, the test compound shows "knock-down" activity.

10. In Vivo Efficacy on Adult *Ctenocephalides felis* on Domestic Cats After Spot-On Treatment The test substances are given to domestic cats as spot-on treatment, the dose varying between 0.5 and 10 mg/kg. On days 1, 3, 7 and 10 after treatment, each cat is exposed to 100 fleas (ca. 50 male and ca. 50 female), depending on the result of previous flea colonisation.

The efficacy (in % reduction in flea numbers) is based on the number of living fleas found after combing for 10 minutes one day after each new flea colonisation, whereby the efficacy in % corresponds to the arithmetic average of the number of living fleas on control animals minus the number of living fleas on the treated animals, divided by the arithmetic average of the number of living fleas on control animals and multiplied by 100.

The dying fleas found in the cat cages and by combing are collected, placed in an incubator at 28° C. and 70% relative humidity and after 24 hours are tested for survival/mortality. If the majority of dying fleas die, the test compound is regarded as a flea adulticide, and if the majority survive, the test compound shows "knock-down" activity.

11. In Vitro Efficacy on Nymphs of *Amblyomma hebraeum*

About 5 fasting nymphs are placed in a polystyrene test tube containing 2 ml of the test compound in solution, suspension or emulsion.

After immersion for 10 minutes, and shaking for 2×10 seconds on a vortex mixer, the test tubes are blocked up with a tight wad of cotton wool and rotated. As soon as all the liquid has been soaked up by the cotton wool ball, it is pushed half-way into the test tube which is still being rotated, so that most of the liquid is squeezed out of the cotton-wool ball and flows into a Petri dish below.

The test tubes are then kept at room temperature in a room with daylight until evaluated. After 14 days, the test tubes are immersed in a beaker of boiling water. If the ticks begin to move in reaction to the heat, the test substance is inactive at the tested concentration, otherwise the ticks are regarded as dead and the test substances regarded as active at the tested concentration. All substances are tested in a concentration range of 0.1 to 100 ppm.

12. Activity Against *Dermanyssus gallinae*

2 to 3 ml of a solution containing 10 ppm active ingredient, and ca. 200 mites (*Dermanyssus gallinae*) at different stages of development are added to a glass container which is open at the top. Then the container is closed with a wad of cotton wool, shaken for 10 minutes until the mites are completely wet, and then inverted briefly so that the remaining test solution can be absorbed by the cotton wool. After 3 days, the mortality of the mites is determined by counting the dead individuals and indicated as a percentage.

13. Activity Against *Musca domestica*

A sugar cube is treated with a solution of the test substance in such a way that the concentration of test substance in the sugar, after drying over night, is 250 ppm. The cube treated in this way is placed on an aluminium dish with wet cotton wool and 10 adult *Musca domestica* of an OP-resistant strain, covered with a beaker and incubated at 25° C. The mortality rate is determined after 24 hours.

What we claim is:

1. A compound of formula I:

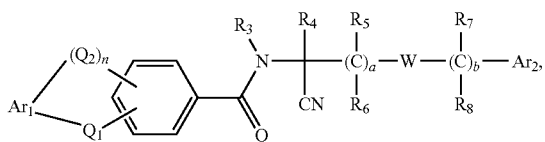

wherein each of $Ar_1$ and $Ar_2$, independently of one another, signify phenyl that is either unsubstituted or substituted one or more times, whereby the substituents may be independent of one another and are selected from the group consisting of halogen, $C_1$-$C_6$-alkyl, halo-$C_1$-$C_6$-alkyl, $C_1$-$C_8$-alkoxy, halo-$C_1$-$C_6$-alkoxy, $C_3$-$C_6$-cycloalkyl, $C_1$-$C_6$-alkylthio, halo-$C_1$-$C_6$-alkylthio, $C_1$-$C_6$-alkylcarbonyl, halo-$C_1$-$C_6$-alkylcarbonyl, $C_1$-$C_6$-alkoxycarbonyl, $C_1$-$C_6$-alkylaminocarbonyl, and di-$C_1$-$C_6$-alkylaminocarbonyl;

$Q_1$ signifies C(O);

$R_3$ signifies hydrogen or $C_1$-$C_2$-alkyl;

each of $R_4$, $R_5$, $R_6$, $R_7$, and $R_8$, independently of one another, signify hydrogen, halogen, $C_1$-$C_6$-alkyl, halo-$C_1$-$C_6$-alkyl, or $C_3$-$C_6$-cycloalkyl;

W signifies O or N($R_9$);

$R_9$ signifies hydrogen or $C_1$-$C_2$-alkyl;

a signifies 1, 2, 3, or 4;

b signifies 0, 1, 2, 3, or 4; and n signifies 0.

2. A compound of formula I according to claim 1, wherein each of $Ar_1$ and $Ar_2$, independently of one another, signify phenyl that is either unsubstituted or substituted one or more times, whereby the substituents may be independent of one another and are selected from the group consisting of halogen, $C_1$-$C_6$-alkyl, halo-$C_1$-$C_6$-alkyl, $C_1$-$C_6$-alkoxy, and halo-$C_1$-$C_6$-alkoxy;

$Q_1$ signifies C(O);

$R_3$ signifies hydrogen;

each of $R_4$, $R_5$, $R_6$, $R_7$, and $R_8$, independently of one another, signify hydrogen, halogen, $C_1$-$C_6$-alkyl, or halo-$C_1$-$C_6$-alkyl;

W signifies O;

$R_9$ signifies methyl;

a signifies 1;

b signifies 0 or 1; and n is 0.

3. A compound of formula I according to claim 1 wherein the compound is 4-Benzoyl-N-[1-cyano-1-methyl-2-(2-trifluoromethylphenoxy)-ethyl]-benzamide.

4. A composition for the control of parasites, comprising at least one compound of formula I according to claim 1 and one or more carriers or dispersants.

5. A method of controlling parasites in an animal in need thereof, comprising administering to said animal a parasiticidal amount of a compound of formula I as defined in claim 1.

6. The method of claim 5, whereby said animals are warm-blooded animals.

7. A method for controlling pests comprising administering to said pests an effective amount of a compound of formula I as defined in claim 1 to kill said pests.

8. A compound of formula I according to claim 1, wherein $R_3$ signifies hydrogen.

9. A compound of formula I according to claim 1, wherein each of $R_4$, $R_5$, $R_6$, $R_7$, and $R_8$, independently of one another, is hydrogen, halogen, $C_1$-$C_6$-alkyl, or halo-$C_1$-$C_6$-alkyl.

10. A compound of formula I according to claim 1, wherein W is O.

11. A compound of formula I according to claim 1, wherein a is 1.

12. A compound of formula I according to claim 1, wherein b is 0 or 1.

* * * * *